(12) United States Patent
Broverman et al.

(10) Patent No.: US 8,504,380 B2
(45) Date of Patent: Aug. 6, 2013

(54) ASSISTANCE FOR CLINICAL TRIAL PROTOCOLS

(75) Inventors: Carol A. Broverman, Menlo Park, CA (US); Michael G. Kahn, Boulder, CO (US); Christopher Noon, Dublin, CA (US)

(73) Assignee: Medidata Solutions, Inc., New York, NY (US)

(*) Notice: Subject to any disclaimer, the term of this patent is extended or adjusted under 35 U.S.C. 154(b) by 1522 days.

(21) Appl. No.: 10/454,954

(22) Filed: Jun. 5, 2003

(65) Prior Publication Data

US 2004/0249664 A1    Dec. 9, 2004

(51) Int. Cl.
*G06Q 10/00*    (2012.01)

(52) U.S. Cl.
USPC .................................. 705/2; 705/3

(58) Field of Classification Search
USPC ............................................. 705/2
See application file for complete search history.

(56) References Cited

U.S. PATENT DOCUMENTS

| | | |
|---|---|---|
| 4,992,939 A | 2/1991 | Tyler |
| 5,148,366 A | 9/1992 | Buchanan et al. |
| 5,181,162 A | 1/1993 | Smith et al. |
| 5,222,236 A | 6/1993 | Potash et al. |
| 5,267,155 A | 11/1993 | Buchanan et al. |
| 5,272,623 A | 12/1993 | Grubb et al. |
| 5,369,763 A | 11/1994 | Biles |
| 5,553,216 A | 9/1996 | Yoshioka et al. |
| 5,655,130 A | 8/1997 | Dodge et al. |
| 5,657,255 A | 8/1997 | Fink et al. |
| 5,666,490 A | 9/1997 | Gillings et al. |
| 5,734,883 A | 3/1998 | Umen et al. |
| 5,774,887 A | 6/1998 | Wolff et al. |
| 5,812,983 A | 9/1998 | Kumagai |
| 5,812,984 A | 9/1998 | Goltra |
| 5,832,449 A | 11/1998 | Cunningham |

(Continued)

FOREIGN PATENT DOCUMENTS

| | | |
|---|---|---|
| CA | 2150765 | 12/1995 |
| EP | 0 832 462 B1 | 8/2002 |

(Continued)

OTHER PUBLICATIONS

Thierry dart, Yigang Xu, Gilles chatellier, Patrice Degoulet, Computerzation of Guidelines: towards a "Gudeline Markup Language",2001, Medinfo 2001, V. Patel et al (Eds), Amsterdam; http://cmbi.bjmu.edu.cn/news/report/2001/medinfo_2001/Papers/Ch4/465_dart.pdf.*

(Continued)

*Primary Examiner* — Hiep V Nguyen
(74) *Attorney, Agent, or Firm* — Hoffmann & Baron, LLP

(57) ABSTRACT

Roughly described, a user instantiates protocol elements in a structured clinical trial protocol database and then draws from them in the development of one or more protocol related documents. The system helps the user select tasks to be performed during the study by reference to a historical database of tasks previously associated with similar protocols. The system automatically generates complex content from protocol elements in the database, and can render overlapping sets of protocol elements differently at different locations in the document. The system can automatically provide advisories indicating aspects of the document that still require completion or highlighting other issues that a sponsoring authority deems important for the document type. Alter all protocol elements are instantiated in the protocol database, it can then be used to drive the operation of most downstream aspects of the study.

37 Claims, 48 Drawing Sheets

U.S. PATENT DOCUMENTS

| | | | |
|---|---|---|---|
| 5,867,821 | A | 2/1999 | Ballantyne et al. |
| 5,963,967 | A | 10/1999 | Umen et al. |
| 5,991,731 | A | 11/1999 | Colon et al. |
| 6,055,494 | A | 4/2000 | Friedman |
| 6,081,786 | A | 6/2000 | Barry et al. |
| 6,081,809 | A | 6/2000 | Kumagai |
| 6,108,635 | A | 8/2000 | Herren et al. |
| 6,182,029 | B1 | 1/2001 | Friedman |
| 6,196,970 | B1 | 3/2001 | Brown |
| 6,205,455 | B1 | 3/2001 | Umen et al. |
| 6,505,218 | B2 | 1/2003 | Umen et al. |
| 6,820,235 | B1 * | 11/2004 | Bleicher et al. ............... 715/236 |
| 7,054,823 | B1 * | 5/2006 | Briegs et al. ...................... 705/2 |
| 7,444,293 | B1 | 10/2008 | Kahn et al. |
| 2001/0001852 | A1 | 5/2001 | Rovinelli et al. |
| 2001/0051882 | A1 * | 12/2001 | Murphy et al. .................... 705/3 |
| 2002/0016530 | A1 | 2/2002 | Brown |
| 2002/0077853 | A1 * | 6/2002 | Boru et al. ........................ 705/2 |
| 2002/0103811 | A1 | 8/2002 | Fankhauser et al. |
| 2003/0065669 | A1 | 4/2003 | Kahn et al. |
| 2003/0108938 | A1 * | 6/2003 | Pickar et al. ...................... 435/6 |

FOREIGN PATENT DOCUMENTS

| | | |
|---|---|---|
| EP | 1 244 024 A2 | 9/2002 |
| WO | WO 96/34348 | 10/1996 |
| WO | WO 98/49647 | 11/1998 |
| WO | WO 99/63473 | 12/1999 |
| WO | WO 01/93178 A2 | 12/2001 |

OTHER PUBLICATIONS

Government Forms Software, Inc., Products Page, available at http://www.enlightenedsoftware.com/products.htm (visited Apr. 18, 2003).

Intuit, TurboTax User's Guide , pp. 34-41(1999).

WordPerfect for DOS, Version 5.1, Reference Manual, Appendices I, J, K and L (1989).

WordPerfect for DOS, Version 5.1, Workbook, Lessons 23-24 (1989).

Grosso WE, et. al., "Knowledge Modeling at the Millennium (The Design and Evolution of Protégé-2000)," SMI Report No. SMI-1999-0801 (1999), available at http://smi-web.stanford.edu/ pubs/SMI_Abstract/SMI-1999-0801.html, visited Jan. 1, 2000.

International Committee on Harmonization (ICH), "Structure and Content of Clinical Study Reports," (E3), recommended for adoption at Step 4 on Nov. 30, 1995, www.ich.org (ICH E3).

International Committee on Harmonization (ICH), "Guideline for Good Clinical Practice," (E6, Section 6), recommended for adoption at step 4 May 1, 1996, www.ich.org (ICH E6).

International Classification of Diseases, v.9, Clinical Modification (ICD-9-CM), Sections entitled Preface, Tabular List of Procedures, and Appendix E (2002).

Kahn MG., Using Computable Protocol Models for Interactive Trial Design Optimization & Execution, Abstract and Slides presented at DIA 37th Annual Meeting, Jul. 7-11, 2001, Denver, Colorado.

D. L. Rubin, J. Gennari, & M. A. Musen, "Knowledge Representation and Tool Support for Critiquing Clinical Trial Protocols", Stanford Medical Informatics Report No. SMI-2000-0844, AMIA Annual Symposium, Los Angeles, CA (2000).

D. L. Rubin, J. H. Gennari, S. Srinivas, A. Yuen, H. Kaizer, M. A. Musen, & J. S. Silva, "Tool Support for Authoring Eligibility Criteria for Cancer Trials", Stanford Medical Informatics Report No. SMI-1999-0779. available at http://www-smi.stanford.edu/pubs/SMI_Reports/SMI-1999-0779.pdf, visited Nov. 4, 2003 (1999).

Wampler S. Tackling Protocol Complexity. Good Clinical Practice J 2000;7(2):6-8.

Galluppi G, Rogge M, Roskos L, Lesko L, Green M, Feigal D, et al. Integration of pharmacokinetic and pharmaodynamic studies in the discovery, development, and review of protein therapeutic agents: A conference report. Clin Pharmacol Ther. 2001; 69(6):387-99 (2001).

Holford NH, Kimko HC, Monteleone JP, Peck CC. Simulation of clinical trials. Annu Rev Pharmacol Toxicol 2000;40:209-34 (2000).

Glass HE. Managing clinical investigator costs with benchmarking. Appl Clin Trials 1994: 3 (5): 34-42 (1994).

Kush R. Data standards for clinical development: progress update. Appl Clin Trials 2002; 11 (4): 35-44 (2002).

Manell, Per, "Pharmaceutical Document Management" (presentation slides), PharmaSoft AB, Feb. 12-15, 1995.

DataEdge LLC. Indexes of clinical study complexity, 1993-1999. In: Mathieu MP, editor. Parexel's Pharmaceutical R&D Statistical Sourcebook 2000. Waltham, MA: Parexel International Corp; 2000. p. 66.

DataEdge LLC. Indexes of clinical trial costs per patient, 1993-1999. In: Mathieu MP, editor. Parexel's Pharmaceutical R&D Statistical Sourcebook 2000. Waltham, MA: Parexel International Corp; 2000. p. 67.

Musen MA, Gennari JH, Eriksson H, Tu SW, Puerta AR. Protege-II: Computer support for development of intelligent systems from libraries of components. Medinfo 1995;8(1):766-70.

Kahn MG, Broverman CA, Wu N, Farnsworth WJ, Manlapaz-Espiritu L., "A model-based method for improving protocol quality", Appl Clin Trials 2002;11(5):35-44 (Apr. 2002).

Musen MA, Rohn JA, Fagan LM, & Shortliffe EH, "Knowledge engineering for a clinical trial advice system: Uncovering errors in protocol specification," Report KSL-85-51, Proceedings AAMSI Congress 1986 (Levy, A.H. and Williams, B.T., eds.), pp. 24-27, Anaheim CA, May 1986.

Man, Andrew P., "SGML—The Business Perspective" (presentation slides) Glaxo Research & Development Ltd., Feb. 12-15, 1995.

Schmuff, Norman R., "The Standards—Based CMC Canda Project—Background" (presentation slides), Food and Drug Administration, Feb. 14-15, 1994.

Hampshire, N., "dbPublisher," EXE 4(4) (Sep. 1989) pp. 24 et. seq. "Black and Veatch selects Documentum as corporate document management standard; largest U.S. engineering and design firm implements Documentum to increase competitive advantage in worldwide market," Business Wire, p. 12061100, Dec. 6, 1994.

Walter, M., "Documentum: open approach to automating workflow and management of long documents," Seybold Report on Publishing Systems 23(7), p. 3(11), Dec. 1, 1993.

Pallatto, J., "Software design tool gets new module," PC Week 5(41) (Oct. 10, 1988) 24.

Schettini, S., et al., "SGML is Here to Stay," Publish. 9(6) (Jun. 1994) 71-78.

Dyson, E., "SFQL: When Structure Counts," RElease 1.0 91(4) (Apr. 1991) 14(5).

"SGML Primer What Every Software Company Should Know about SGML," RElease 1.0, 91(7) (Jul. 1991) 7(7).

"Accurate Information & Ontos," RElease 1.0, 91(7) (Jul. 1991) 23(2).

Seymour, J., "Forms Software: Next Hot Category," PC Magazine 7(16) (Sep. 1988) 77(2).

Brenesal, B., "Q&A 4.0: the tradition continues," PC Sources 2(10) (Oct. 1991) 361.

Kitney, R.I. et al., "Clinical trials of an electronic medical record system," Computers in Cardiology, Cleveland, OH, Sep. 13-16, 1998, IEEE, 201-204.

Fridsma, Douglas B., et al. "Representing Medical Protocols for Organizational Simulation: An Information Processing Approach" J. Computational & Mathematical Org. Theory 4(1): 71-95 (1998).

Spilker, Bert, "Guide to Clinical Trials" pp. vii-xv, 7-26, 78-84, 482-489, 953-960 (1991).

Kuhn & Roughton, "Now Securing Every Row", Oracle Magazine, Jul./Aug. 2003, available at http://otn.oracle.com/oramag/oracle/03-jul/043security.htrnl, visited Aug. 7, 2003.

Domain Pharma, "Clintrial 4"—Setting Up Clintrial, Release 4.2, 1999, pp. 1-478.

Domain Pharma, "Clintrial 4"—Working with Review, Release 4.2, 1999, pp. 1-532.

Domain Pharma, "Clintrial 4"—Entering, Editing and Retreiving Data, Release 4.2, 1999, pp. 1-366.

Domain Pharma, "Clintrial 4"—Managing Data, Release 4.2, 1999, pp. 1-352.

Domain Pharma, "Clintrial 4", Working with Multisite, Release 4.2, 1999, pp. 1-204.

Domain Pharma, "Clintrial 4", Reference Guide, Release 4.2, 1999, pp. 1-380.

Domain Pharma, Clintrial Database Schema, Version 4.2, Modified: Nov. 6, 1998.

Matoren, Gary M., "The Clinical Research Process in the Pharmaceutical Industry", New York: Marcel Dekker, Inc., Chapters 8, 9 and 11, (1984).

Centerwatch.com, "Glossary", available http://www.centerwatch.com/patient/glossary.html (visited Dec. 8, 2003).

FDA, Guidance for Industry E6 Good Clinical Practice: Consolidated Guidance, ICH, (Apr. 1996).

"Documentum Market Application Profile" (advertisement), Documentum, Inc. (1995).

"Decision support for clinical trial eligibility determination in breast cancer," L. Ohno-Machado, S. J. Wang, A.A. Boxwala, Proc. AMIA Symposium, 1999.

"EON: A component-based approach to automation of protocol-directed therapy," M.A. Musen, S.W. Tu, A.K. Das, Y. Shahar, J. Am. Med. Inform. Assoc., 1996.

"Unitized data system: A new formalism for encoding and presenting data from the scientific research literature," D.P. Fan, J.M. Curtsinger, L. Johnson, S. Kalkhar, Journal of the American Society for Information Science, 1992.

"ICH Harmonised Tripartite Guideline: General Considerations for Clinical Trials," International Conf. on Harmonisation of Technical Requirements for Registration of Pharmaceuticals for Human User recommended for adoption on Jul. 17, 1997, URL: www.ifpma.org/ich5e.html, Accessed: Aug. 31, 2001.

Kroll, J.A., De Bruin, A., Getz K., Eschmann K., and Zisson, S., "Study Conduct Delays are Getting Worse," In: Kroll JA, editor. An Industry in Evolution, Second ed., Boston, MA: CenterWatch; 1999, p. 99.

Musen M.A., "Domain Ontologies in Software Engineering: Use of Protege with the EON Architecture," Methods of Information in Medicine, F.K. Schattauer Verlagsgesellschaft mbH (1998); 37:540-50.

Sheiner L.B. and Steimer J.L., "Pharmacokinetic/Pharmacodynamic Modeling in Drug Development," Annu. Rev. Pharmacol. Toxicol. 2000. 40:67-95, 2000, Annual Reviews.

Brown, S., U.S. Appl. No. 09/201,323, filed Oct. 10, 2001, entitled "Leveraging Interaction with a Community of Individuals," 84 pgs.

Office action mailed Oct. 18, 2005 in U.S. Appl. No. 09/974,781.

Response a mailed Apr. 12, 2006 in reply to office action mailed Oct. 18, 2005 in U.S. Appl. No. 09/974,781.

Office action mailed Aug. 16, 2006 in U.S. Appl. No. 09/974,781.

Response B under 37 CFR 1.116 mailed Oct. 13, 2006 in reply to office action mailed Aug. 16, 2006 in U.S. Appl. No. 09/974,781.

Advisory action mailed Nov. 3, 2006 in U.S. Appl. No. 09/974,781.

Response C filed Dec. 11, 2006 in reply to office action mailed Aug. 16, 2006 in U.S. Appl. No. 09/974,781.

Office action mailed Mar. 7, 2007 in U.S. Appl. No. 09/974,781.

Response D filed Sep. 7, 2007 in reply to office action mailed Mar. 7, 2007 in U.S. Appl. No. 09/974,781.

Notice of Appeal and Pre-Appeal Brief Request for Review filed Sep. 7, 2007 in reply to office action mailed Mar. 7, 2007 in U.S. Appl. No. 09/974,781.

Decision of Panel to repoen prosecution mailed Mar. 4, 2008 in response to Pre-Appeal Brief Request for Review filed Sep. 7, 2007 in U.S. Appl. No. 09/974,781.

Advisory action mailed Mar. 4, 2008 in reply to Response D filed Sep. 7, 2007 in U.S. Appl. No. 09/974,781.

Notice of Allowance and Fees Due mailed Jun. 24, 2008 in U.S. Appl. No. 09/974,781.

Comment on Statement of Reasons for Allowance filed Sep. 19, 2008 in U.S. Appl. No. 09/974,781.

* cited by examiner cancer_protocols_INSTANCE_00039 [instance of Cancer_Clinical_Protocol]

Label
CALGB 49802

Version
mgk 25Jan00

Title
Phase III Study of Adriamycin/Taxotere vs Adriamycin/Cytoxan for the Adjuvant treatment of Node Positive or High Risk Node Negative Breast Cancer

Authors
M.G. Public

Clinical Algorithm
CALGB 49802 Level 1

Reference
◆ MUSC PRN web page

Context Reference

Entry Criteria (1 values)

Protocol Name
CALGB 49802

Clinical State Name

Inclusion List
◆ Histologically or cytologically confirmed invasive breast cancer
◆ 1-3 histologically involved axillary lymph nodes
◆ No evidence of metastatic disease (M0)
◆ Absolute neutrophil count of at least 1,500/mm3
◆ Platelet count of at least 100,000/mm3
◆ Left ventricular ejection fraction at rest at least 45% by MUGA
◆ Bilirubin no greater that 1.2 times upper limit of normal (ULN)
◆ Age 18-70
◆ Effective contraception required of fertile women
◆ No prior chemotherapy
◆ No prior radiotherapy
◆ No concurrent estrogen therapy

210

Exclusion List
◆ Tumor of any size with direct extension to chest wall or skin (T4)
◆ Patient is pregnant or nursing

| mgk_cancer_protocols_INSTANCE_00063 [instance of Consultation_Act... | | |
|---|---|---|
| Label | mgk_cancer_protocols_INSTANCE_00063 [instance of Consu | |
| CALGB 49802: Collect Stratification Variabl | ◆ Evaluate lymph node status<br>◆ Evaluate menopausal status<br>◆ Evaluate estrogen receptor status<br>◆ Evaluate progesterone receptor status | |
| Followed By [V][C][+][-] | | |
| Rule In [V][C][+][-] | References [V][C][+][-] | |
| Rule Out [V][C][+][-] | | |

Fig. 5

| | |
|---|---|
| ProtocolTitle | Version |
| A Phase III Study of Paclitaxel via Weekly 1-Hour Infusion v | Update #1 |
| ProtocolIdentifier | VersionDate |
| CALGB 9840 | December 15, 1998 |
| OfficialSourceDocument | |
| http://prn.musc.edu/research/protocol/deptmed/divhonc/br | EligibilityCriteriaSet [V][C][+][-] |
| ShortDescription | ◆ CALGB 9840 Eligibility Criteria — 1212 |
| CALGB 9840 | |
| StudyChair | |
| Andrew D. Seidman, M.D. | |
| Sponsor | |
| CALGB | LongDescription |
| QuickScreenCriterion (1210) | |
| Breast Cancer ▼ | |
| Sponsor | |
| To compare "standard" (S) paclitaxel at 175 mg/m2 via 3-hour infusion every 3 weeks to "dose-dense" (DD) paclitaxel at 80 mg/m2 via 1-hour infusion every week | FirstVisit [V][C][+][-] |
| | Screening Visit |
| TrialStatus / AccrualStatus | |
| Active ▼ / Open for accrual ▼ | ProtocolSchemaDiagram [V][C][+][-] |
| TrialPhase / TrialType | CALGB 9840 Schema 1214 |
| Phase III ▼ / Cooperative group ▼ | |

FastTrack Protocol_INSTANCE_00206 [Instance of ManagementTask]

ShortDescription

Give Arm A Paclitaxel treatment

LongDescription

Give Paclitaxel 175 mg/m2 IV, 3hours. This treatment is given to patients in Arm A of the CALGB 9840 protocol. It is given once every 3 weeks. One cycle is equivalent to one infusion. Granulocyte count must be >= 1500/ul and platelet count must be >= 100,000 / ul on day 1 of each cycle in order to proceed with the Paclitaxel infusion. Patients must receive the pre-medication prior to Paclitaxel infusion. If either the granulocyte or platelet count are not adequate, do not continue with treatment. Patients should receive a minimum of 2 cycles unless there is rapid disease progression.

Expected toxicities:

The dose-limiting toxicity of Paclitaxel is neutropenia. Other known toxicities include nausea and vomiting, diarrhea, stomatitis, mucositis, pharyngitis, typhlitis, ischemic colitis, bradycardia, atrial arrhythmia, hypotension, hypertension, sensory (taste), peripheral neuropathy, seizures, mood, hepatic encephalopathy, acute anaphylactoid and urticarial reactions, flushing, rash, pruritis, increased SGOT, SGPT, bilirubin and/or alkaline phosphatase, hepatic failure, hepatic necrosis, alopecia, fatigue, arthralgia, myalgia, light-headedness, myopathy, visual changes (sensation of flashing lights, blurred vision). Local infiltration with Paclitaxel will cause mild local symptoms (erythema, discomfort, induration) that usually resolve within a week. If infiltration occurs, there is the rare possibility of ulceration or rash. Seizure have been reported rarely in association with Paclitaxel use.

Dose Modifications:

Allergic reactions: Patients with grade 1 or 2 allergic reactions may have treatment continued without modifications. Patients with grade 3 or 4 allergic reactions who are responding to treatment may remain on protocol therapy after discussion with Study Chair. Such patients are at risk for recurrent allergic reactions. As a first maneuver, retreatment after premedication with oral recurrent allergic reactions. As a first maneuver, retreatment after premedication with oral dexamethasone 20 mg at 12 and 6 hours pre-administration of Paclitaxel, along with IV H1 and H2- receptor antagonist should be attempted. If necessary, thereafter, infusion rate adjustments will be considered and additional premedications will be administered. These patients must be informed of the potential risks of recurrent allergic reactions and must be carefully monitored.

Hematologic Toxicity: Patients are to be managed as clinically indicated. Colony stimulation factors (G-CSF) should be used in the manner

SiteLongDescription

FastTrack Protocol_INSTANCE_00196 [instance of ManagementTask]

ShortDescription

Submit Form C-116

LongDescription

Submit CALGB Advanced Breast Cancer Followup-form (C-116) every two cycles while on protocol therapy, at 6 & 12 months after end of treatment, at disease progression or initiation of non-protocol therapy.

SiteLongDescription

SiteShortDescription

| FastTrack Protocol INSTANCE-00023 [Instance of VisitToVisitTransition] |

ShortDescription
Arm A Treatment to Arm A Treatment Retry #

PrefrerredRelativeTime
7

First Object | V | C | + | − |
Arm A Treatment Visit

MaximumRelativeTime
7

Second Object | V | C | + | − |
Arm A Treatment Retry #1

MinimumRelativeTime
7

LongDescription
If either granulocyte or platelet count are not adequate, blood counts should be repeated weekly and treatment should be instituted when there has been hematologic recovery. Patients receiving G-CSF are not eligible for re-treatment unless they have been off G-CSF for a minimum of 24 hours.

SiteLongDescription

☑ IsPreferredTransition — 2310

SiteShortDescription

Fig. 23

|  | Pre-Treatment | | Treatment | | | | | Follow up | | | Discontinued[1] | Withdrawal From Study[2] |
|---|---|---|---|---|---|---|---|---|---|---|---|---|
|  | | | | | | | | Monitoring | | Final F/U | | |
| Study Timepoint | Scrn | BL | V1 (+/-2 d) | V2 (+/-6 h) | V3 (+/-6 h) | V4 (+/-6 h) | V5 (+/-6 h) | V6 (+/-1 h) | V7 (+/-1 h) | F/U (+/-1 d) | D/C | Withdrawal |
|  |  | Day 0 | Day 1 | Day 2 | Day 3 | Day 4 | Day 5 | Day 6 | Day 7 | Day 28 |  |  |
| Medical History |  | X |  |  |  |  |  |  |  |  |  |  |
| Neurological Exam |  | X |  |  |  |  |  |  |  |  |  |  |
| NIHSS |  | X |  |  |  |  |  |  |  |  |  |  |
| Modified Rankin Scale (mRS) |  | X |  |  |  |  |  |  |  |  |  |  |
| Lab profile |  |  |  |  |  |  |  |  |  |  |  |  |
| Rectal Temperature[3] | X |  | X[4] | X | X | X | X |  |  |  |  |  |
| Dosing |  |  | X | X | X | X | X |  |  |  |  |  |
| Barthel Index (BI) |  |  |  |  |  |  |  |  |  |  |  |  |
| Adverse Event Capture |  |  | X | X | X | X | X | X | X | X |  |  |
| Brain CT | X |  |  |  |  |  |  |  |  |  | X |  |

1 Subject to meeting criteria for discontinuation of the study drug.
2 Subject to meeting the criteria for withdrawing from the study.
3 Measure in both ears.
4 Measure every 2 hours after the start of treatment for the first 24 hours.

Fig. 45

Period: Pre-Treatment
The screening activities must conclude within 1 day of baseline measurements.
- Visit: Screening
    - Rectal Temperature . Personnel: This task should be performed by the Nurse
    - Brain CT . Personnel: This task should be performed by the CT Technician
- Visit: Baseline (Day 0 )
    - Medical History . Personnel: This task should be performed by the Investigator
    - Neurological Exam . Personnel: This task should be performed by the Investigator
    - NIHSS . Personnel: This task should be performed by the Investigator
    - Modified Rankin Scale (mRS) . Personnel: This task should be performed by the Investigator
    - Rectal Temperature . Personnel: This task should be performed by the Nurse
    - Adverse Event Capture Period: Treatment (Duration is 7 days )
The treatment period should begin within 24 hours of conclusion of baseline measurements
- Visit: Visit 1 (Day 1 ) (+/-2 d ) viit one detail for you
    - Rectal Temperature . Personnel: This task should be performed by the Nurse
    - Dosing . Personnel: This task should be performed by the Nurse
    - Adverse Event Capture
- Visit: Visit 2 (Day 2 ) (+/-6 h )
    - Rectal Temperature . Personnel: This task should be performed by the Nurse
    - Dosing . Personnel: This task should be performed by the Nurse
    - Adverse Event Capture
- Visit: Visit 3 (Day 3 ) (+/-6 h )
    - Rectal Temperature . Personnel: This task should be performed by the Nurse
    - Dosing . Personnel: This task should be performed by the Nurse
    - Adverse Event Capture
- Visit: Visit 4 (Day 4 ) (+/-6 h )
    - Rectal Temperature . Personnel: This task should be performed by the Nurse
    - Dosing . Personnel: This task should be performed by the Nurse
    - Adverse Event Capture
- Visit: Visit 5 (Day 5 ) (+/-6 h ) I entered something for visit 5
    - Rectal Temperature . Personnel: This task should be performed by the Nurse
    - Dosing . Personnel: This task should be performed by the Nurse
    - Adverse Event Capture Period: Follow up (Duration is 1 year )
Follow up is optional.
- Subperiod: Monitoring
    - Visit: Monitoring 1 (Day 6 ) (+/-1 h )
        - Adverse Event Capture
    - Visit: Monitoring 2 (Day 7 ) (+/-1 h )
        - Adverse Event Capture
- Subperiod: Final F/U
    - Visit: Follow up visit (Day 28 ) (+/-1 d )
        - Modified Rankin Scale (mRS) . Personnel: This task should be performed by the Investigator
        - Barthel Index (BI) . Personnel: This task should be performed by the Investigator Period: Discontinued
- Visit: Discontinuation
    - Adverse Event Capture Period: Withdrawal From Study
Subject withdraws from the study entirely in certain situations
- Visit: Withdrawal from Study

Fig. 46

ASSISTANCE FOR CLINICAL TRIAL PROTOCOLS

REFERENCE TO COMPUTER PROGRAM LISTING AND TABLE APPENDICES

Computer program listings and Table appendides comprising duplicate copies of a compact disc, named "FSTK-1006-CPLA," accompany this application and are incorporated by reference. The discs are in IBM-PC/MS-Windows format. The appendices include the following files:

| | | |
|---|---|---|
| design.xsd.txt | 8K bytes | created May 28, 2003 |
| echooser.xsd.txt | 6K bytes | created May 28, 2003 |
| POCCore.xslt.txt | 27K bytes | created May 28, 2003 |
| SampleInstance.xml.txt | 61K bytes | created May 28, 2003 |
| SampleMapper.xml.txt | 67K bytes | created May 28, 2003 |
| schedule.xsd.txt | 8K bytes | created May 28, 2003 |

COPYRIGHT DISCLAIMER

A portion of the disclosure of this patent document contains material which is subject to copyright protection. The copyright owner has no objection to the facsimile reproduction by anyone of the patent document or the patent disclosure as it appears in the U.S. Patent and Trademark Office patent file or records, but otherwise reserves all copyright rights whatsoever.

BACKGROUND

1. Field of the Invention

The invention relates to the development of clinical trial protocols, and more particularly to computer-assisted methodologies and structures for cost-effective, historically informed development of clinical trial protocols with reduced likelihood of operational uncertainties.

2. Description of Related Art

Clinical trial protocols are designed to produce scientifically sound new knowledge about the safety, efficacy or specific therapeutic characteristics of a new drug or treatment combination. Clinical trial protocols developed using modern study design principles have well-understood statistical hypothesis testing and internal validity characteristics. Thus, modern clinical studies are designed to deliver the most supportable scientific knowledge with the smallest number of study subjects. Despite these more efficient study designs, the complexity and associated costs of executing new protocols continue to increase.

The rising complexity of current protocol designs has resulted in a dramatic increase in the operational management overhead required to initiate, execute, and complete a clinical trial successfully within budget and time frame. With the increasing number of patients, investigators, locations, and countries involved in a given trial, it is not surprising that many clinical trials have significant operational issues that cause substantial cost/time over-runs or outright trial failures.

A distinction between scientific versus operational issues in clinical trials planning and execution is important. A scientific issue arises due to the limited state of current knowledge about the trial agent(s) pharmacologic and therapeutic properties in the experimental clinical situation. This lack of scientific knowledge is precisely the reason a well-designed clinical trial is required. Scientific issues are ethically justified and do not indicate any problem with the clinical trial protocol. Operational issues arise because of unforeseen difficulties in executing the trial within the strict parameters or assumptions embedded implicitly or explicitly within the protocol design. In this case, the protocol designers may not have been cognizant of the difficulties the field organization or clinical investigators may have in operationalizing specific study design components.

Operational deficiencies can be costly to an organization, especially if they require an amendment to the protocol during execution of the trial. Even simple amendments have substantial costs, including the internal overhead of detecting the need for an amendment, costs for creating the amendment, internal approvals costs for releasing the amendment, costs for disseminating the amendment and the follow-up effort to ensure that the amendment has been incorporated into the clinical trials process at a potentially large number of the trial sites. The cost of an amendment also includes the opportunity costs due to study completion delays or data analysis impact due to inconsistent operational behavior at the trial sites.

Amendments are only the most visible and more costly manifestation of a spectrum of ways in which operational deficiencies can impact an organization. A large number of operational issues are handled via formal and informal communications between study project managers and clinical trials sites. Thus the volume of faxes and telephone calls can be another "cost" which directly affects team productivity and trial site performance but is not as visible as a trial amendment.

At most large clinical development organizations, concern about protocol design quality has spawned the creation of Protocol Review Committees (PRCs). Although specifics vary widely, the role of the PRC is to provide a centralized resource for the critical examination of a proposed protocol in a "near-final" form. Unlike Institutional Review Boards who are concerned about patient safety, risk/benefit and informed consent, the focus of the PRC is on scientific merit, study validity, and the appropriate use of scarce clinical development resources. Many PRCs include representatives from clinical operations and a few include clinical trial sites so that the operational issues that may be embedded within or implied by a proposed trial design can be examined.

Many organizations that have implemented PRCs now require every protocol to be reviewed and approved by the committee prior to its release to the clinical operations team for field deployment. In addition, many PRC members state that a review by the committee often results in substantial changes to the original protocol. Protocol Review Committees bring together substantial skills and corporate institutional experience, representing an enormous investment of highly trained personnel. For the organizations that have committed to this approach, this investment is deemed to be justifiable, given the high stakes and resources committed to the execution and success of each trial.

PRC reviews do seem to have a positive contribution to the operational quality of reviewed protocols. But the cost of such reviews is large. PRCs generally require highly trained, expensive senior people to perform time-consuming, detailed review of every protocol prior to internal approval. The man-hours consumed in analyzing a proposed protocol, discussing the findings at a PRC meeting, presenting the findings to the protocol author and then repeating the process in a limited manner after the protocol is revised represent a huge hidden cost. As PRC members leave or rotate, the quality and quantity of protocols reviewed by the PRC may vary widely. Thus, while PRC reviews may be effective, they are neither scalable nor repeatable.

In addition to or instead of forming Protocol Review Committees, many organizations have instituted other methods for improving the quality of the protocol during its initial creation. Templates, checklists, and previously approved protocols are common materials provided to protocol authors to assist with the improvement of the quality of their initial protocol designs. These methods have numerous drawbacks, however, that significantly limit their usefulness. First, most paper-based methods are static. That is, these methods are not easily updated, disseminated, and then incorporated into the protocol writer's daily routine. Thus, it is often the case that protocols developed with these tools continue to make the same operational mistakes long after the organization has updated the reference materials.

Second, as people leave the organization, the institutional knowledge of what makes a protocol "work" within that organization is lost. If the employee was a member of the Protocol Review Committee, this toss of institutional knowledge is even more extensive, impacting the entire range of protocols reviewed by the PRC.

Third, organizational mergers and alliances result in widely disparate approaches, assumptions, and standard operating procedures for designing protocols. Operational knowledge unique to one organization or to a specific therapeutic area tends to remain within the original organization or therapeutic area and therefore not benefit the combined organization. Hard-earned (and expensive) experience-based knowledge diffusion occurs only if and when people from one organization migrate into similar positions within the second organization. Of course, this migration results in the loss of operational knowledge from the original clinical operations group.

Accordingly, there is an urgent need for a methodology and tools that will assist in the design of clinical trial protocols in a cost-effective manner, taking advantage of knowledge built into previous protocols even where the designers of such protocols are no longer available. The methodology should assist in avoiding operational uncertainties early, before a clinical trial begins according to the protocol.

SUMMARY OF THE INVENTION

The invention involves methods and tools for electronically assisting in the design of clinical trial protocols. In an embodiment, the invention can take advantage of Intelligent Clinical Protocol (iCP) database methodologies, in which clinical trial protocol features are represented in a machine readable data structure that then can be used to drive the operation of most aspects of the study. Roughly described, according to the invention, a user creates one or more document models which formally describe the structure of a corresponding human-readable document that will be an ultimate product of the protocol design process. The document model, referred to herein as an Intelligent Clinical Document (iCD) model, can include pre-specified fields, and variable fields that are to be rendered from data in the iCP database. The document ultimately created is an instance of the iCD model. The designer then uses a protocol design tool through which he or she designs the protocol, instantiating and drawing from iCP objects as necessary. The protocol design tool can render newly entered iCP data into an iCD instance dynamically and consistently in all the places in the document at which the data is required. The protocol design tool also can suggest specific tasks that the designer might want to include in the protocol, based on a historical database of tasks that were associated with previous clinical trial protocols. The protocol design tool also can automatically and dynamically calculate approximate per-patient costs, based on a historical database of the cost of individual tasks that the designer has linked into each patient contact event, and can automatically provide advisories indicating aspects of the document that either still require completion in order to avoid operational uncertainties, or must be modified in order to satisfy a set of rules that have been established for the current document type.

The iCP database into which the protocol design tool encodes features of a protocol, is a highly structured, formal model of a clinical protocol. In a preferred embodiment, the iCP database has been designed specifically to capture issues that tend to cause operational difficulties, and may also be designed to capture other issues that the study sponsor design group or other controlling organization deems important for other reasons. With properly declared organization-specific preferences for characteristics of iCP elements, along with an organizationally-specified iCD model, the process can avoid the omission of specific parameters, and avoid any ambiguities or vagueness in specific parameters, thereby avoiding operational uncertainties that can adversely impact the progress of the study. In an aspect of the invention, the protocol design tool takes advantage of the model formality by identifying and reporting, at any time during the protocol design process, any of a variety of kinds of operational uncertainties and rule violations for the document type, still present in the iCP contents or the document being created.

BRIEF DESCRIPTION OF THE DRAWINGS

The invention will be described with respect to specific embodiments thereof, and reference will be made to the drawings, in which:

FIGS. 2-8 are screen shots of an example for an Intelligent Clinical Protocol (iCP) database.

FIGS. 11, 12 and 17-25 are screen shots of screens produced by Protégé 2000, and help illustrate the relationship between a protocol meta-model and an example individual clinical trial protocol.

FIG. 45 is an image of a sample schedule of activities table produced in accordance with a dynamic template.

FIG. 46 is an image of a sample SOA narrative produced in accordance with another dynamic template.

DETAILED DESCRIPTION

Intelligent Clinical Protocol

Figure 1:
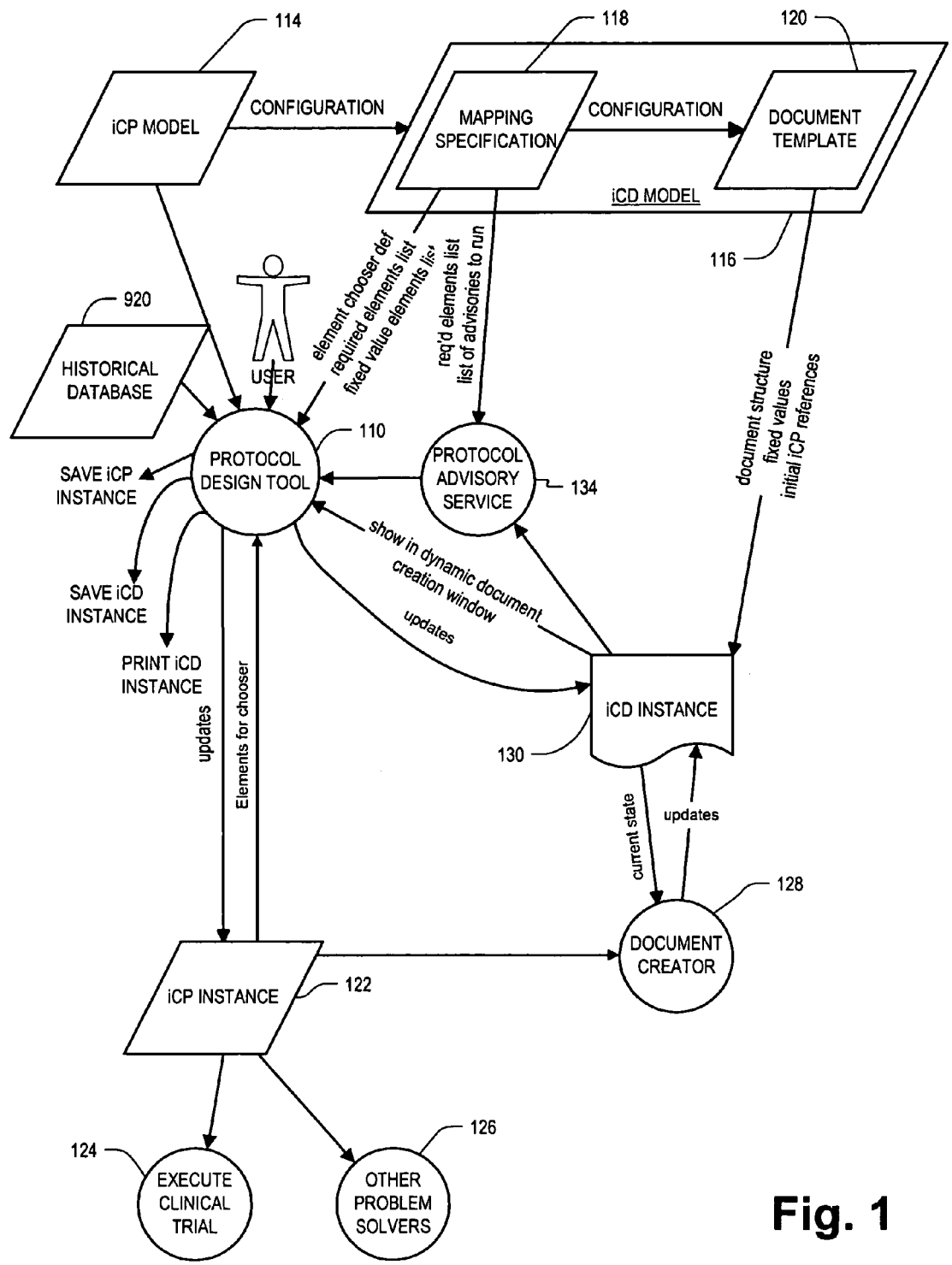
FIG. 1 is an overall functional diagram of an embodiment of a system according to the invention.

In PCT publication No. WO01/93178A2, incorporated by reference herein, there is described a system which defines; manages and evaluates clinical trial protocols in an overall end-to-end manner. The system starts with the creation of protocol meta-models by a central authority, and ends with the conduct of trials by clinical sites, who then report back electronically for near-real-time monitoring by the sponsor's clinical operations team and for analysis by the central authority. The central authority first creates protocol meta-models, one for each of several different disease categories, and makes them available to protocol designers. The protocol designer chooses the meta-model appropriate for the relevant disease category, and encodes the clinical trial protocol within the selected meta-model. The resulting protocol database is referred to herein as an Intelligent Clinical Protocol (iCP), which is an instance of the protocol meta-model, and the iCP can be used to drive all downstream problem solvers including a problem solver that indicates to the clinician at a study site exactly what tasks are to be performed at each patient visit. These tasks can include both patient management tasks, such as administering a drug or taking a measurement, and also data management tasks, such as completing and submitting a particular case report form (CRF). The workflow graph embedded in the protocol database advantageously also instructs the proper time for the clinician to obtain informed consent from a patient during the eligibility screening process, and when to perform future tasks, such as the acceptable date range for the next patient visit. The iCP database is a highly structured, formal model that can be used to help identify any operational uncertainties and other potential issues contained in the clinical trial protocol.

In one embodiment, the protocol meta-models are created using a meta-model authoring tool. Protégé 2000 is an example of a tool that can be used as a meta-model authoring tool. Protégé 2000 is described in a number of publications including William E. Grosso, et. al., "Knowledge Modeling at the Millennium (The Design and Evolution of Protégé-2000)," SMI Report Number: SMI-1999-0801 (1999), available at http://smi-web.stanford.edu/pubs/SMI_Abstracts/SMI-1999-0801.html, visited Jan. 1, 2000, incorporated by reference herein. In brief summary, Protégé 2000 is a tool that helps users build other tools that are custom-tailored to assist with knowledge-acquisition for expert systems in specific application areas. It allows a user to define "generic ontologies" for different categories of endeavor, and then to define "domain-specific ontologies" for the application of the generic ontology to more specific situations. In many ways, Protégé 2000 assumes that the different generic ontologies differ from each other by major categories of medical endeavors (such as medical diagnosis versus clinical trials), and the domain-specific ontologies differ from each other by disease category. In the present embodiment, however, all ontologies are within the category of medical endeavor known as clinical trials and protocols. The different generic ontologies correspond to different meta-models, which differ from each other by disease category. In this sense, the generic ontologies produced by Protégé in the present embodiment are directed to a much more specific domain than those produced in other applications of Protégé 2000.

Since the meta-models include numerous building blocks as well as many options for patient eligibility criteria, a wide variety of different kinds of clinical trial protocols, both simple and complex, can be designed. These meta-models are provided to clinical trial protocol designers who use them to encode individual clinical trial protocols. In one embodiment the designer can again use Protégé 2000 to encode the protocol, but in a preferred embodiment the designer uses the protocol design tool described herein.

Conceptually, an iCP database is a computerized data structure that encodes most significant operational aspects of a clinical protocol. In an embodiment, this includes objectives and outcomes, eligibility criteria, administrative parameters, the study schedule including study visits and tasks performed during those visits, design parameters, justification for tasks included during the protocol, statistical elements, and study planned metrics. In the embodiments described herein, the iCP is an object-oriented database, and can be represented in an XML format. But databases deriving from other database paradigms (such as a relational database) also can be used. The iCP structure can be readily extended to encompass new concepts, new drugs, and new testing procedures as required by new drugs and protocols. The iCP database is used by most software modules in the overall system to ensure that all protocol parameters, treatment decisions, and testing procedures are captured, kept consistent, and re-used.

Thus the iCP database provides a comprehensive model of a clinical protocol so as to support consistent tools created for problems such as accrual, patient screening and workflow management. By using a comprehensive model and a unifying standard vocabulary, all tools behave according to the same shared set of protocol specifications.

As used herein, the term "database" does not necessarily imply any unity of structure. For example, two or more separate databases, when considered together, still constitute a "database" as that term is used herein. The iCP is an example of a structured protocol modeling database. As used herein, a database is "structured" if it contains sections (such as fields, objects, files, columns, rows or tagged sections) that are related to each other in accordance with rules that are expected or enforced by one or more external applications. In this sense a structured database differs from a typical word processing document because the word processing document lacks an externally enforced structure. Most databases are structured.

The iCP data structures can be used by multiple tools to ensure that the tool performs in strict compliance with the clinical protocol requirements. For example, a patient recruitment simulation tool can use the eligibility criteria encoded into an iCP data structure, and a workflow management tool uses the visit-specific task guidelines and data capture requirements encoded into the iCP data structure. The behavior of all such tools will be consistent with the protocol because they all use the same iCP database.

The iCP database is used to drive all downstream "problem solvers" such as electronic CRF generators, and assures that those applications are revised automatically as the protocol changes. This assures protocol compliance. The protocol design tool described herein draws on external knowledge bases to help trial designers, including the suggestion of individual tasks that might be appropriate for the particular indication and trial phase targeted by the current protocol, and including cost data to allow designers to choose less costly but equally effective tasks where possible. The use of such external knowledge bases helps save protocol design time and cost, and helps to enable a clinical trial protocol design process that is more akin to customization than to the current "every trial unique" model.

Figure 11:
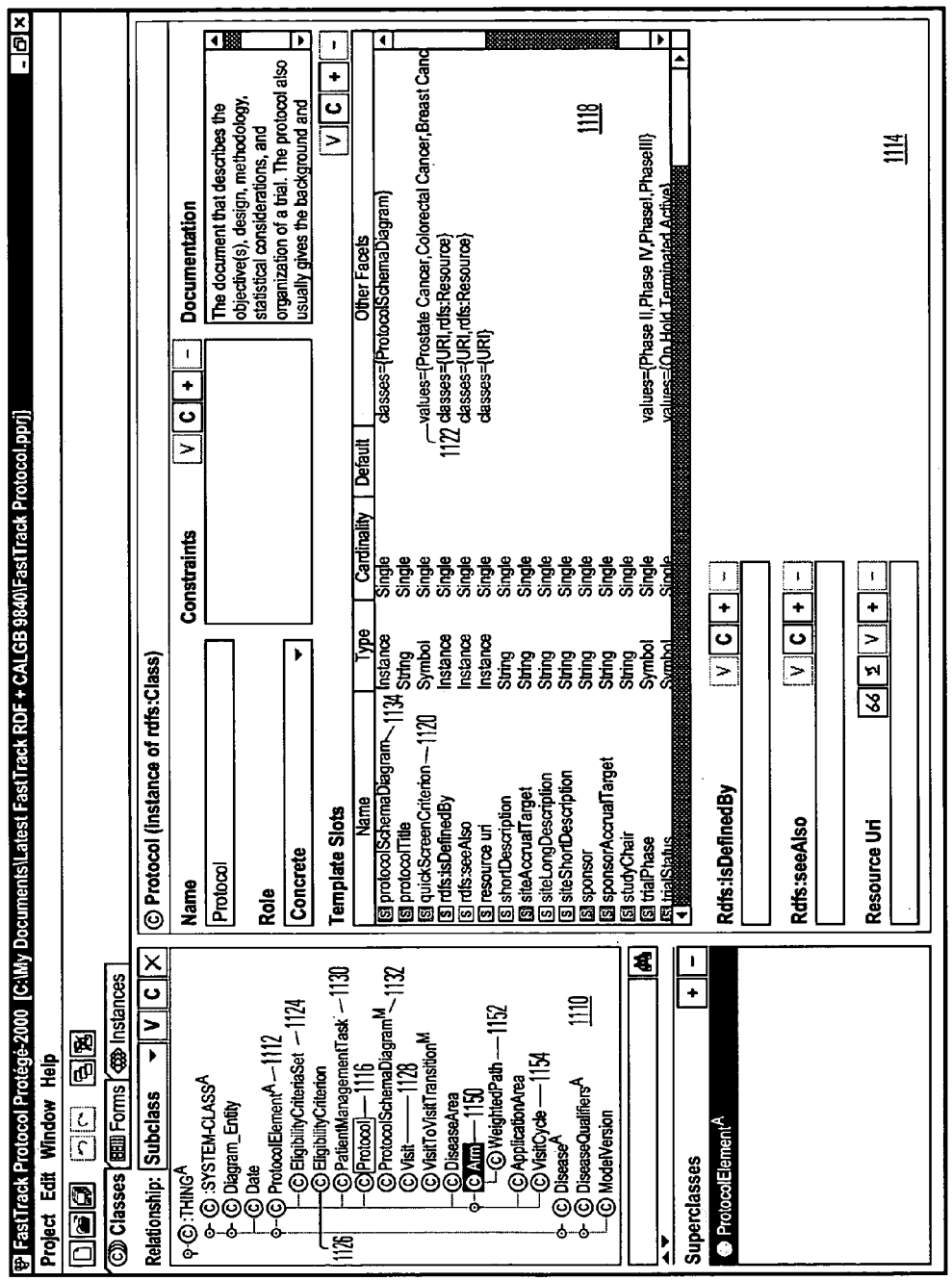

In order to better understand the structure and content of an iCP embodiment, screen shots of screens produced by the modeling and knowledge acquisition tool Protégé 2000 will be used. As mentioned, the designer could use Protégé 2000 to encode the protocol directly, but this would bypass some of the features and advantages of the present invention. FIG. 11 is a screen shot illustrating the overall class structure in the left-hand pane 1110. Of particular interest to the present discussion is the class 1112, called "FastTrackClass," also often referred to herein as the ProtocolElement class), and the classes under class 1112. ProtocolElement 1112 and those below it represent an example of a protocol meta-model. This particular meta-model is not specific to a single disease category.

The right-hand pane 1114 of the screen shot of FIG. 11 sets forth the various slots that have been established for a selected one of the classes in the left-hand pane 1110. In the image of FIG. 11, the "protocol" class 1116, a subclass of ProtocolElement 1112, has been selected (as indicated by the border). In the right-hand pane 1114, specifically in the window 1118, the individual slots for protocol class 1116 are shown. Only some of the slots are pertinent to the present discussion; those not discussed herein are not important for an understanding of the invention. It can be seen that several of the slots in the window 1118 contain "facets" which, for some slots, define a limited set of "values" that can be stored in the particular slot. For example, the slot "quickScreenCriterion" 1120 can take on only the specific values "prostate cancer," "colorectal cancer," "breast cancer," etc.

FIG. 12 is a screen shot of a particular instance of class "protocol" in FIG. 11, specifically a protocol object having identifier CALGB 9840. It can be seen that each of the slots defined for protocol class 1116 has been filled in with specific values in the protocol class object instance of FIG. 12. Whereas FIG. 11 illustrates an aspect of a clinical trial protocol meta-model, FIG. 12 illustrates the top-level object of an example iCP designated CALGB 9840. For example, it can be seen that for the iCP CALGB 9840, the slot "quickScreenCriterion" 1120 (FIG. 11) has been filled in by the protocol designer as "Breast Cancer" (item 1210 in FIG. 12), which is one of the available values 1122 for the quickScreenCriterion slot 1120 in FIG. 11. In addition, the protocol designer has also filled in "CALGB 9840 Eligibility Criteria", an instance of EligibilityCriteriaSet class 1124, for an EligibilityCriteriaSet slot (not shown in FIG. 11) of the protocol class object. Essentially, therefore, the protocol class object of FIG. 12 includes a pointer to another object identifying the "further eligibility criteria" for iCP CALGB 9840.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. Similarly, when a data object is said to "describe" an aspect of the protocol, there is no requirement that the entire description be self-contained within the data object. For example, part of the description can be physically located elsewhere, and merely be either explicitly or implicitly associated with the data object.

Figure 17:
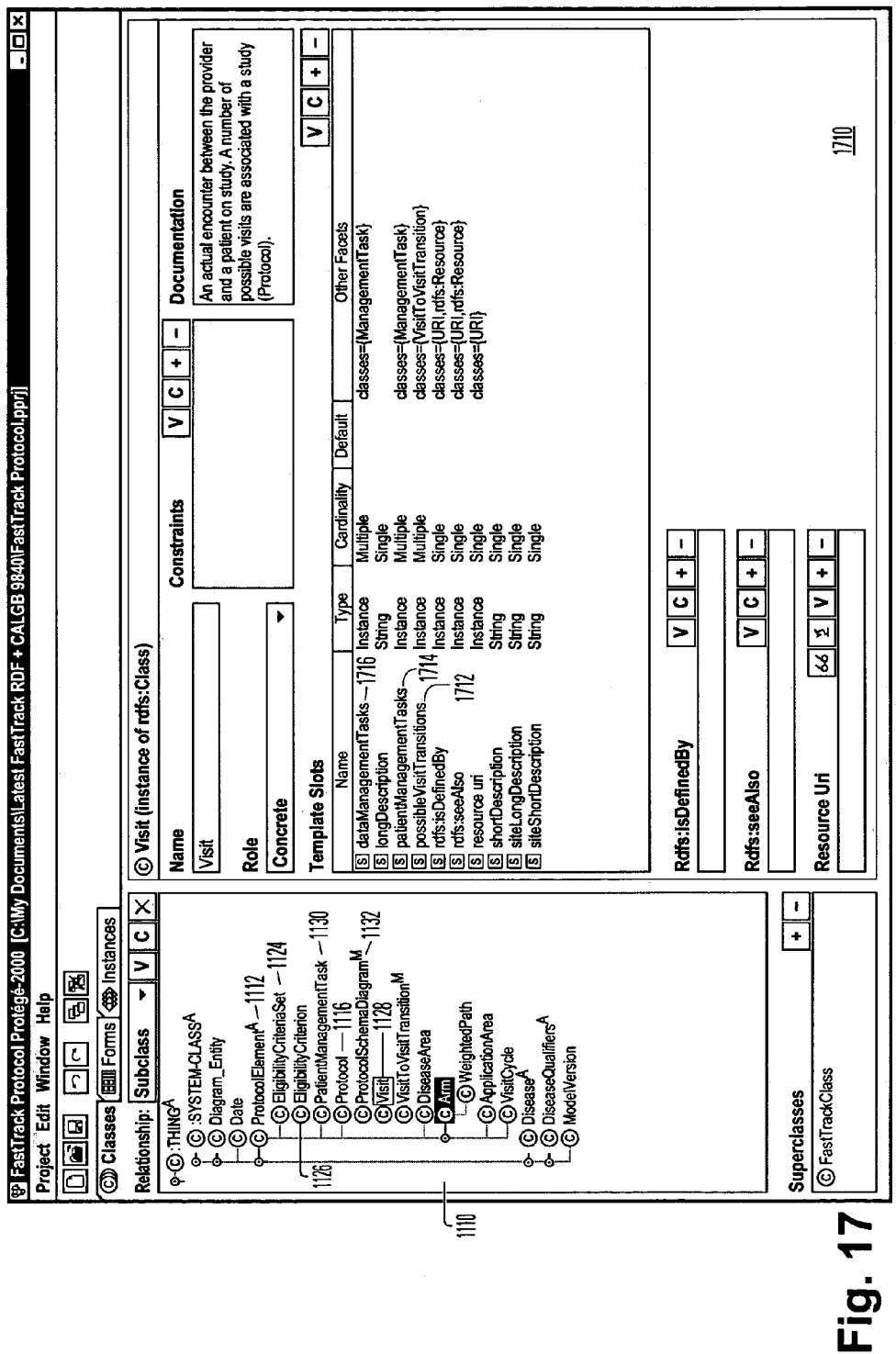

The iCP of FIG. 11 contains the protocol workflow in the form of patient visits, management tasks to take place during a visit, and transitions from one visit to another. The right-hand pane 1710 of FIG. 17 illustrates the slots available for an object instance of the class "visit" 1128. It can be seen that in addition to a slot 1712 for possible visit transitions, the Visit class also includes a slot 1714 for patient management tasks as well as another slot 1716 for data management tasks. In other words, a clinical trial protocol encoded in an iCP can include instructions to clinical personnel not only for patient management tasks (such as administer certain medication or take certain tests), but also data management tasks (such as to complete certain CRFs). The terms "visit" and "protocol event" are used interchangeably herein. Both are intended to refer to events called for in a protocol, and neither requires any actual patient contact, whether remote or in person. The terms also do not refer to what is known as "adverse events", which are not pre-scheduled.

Figure 18:
Figure 19:
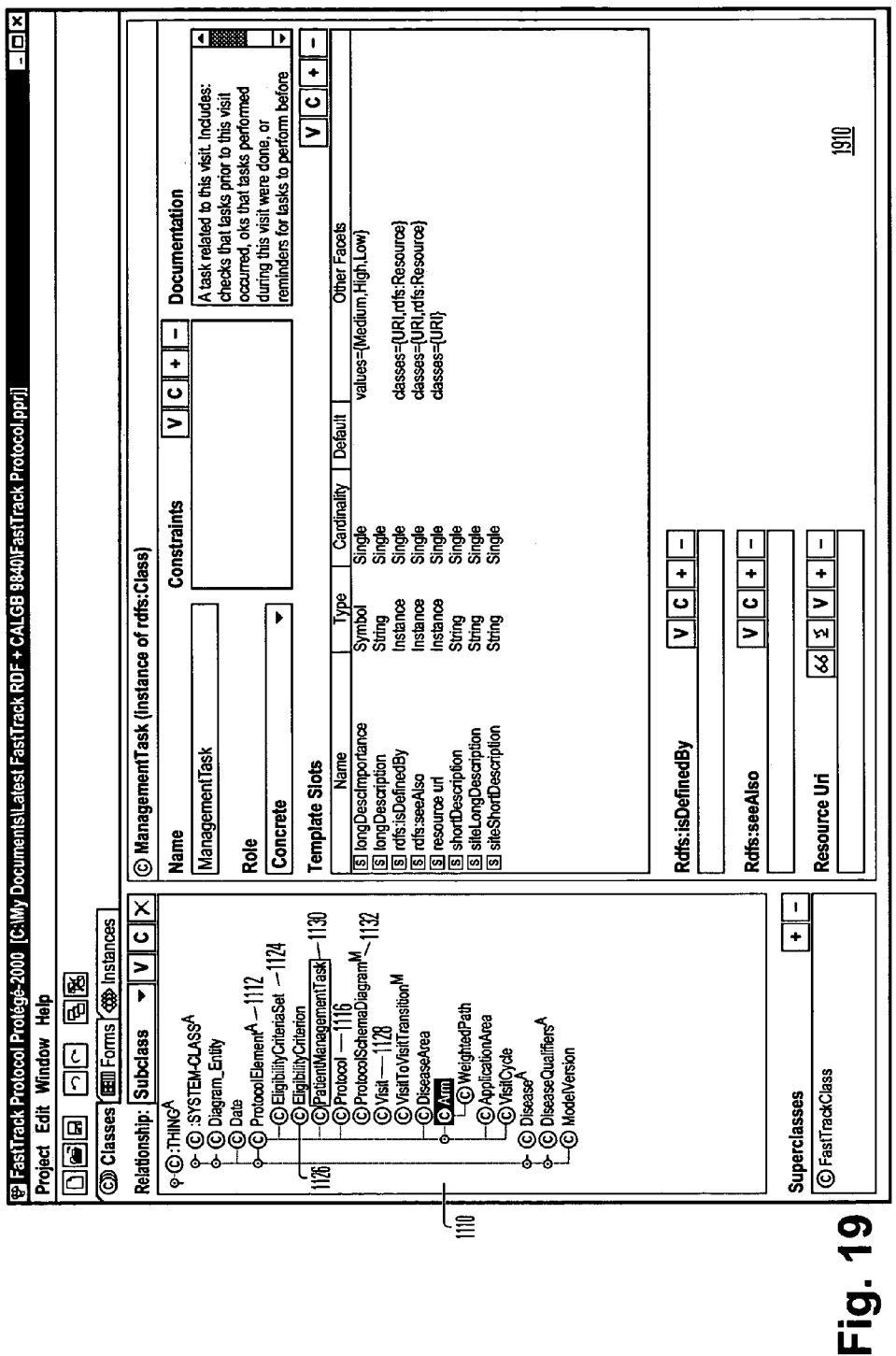

FIG. 18 illustrates a particular instance of visit class 1128, which is included in the CALGB 9840 iCP. As can be seen, it includes a window 1810 containing the possible visit transitions, a window 1812 containing the patient management tasks, and a window 1816 showing the data management tasks for a particular visit referred to as "Arm A treatment visit". The data management tasks and patient management tasks are all instance of the "PatientManagementTask" class 1130 (FIG. 11), the slots of which are set forth in the right-hand pane 1910 of FIG. 19. The slots available to a protocol designer in a PatientManagementTask object are mostly text fields. Another iCP embodiment is described below in which the study schedule part of the iCP includes taskVisit objects in which a task is associated with one or more Visit objects, and each such association further includes a TaskVisitPurpose attribute which identifies a purpose for performing the particular task in the particular visit. Each such association also identifies an Outcome object if the reason is to test efficacy or, in some circumstances, safety.

FIG. 20 illustrates the PatientManagementTask object 1816 (FIG. 18), "Give Arm A Paclitaxel Treatment" Similarly, FIG. 21 illustrates the PatientManagementTask object 1818, "Submit Form C-116". The kinds of data management tasks which can be included in an iCP according to the clinical trial protocol meta-model include, for example, tasks calling for clinical personnel to submit a particular form, and a task calling for clinical personnel to obtain informed consent.

Figure 22:
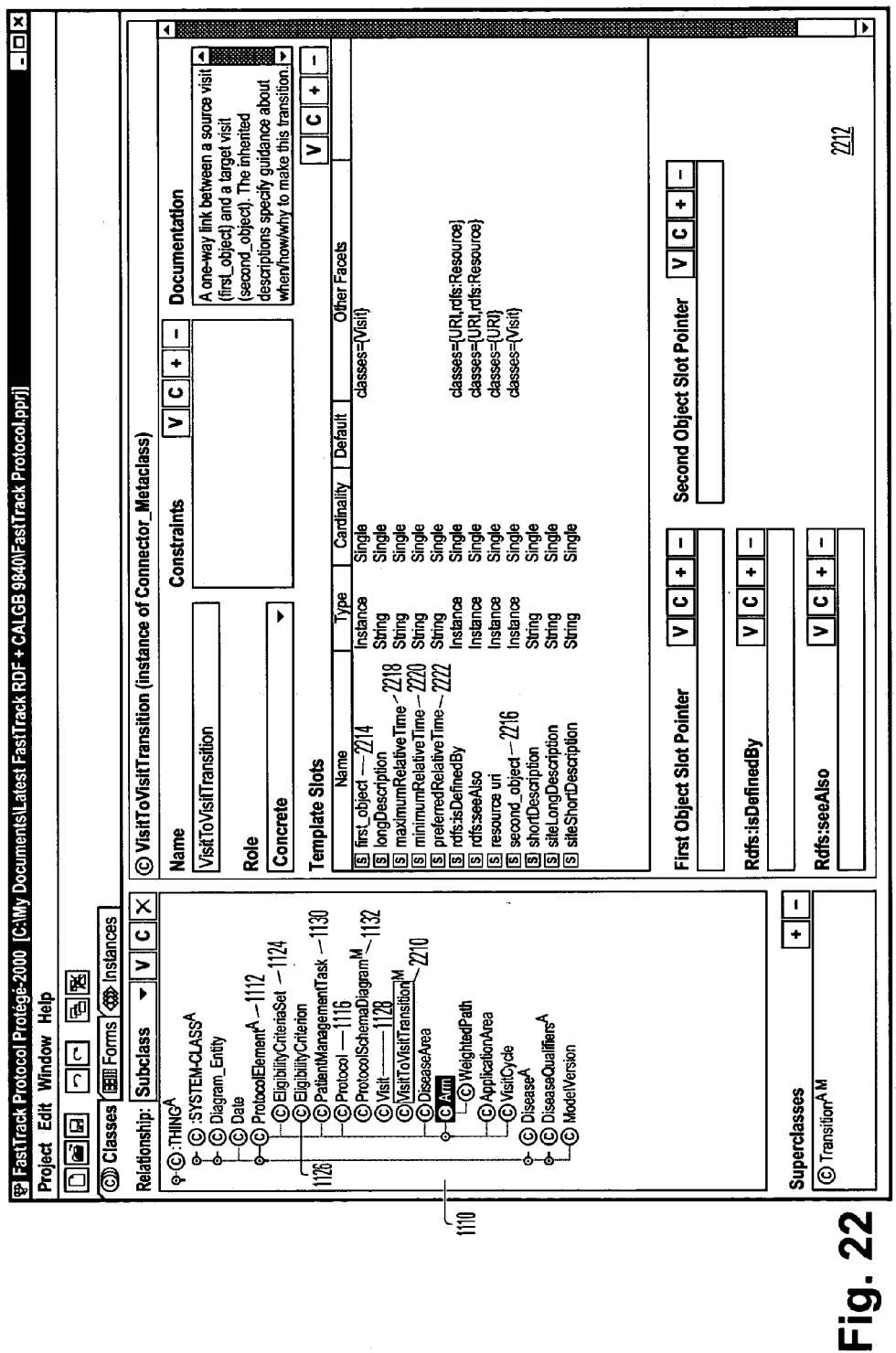

Returning to FIG. 17, the values that a protocol designer places in the slot 1712 of a visit class 1128 object are themselves instances of VisitToVisitTransition class 2210 (FIG. 22) in the meta-model. The right-hand pane 2212 shows the slots which are available in an object of the VisitToVisitTransition class 2210. As can be seen, it includes a slot 2214 which points to the first visit object of the transition, another slot 2216 which points to a second visit object of the transition, and three slots 2218, 2220 and 2222 in which the protocol designer provides the minimum, maximum and preferred relative time of the transition. FIG. 23 shows the contents of a VisitToVisitTransition object 1818 (FIG. 18) in the CALGB 9840 iCP.

Figure 24:
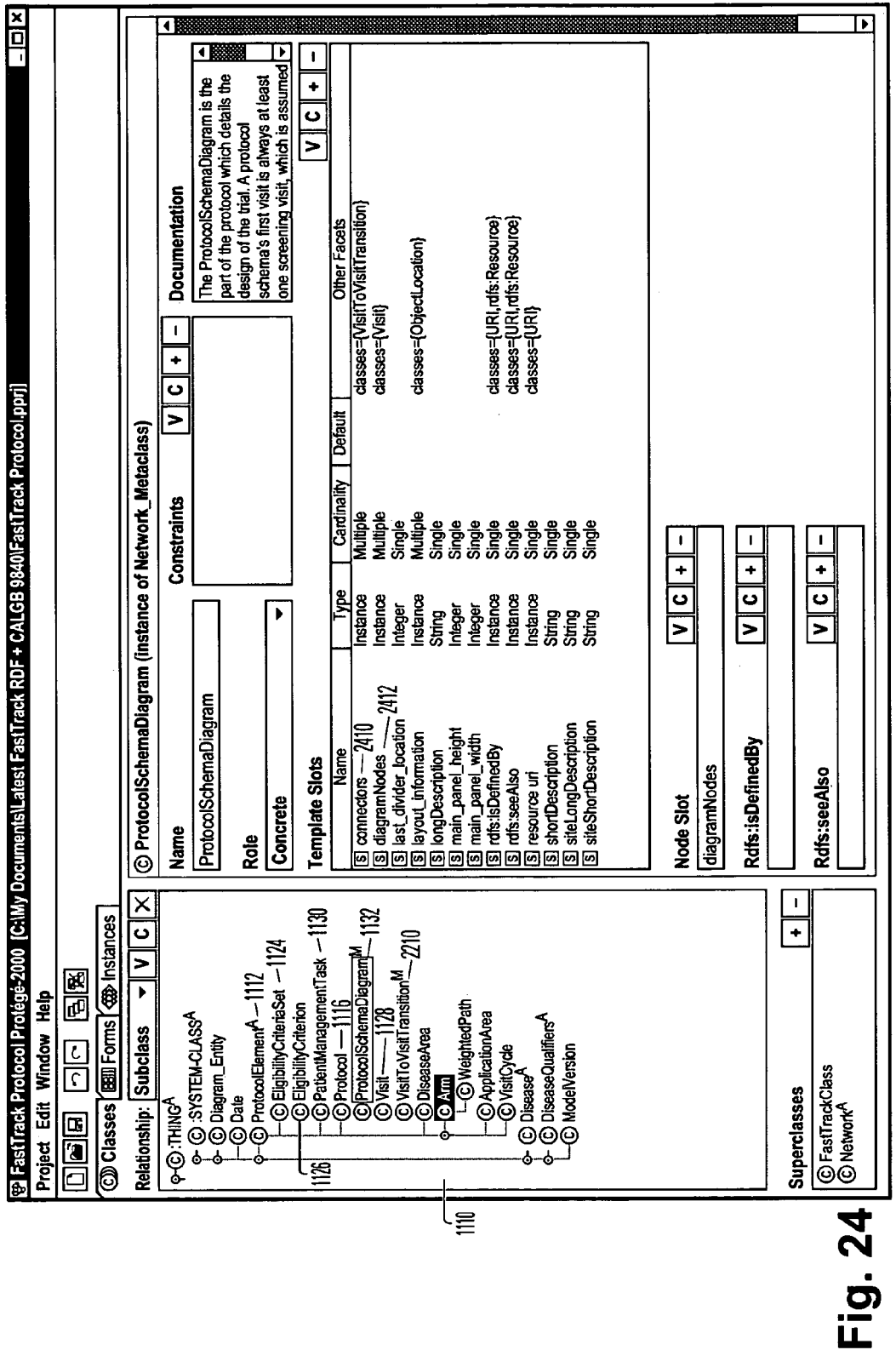
Figure 25:
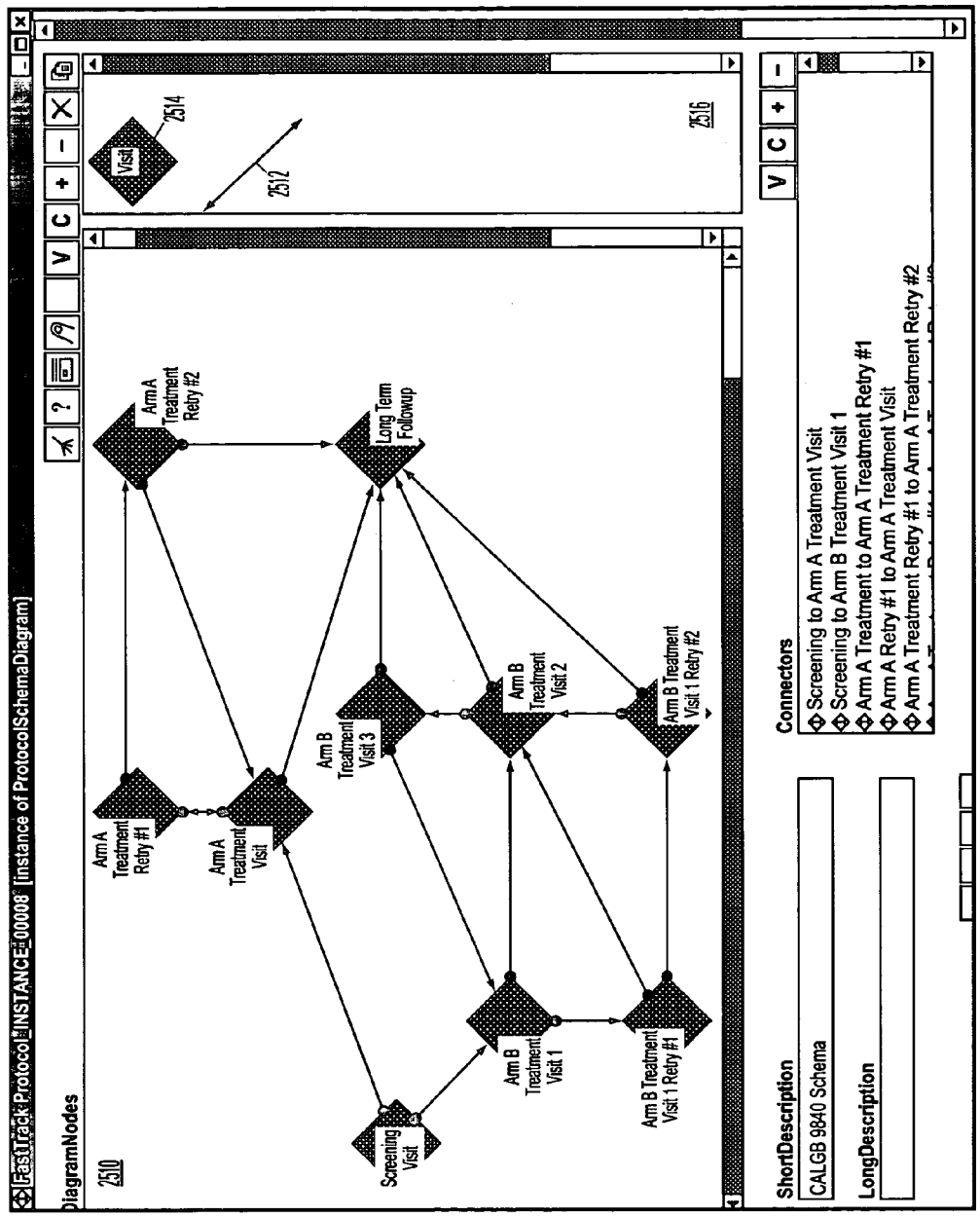

In addition to being kept in the form of Visit objects, management task objects and VisitToVisitTransition objects, the protocol meta-model also allows an iCP to keep the protocol workflow in a graphical or diagrammatic form as well. In fact, it is the graphical form that protocol designers typically use, with intuitive drag-and-drop and drill-down behaviors, when they encode clinical trial protocols using Protégé 2000. In the protocol meta-model, a slot 1134 is provided in the Protocol object class 1116 for pointing to an object of the ProtocolSchemaDiagram class 1132 (FIG. 11). FIG. 24 shows the slots available for ProtocolSchemaDiagram class 1132. As can be seen, they include a slot 2410 for diagrammatic connectors, and another slot 2412 for diagram nodes. The diagram connectors are merely the VisitToVisitTransition objects described previously, and the diagram nodes are merely the Visit objects described previously. FIG. 25 illustrates the ProtocolSchemaDiagram object 1214 (FIG. 12) in the CALGB 9840 iCP. It can be seen that the entire clinical trial protocol schema is illustrated graphically in pane 2510, and the available components of the graph (connector objects 2512 and visit objects 2514) are available in pane 1516 for dragging to desired locations on the graph.

FIGS. 2-8 are screen shots of another example iCP database, created and displayed by Protégé 2000 as an authoring tool. This iCP encodes clinical trial protocol labeled CALGB 49802, and differs from the CALGB 9840 iCP in that CALGB 49802 was encoded using a starting meta-model that was already specific to a specific disease area, namely cancer. It will be appreciated that in other embodiments, the meta-models can be even more disease specific, for example meta-models directed specifically to breast cancer, prostate cancer and so on.

FIG. 2 is a screen shot of the top level of the CALGB 49802 iCP database. The screen shot sets forth all of the text fields of the protocol, as well as a list 210 of patient inclusion criteria and a list 212 of patient exclusion criteria.

Figure 3:
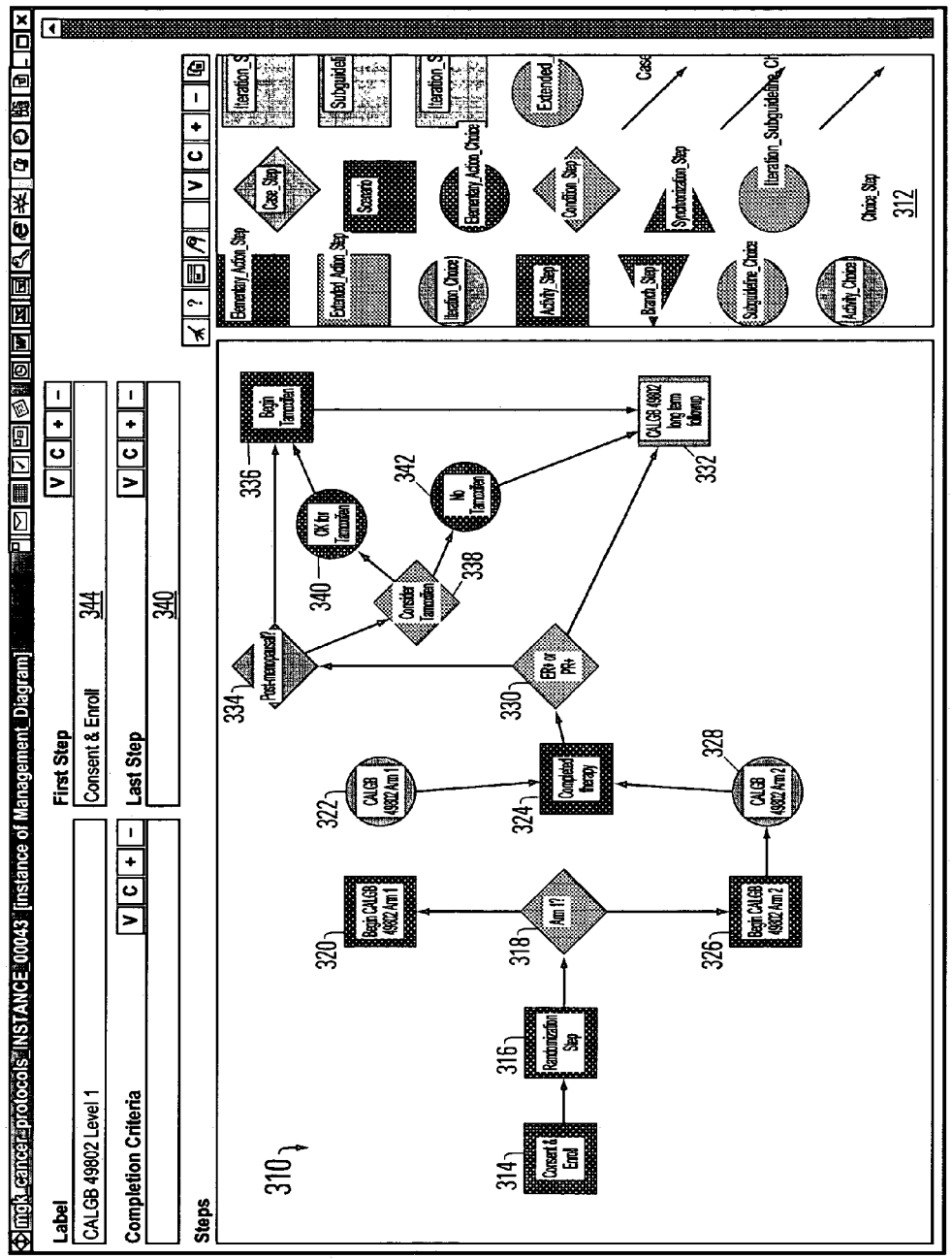

FIG. 3 is a screen shot of the Management_Diagram class object for the iCP, illustrating the workflow diagram for the clinical trial protocol of FIG. 2. The workflow diagram sets forth the clinical algorithm, that is, the sequence of steps, decisions and actions that the protocol specification requires to take place during the course of treating a patient under the particular protocol. The algorithm is maintained as sets of tasks organized as a graph 310, illustrated in the left-hand pane of the screen shot of FIG. 3. The protocol designer adds steps and/or decision objects to the graph by selecting the desired type of object from the palate 312 in the tight-hand pane of the screen shot of FIG. 3, and instantiating them at the desired position in the graph 310. Buried beneath each object in the graph 310 are fields which the protocol designer completes in order to provide the required details about each step, decision or action. The user interface of the Protégé 2000 authoring tool allows the designer to drill down below each object in the graph 310 by double-clicking on the desired object. The Management_Diagram object for the iCP also specifies a First Step (field 344), pointing to Consent & Enroll step 314, and a Last Step (field 346), which is blank.

Referring to the graph 310, it can be seen that the workflow diagram begins with a "Consent & Enroll" object 314. This step, which is described in more detail below, includes sub-steps of obtaining patient informed consent, evaluating the patient's medical information against the eligibility criteria for the subject clinical trial protocol, and if all such criteria are satisfied, enrolling the patient in the trial.

After consent and enrollment, step 316 is a randomization step. If the patient is assigned to Arm 1 of the protocol (step 318), then workflow continues with the "Begin CALGB 49802 Arm 1" step object 320. In this Arm, in step 322, procedures are performed according Arm 1 of the study, and workflow continues with the "Completed Therapy" step 324. If in step 318 the patient was assigned Arm 2, then workflow continues at the "Begin CALGB 49802 Arm 2" step 326. Workflow then continues with step 328, in which the procedures of protocol Arm 2 are performed and, when done, workflow continues at the "Completed Therapy" scenario step 324.

After step 324, workflow for all patients proceeds to condition_step "ER+ or PR+" step 330. If a patient is neither estrogen-receptor positive nor progesterone-receptor positive, then the patient proceeds to a "CALGB 49802 long-term follow-up" sub-guideline object step 332. If a patient is either estrogen-receptor positive or progesterone-receptor positive, then the patient instead proceeds to a "Post-menopausal?" condition_step object 334. If the patient is post-menopausal, then the patient proceeds to a "Begin Tamoxifen" step 336, and thereafter to the long-term follow-up sub-guideline 332.

If in step 334, the patient is not post-menopausal, then workflow proceeds to a "Consider Tamoxifen" choice_step object 338. In this step, the physician using clinical judgment determines whether the patient should be given Tamoxifen. If so (choice object 340), then the patient continues to the "Begin Tamoxifen" step object 336. If not (choice object 342), then workflow proceeds directly to the long-term follow-up sub-guideline object 332. It will be appreciated that the graph 310 is only one example of a graph that can be created in different embodiments to describe the same overall protocol schema. It will also be appreciated that the library of object classes 312 could be changed to a different library of object classes, while still being oriented to protocol-directed clinical studies.

Figure 4:
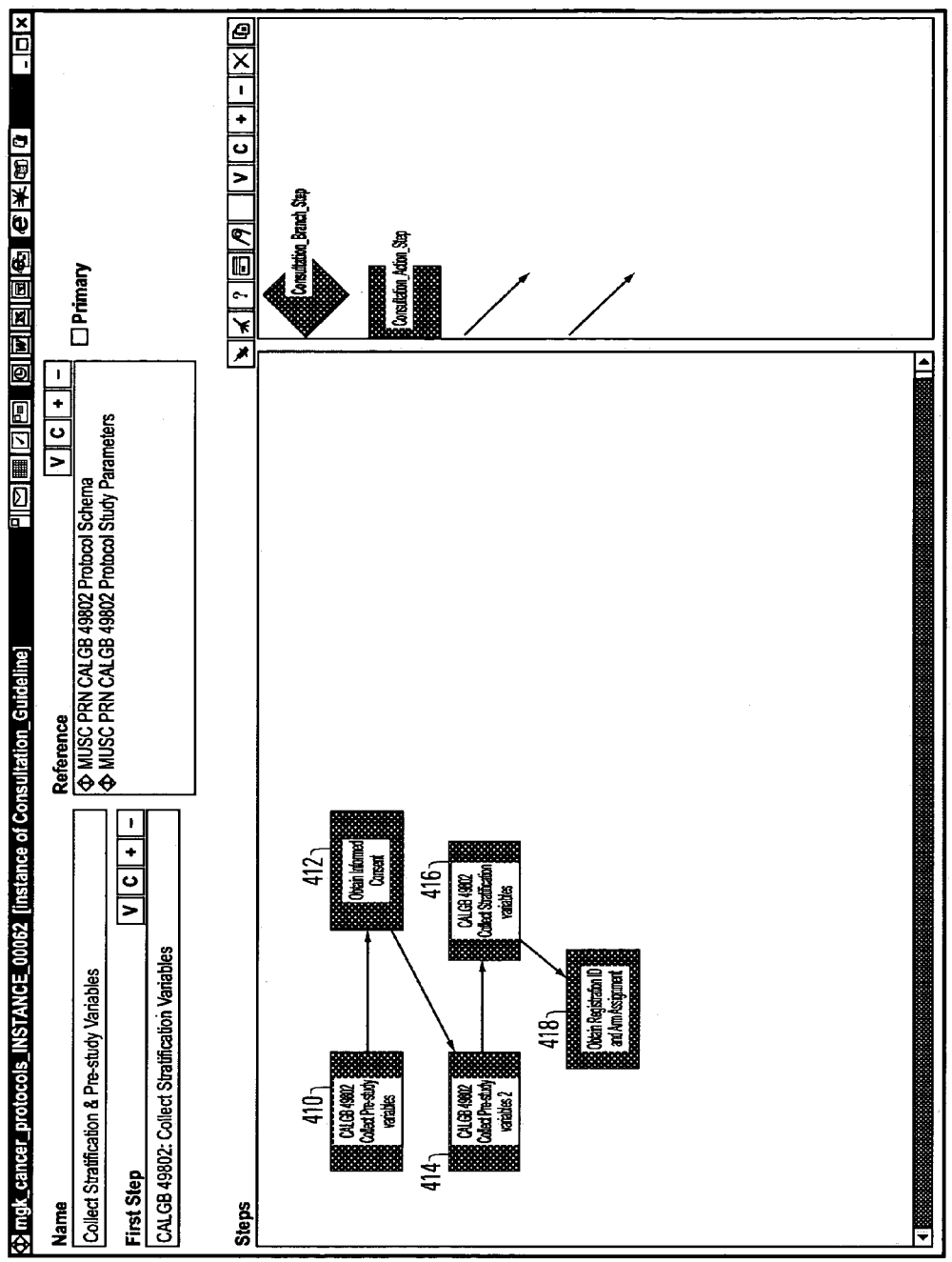

FIG. 4 is a screen shot showing the result of "drilling down" on the "Consent & Enroll" step 314 (FIG. 3). As can be seen, FIG. 4 contains a sub-graph (which is also considered herein to be a "graph" in its own right) 410. The Consent & Enroll step 314 also contains certain text fields illustrated in FIG. 4 and not important for an understanding of the invention.

As can be seen, graph 410 begins with a "collect pre-study variables 1" step object 410, in which the clinician is instructed to obtain certain patient medical information that does not require informed consent. Step 412 is an "obtain informed consent" step, which includes a data management task instructing the clinician to present the study informed consent form to the patient and to request the patient's signature. In another embodiment, the step 412 might include a sub-graph which instructs the clinician to present the informed consent form, and if it is not signed and returned immediately, then to schedule follow-up reminder telephone calls at future dates until the patient returns a signed form or declines to participate.

After informed consent is obtained, the sub-graph 410 continues at step object 414, "collect pre-study variable 2". This step instructs the clinician to obtain certain additional patient medical information required for eligibility determination. If the patient is eligible for the study and wishes to participate, then the flow continues at step object 416, "collect stratification variables". The flow then continues at step 418, "obtain registration I.D. and Arm assignment" which effectively enrolls the patient in the trial.

FIG. 5 is a detail of the "Collect Stratification Variables" step 416 (FIG. 4). As can be seen, it contains a number of text fields, as well as four items of information that the clinician is to collect about the subject patient. When the clinical site protocol management software reaches this stage in the workflow, it will ask the clinician to obtain these items of information about the current patient and to record them for subsequent use in the protocol. The details of the "Collect pre-study variables" 1 and 2 steps 410 and 414 (FIG. 4) are analogous, except of course the specific tasks listed are different.

Figure 6:
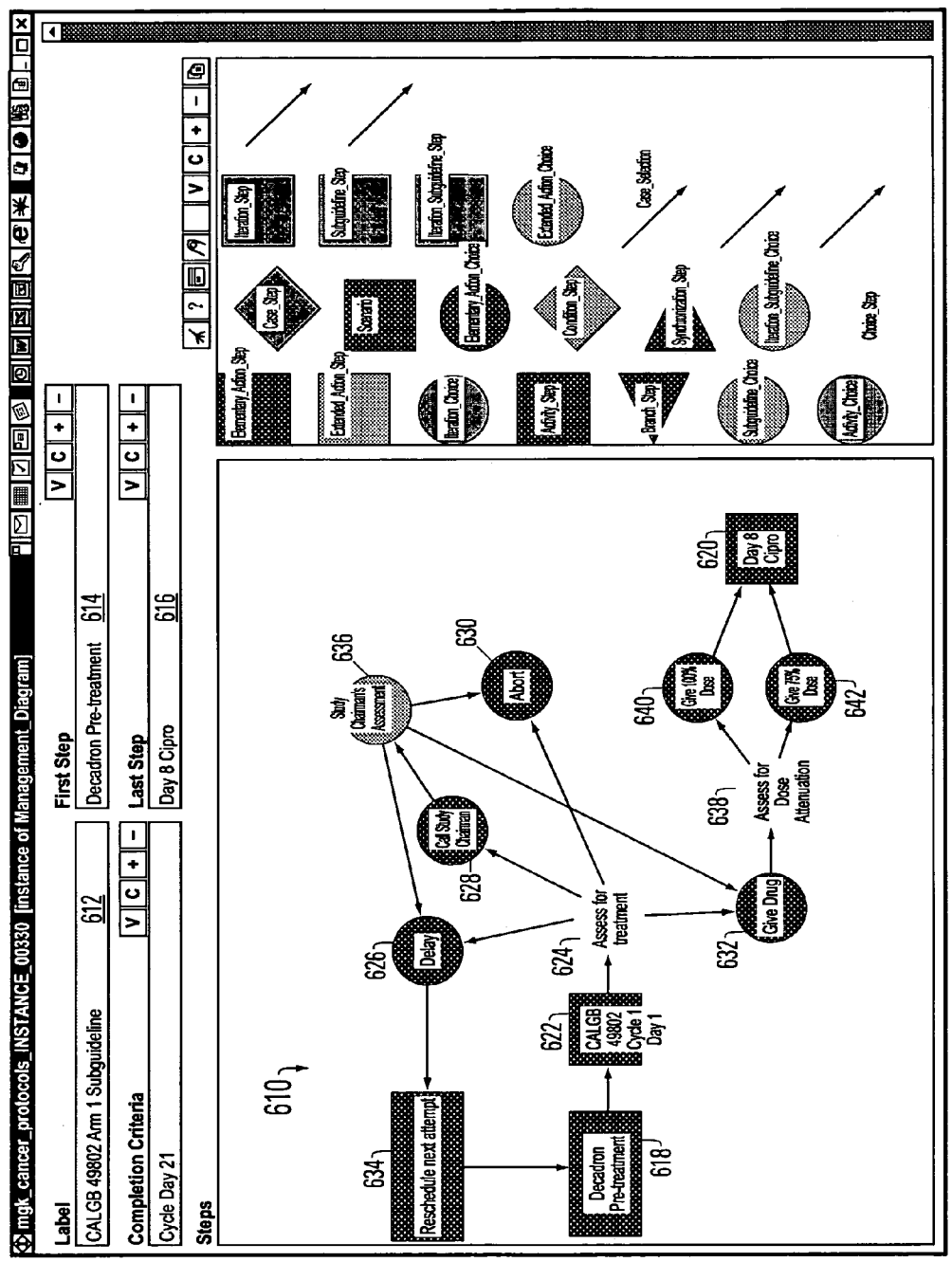

FIG. 6 is a detail of the "CALGB 49802 Arm 1" sub-guideline 332 (FIG. 3). As in FIG. 4, FIG. 6 includes a sub-graph (graph 610) and some additional information fields 612. The additional information fields 612 include, among other things, an indication 614 of the first step 618 in the graph, and an indication 616 of the last step 620 of the graph.

Referring to graph 610, the arm 1 sub-guideline begins with a "Decadron pre-treatment" step object 618. The process continues at a "Cycle 1; Day 1" object 622 followed by a choice_object 624 for "Assess for treatment." The clinician may make one of several choices during step 624 including a step of delaying (choice object 626); a step of calling the study chairman (choice object 628); a step of aborting the current patient (choice object 630); or a step of administering the drug under study (choice object 632). If the clinician chooses to delay (object 626), then the patient continues with a "Reschedule next attempt" step 634, followed by another "Decadron pre-treatment" step 618 at a future visit. If in step 624 the clinician chooses to call the study chairman (object 628), then workflow proceeds to choose_step object 636, in which the study chair makes an assessment. The study chair can choose either the delay object 626, the "Give Drug" object 632, or the "Abort" object 630.

If either the clinician (in object 624) or the study chair (in object 636) chooses to proceed with the "Give Drug" object 632, then workflow proceeds to choice_step object 638 at which the clinician assesses the patient for dose attenuation. In this step, the clinician may choose to give 100% dose (choice object 640) or to give 75% dose (choice object 642). In either case, after dosing, the clinician then performs "Day 8 Cipro" step object 620. That is, on the $8^{th}$ day, the patient begins a course of Ciprofloxacin (an antibiotic).

Without describing the objects in the graph 610 individually, it will be understood that many of these objects either are themselves specific tasks, or contain task lists which are associated with the particular step, visit or decision represented by the object.

Figure 7:
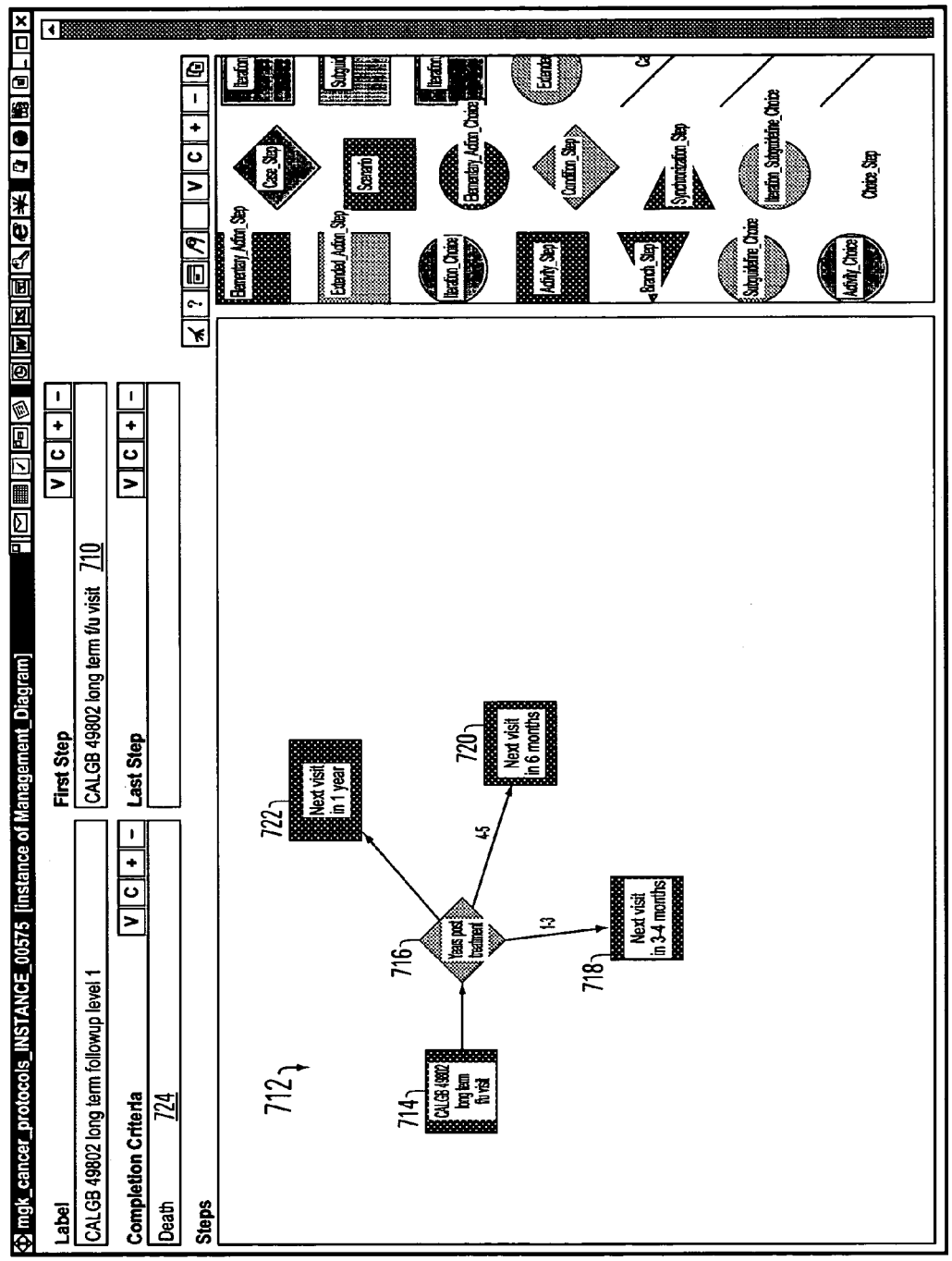

FIG. 7 is a detail of the long term follow-up object 332 (FIG. 3). As mentioned in field 710, the first step in the sub-graph 712 of this object is a long term follow-up visit scenario visit object 714. That is, the sub-guideline illustrated in graph 712 is executed on each of the patient's long-term follow-up visits. As indicated in field 724, the long term follow-up step 332 (FIG. 3) continues until the patient dies.

Object 716 is a case_object which is dependent upon the patient's number of years post-treatment. If the patient is 1-3 years post-treatment, then the patient proceeds to step object 718, which among other things, schedules the next visit in 3-4 months. If the patient is 4-5 years post-treatment, then the patient proceeds to step object 720, which among other things, schedules the next patient visit in 6 months. If the patient is more than 5 years post-treatment, then the patient proceeds to step object 722, which among other things, schedules the next visit in one year. Accordingly, it can be seen that in the sub-guideline 712, different tasks are performed if the patient is less than 3 years out from therapy, 4-5 out from therapy, or more than 5 years out from therapy. Beneath each of the step objects 718, 720 and 722 are additional workflow tasks that the clinician is required to perform at the current visit.

Figure 8:
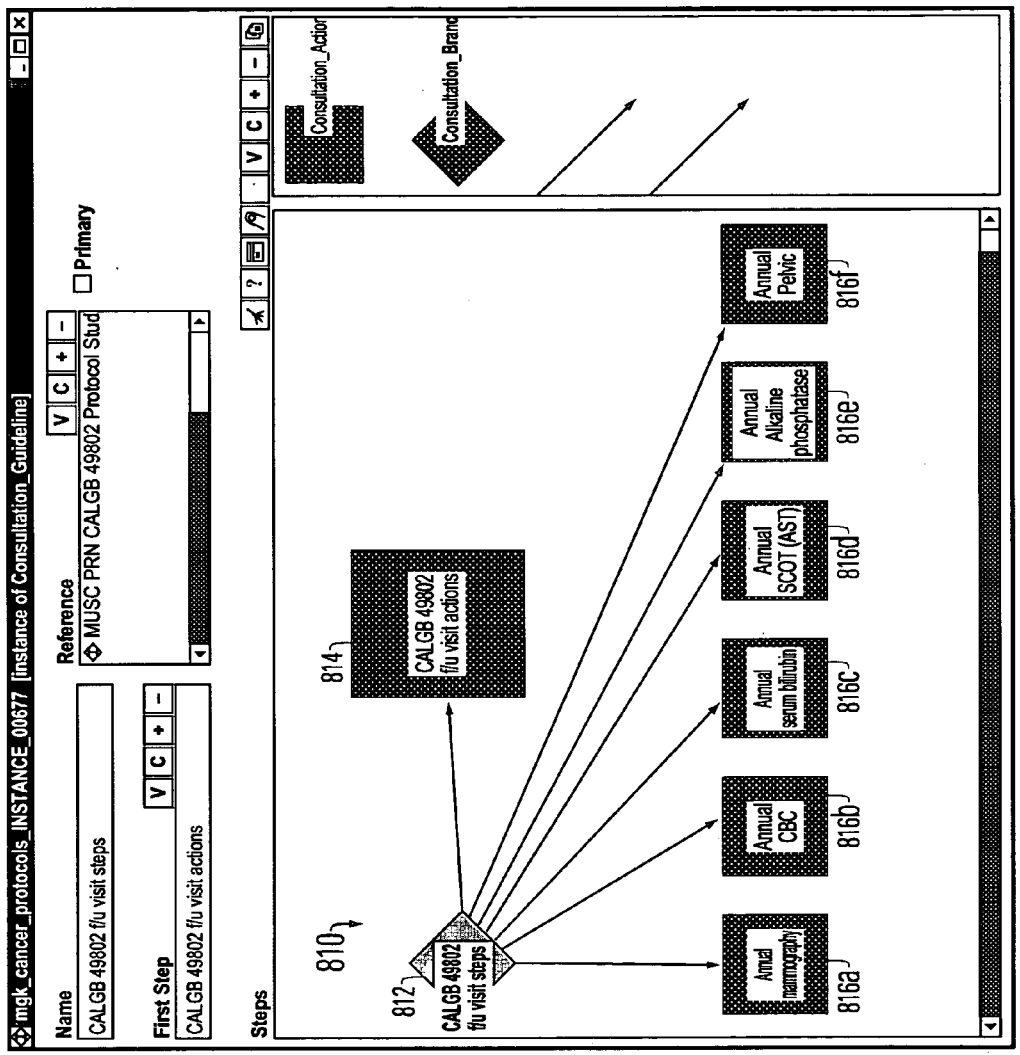

FIG. 8 is an example detail of one of the objects 718, 720 or 722 (FIG. 7). It includes a graph 810 which begins with a CALGB 49802 f/u visit steps" consultation_branch object 812, followed by seven elementary_action objects 814 and 816a-f (collectively 816). Each of the consultation action objects 814 and 816 includes a number of workflow tasks not shown in the figures. It can be seen from the names of the objects, however, that the workflow tasks under object 814 are to be performed at every follow-up visit, whereas the workflow tasks under objects 816 are to be performed only annually.

As mentioned, an iCP database can be represented in other formats aside from a Protégé 2000 database. Submitted herewith in the CD-ROM appendix is a file SampleInstance.xml.txt which describes yet another iCP database, using XML. A database of this format includes a number of element groupings to define a clinical trial protocol, including element groupings for administrative information, planned metrics, study design, study population information, clinical trial materials, schedule information, statistical information, and study conduct, among others. Of these, the study design and schedule element groupings are most pertinent to the present description.

The schema for a study schedule section is defined in the file schedule.xsd in the CD-ROM appendix. The section includes one or more Study Schedule objects defining, among other things, study periods, tasks to be performed during the study, and taskVisit objects. More than one treatment arm can be represented by including more than one Study Schedule object in this section. Each study period can stand by itself or can include one or more sub-periods (such as sub-phases within a treatment phase). Sub-periods and (if there are no sub-periods) periods, can include one or more Visit objects. Each Visit object contains certain information about the visit, including reference counts for the visit object in a document being developed.

In the iCP of SampleInstance.xml.txt, there are five periods defined, referred to as Pretreatment, Treatment, Follow up, Discontinued and Withdrawal From Study. The Follow-up period has two sub-periods designated Monitoring and Final Follow-up, but all the other periods have no sub-periods. The Pretreatment period contains two Visit objects having display names Screening and Baseline. The Treatment period contains five Visit objects having display names Visit1-Visit5. The Monitoring sub-period contains two Visit objects having display names Monitoring1 and Monitoring2, and the Final Follow-up sub-period contains one Visit object having a display name of Follow-up Visit. The Discontinued period has one Visit object having a display name of Discontinuation, and the Withdrawal From Study period has one Visit object with the same display name.

The Tasks subsection of a study schedule section in an iCP instance according to the schedule.xsd schema, defines at least one Task object that can be associated with Visit objects. In the iCP of SampleInstance.xml.txt, there are 10 Task objects defined, with display names such as Medical History, Neurological Exam, NIHSS, Modified Rankin Scale (mRS), Lab profile, Tympanic Temperature, Dosing, Barthel Index, Adverse Event Capture and Brain CT. The Task objects also include other information related to the particular task, such as who is to perform the task, cost information (discussed below), and the number of times the Task object is referred to in an associated document being developed.

The TaskVisits subsection of a study schedule section in an iCP instance according to the schedule.xsd schema, can define one or more TaskVisit objects. A TaskVisit object associates a task with a visit, and contains pointers to both the Task object and the Visit object. It also contains zero or more TaskVisitPurpose objects (preferably, a particular document type can require that there be at least one TaskVisitPurpose object in each TaskVisit object), each of which identifies a reason for performing the particular task in the particular visit. Each TaskVisitPurpose object can also point to an Outcome object (described below), and in some embodiments a pointer to at least one Outcome object is required for a particular document type if the reason for associating the particular task with the particular visit as given in the TaskVisitPurpose includes certain predefined reasons, such as efficacy and/or safety.

As examples of TaskVisit objects in the iCP of SampleInstance.xml.txt, there are three associated with object ID=6, which is Visit 4 in the Treatment Period. The three tasks associated in these three respective TaskVisit objects are object IDs 66, 7 and 9, which are the Task objects for Tympanic Temperature, Dosing, and Adverse Event Capture. Thus the clinical trial protocol as represented in the iCP of SampleInstance.xml.txt, the tasks of Tympanic Temperature, Dosing, and Adverse Event Capture are to be performed during Visit 4 in the Treatment Period. Each of these three tasks are to be performed in other visits as well, as indicated by other TaskVisit objects associating these Task objects with other Visit objects.

The schema for a study design section is defined in the file design.xsd.txt in the CD-ROM appendix. The section includes, among other things, subsections for defining primary, secondary and tertiary objectives for the study, outcomes (endpoints) for a patient in the study, and treatment arms, among other things. The objectives are defined in Objectives objects which contain a textual description of an objective, reference counts for the Objective object in a document being developed, pointers to Outcome objects associated with the objective, and an indication of whether the objective is primary, secondary or tertiary. For example, the iCP of SampleInstance.xml.txt defines one objective, which is which is to "Study effects of high-dose acetaminophen and ibuprofen on body temperature in patients with acute ischaemic stroke, and to study the safety of those treatments". This is identified in the Objective object as a primary objective, and is associated with all four of the outcomes defined for the study.

The possible outcomes for a patient in the study are defined in Outcome objects in the outcomes subsection. An Outcome object contains a textual statement of the outcome, reference counts for the Outcome object in a document being developed, an Outcome Type attribute (such as types primaryEfficacy, secondaryEfficacy, tertiaryEfficacy, safety, pharmacoeconomic and other), pointers to one or more associated Objective object, and an asMeasuredBy attribute. The asMeasuredBy attribute contains one or more Measurement objects, each of which points to a TaskVisit object. Preferably, a particular document type requires that at least all Outcome objects of a particular type, such as type primaryEfficacy, include at least one Measurement object in the asMeasuredBy attribute.

In the iCP of SampleInstancexml.txt there are four Outcome objects defined. The first Outcome object is described as "Body temperature at 24 hours from start of treatment", and is of type primaryEfficacy. This outcome is identified as being measured by two TaskVisit objects, namely TaskVisit object ID=17967174318, which associates the Tympanic Temperature task (Task object ID=66) with Visit 1 (Visit object ID=3) in the Treatment period, and TaskVisit object ID=17967174315, which associates the same task with the Baseline Visit object (Visit object ID=2) in the Pretreatment period. Thus according to this example protocol, this outcome will be measured by tympanic temperature measurements taken during the baseline visit in the pretreatment period and the first visit in the treatment period.

The second, third and fourth Outcome objects in SampleInstance.xml.txt are of types secondaryEfficacy, secondaryEfficacy (again) and tertiaryEfficacy, and are described as "Change in baseline temperature at 1 and 5 days from start of treatment", "Time with elevated body temperature during the first 24 hours and the first five days" and, "Functional outcome at 1 month", respectively. The attributes of these Outcome objects are evident from the file SampleInstance.xml.txt.

The treatment arms subsection of a study design section of an iCP according to the file design.xsd.txt defines one or more treatment arm objects, each of which defines such attributes as the planned enrollment for the arm, the randomization weight for the arm, the materials associated with the arm, and a pointer to a Study Schedule object as described above. One treatment arm can have many schedule objects associated with it, and one schedule object can be associated with more than one arm. The iCP of SampleInstance.xml.txt, as an example, includes one treatment arm identifying one Schedule object described above.

Because of the ability to support domain-independent PSMs, certain iCP embodiments described herein enable automation of the entire trials process from protocol authoring to database lock. For example, an iCP can be used to create multiple trial management tools, including electronic case report forms, data validation logic, trial performance metrics, patient diaries and document management reports. The iCP data structures can be used by multiple tools to ensure that the tool performs in strict compliance with the clinical protocol requirements. For example, an accrual simulation tool can be implemented as a domain-independent PSM. Similarly, an embodiment can also include a PSM that clinical sites can use to simulate their own accrual in advance of signing on to perforin a given clinical trial. A single PSM is used to simulate accrual into a variety of studies, because the patient eligibility criteria are all identified in a predetermined format in the iCP for each study. Another PSM helps clinical sites identify likely patients for a given clinical trial. Yet another PSM guides clinicians through the visit-specific workflow tasks for each given patient as required by the protocol. The behavior of all these tools is guaranteed to be consistent with the protocol even as it evolves and changes because they all use the same iCP. The tools can also be incorporated into a library that can be re-used for the next relevant trial, thus permitting knowledge to be transferred across trials rather than being re-invented each time.

Not all embodiments of the protocol design tool described herein necessarily produce a protocol modeling database that includes the specific details needed to drive all the various kinds of PSMs. Nevertheless, important benefits can be obtained by the formal capture and encoding of even some of the parameters of the protocol in the structured database. For example, content from the protocol document can be re-used in the creation of other trial-related documents, such as the final study report. The formally captured parameters enforce consistency not only throughout a single document, but across all documents produced from the same iCP database. They also enable rule-based testing of documents for satisfaction of document-type-specific completion criteria, or satisfaction of other predefined criteria. They also facilitate structured retrieval of content from the document set, and submission of protocol parameters to other databases such as clinicaltrials.gov.

Intelligent Clinical Document Creation—System Overview

As mentioned, despite the complexity of the overall clinical trial design and execution effort, most protocols and related study documents are written today using only a simple word processor, a handful of document templates or macros, broad regulatory guidance, and, in some cases, an electronic or hardcopy version of a previous or similar protocol. Paper or electronic documents are passed between personnel in clinical development, clinical operations, biometrics, information technology, regulatory affairs, and marketing. Outside consultants, clinical research organizations, and potential key principle investigators may also be included in one or more steps in the protocol creation cycle. Each group reads, interprets, and extracts the information required for their specific responsibilities. As comments, revisions, or amendments occur, each group must evaluate these changes for any impact orr prior work and repeat the read/interpret/extract cycle. Operational considerations are often not considered when features are added or removed during review cycles. Many years later, when faced with combining the entire clinical development program, changes both within and between studies must be accurately evaluated, explained, and incorporated into integrated clinical summary reports and the final regulatory submission. The difficulty of this task is compounded by the high rate of transition among members of clinical development programs with whom the history of changes often rests.

Many operational issues can be identified and corrected early in the process by requiring that a protocol be encoded into a structured protocol modeling database, but it would be desirable to be able to take advantage of the structured nature of such a database in assisting the initial design of the protocol document as well.

FIG. 1 is an overall functional diagram of an embodiment of a system that can perform this function. In this diagram, parallelograms represent databases, circles represent tools or services which act on the databases, and wavy-bottom rectangles represent persistent or non-persistent documents. In the present embodiment, some of the databases represented by parallelograms are represented on disk as one or more XML documents.

Referring to FIG. 1, a protocol design tool 110 is the primary interface to a user who is designing a protocol instance. The protocol design building blocks available to the user are provided to the protocol design tool 110 by an iCP model database 114. These building blocks are based on regulatory considerations and elements commonly used in all protocols, as derived from guidelines such as International Committee on Harmonization (ICH), "Structure and Content of Clinical Study Reports," (E3), recommended for adoption at Step 4 on Nov. 30, 1995, www.ich.org (ICH E3), and ICH, "Guideline for Good Clinical Practice," (E6, Section 6), recommended for adoption at step 4 May 1, 1996 (ICH E6) (both incorporated by reference herein). Often they are also customized according to the unique requirements of a particular company or study sponsor design group.

The protocol design tool 110 is also responsive to an iCD model database 116. The iCD model database 116 is shown in FIG. 1 as being divided into two sub-databases: a mapping specification 118 and an iCD template 120. Other iCD model databases 116 can be divided differently, or not all. The iCD model database can also include other information that is not provided to the protocol design tool 110, or is provided only indirectly.

In FIG. 1, the iCD template 120 describes the overall structure of a desired document type, such as a clinical trial protocol document for regulatory approval. It includes, among other things, the overall document structure, typographic formats with which data is to be presented at various locations in the document, and are based on regulatory considerations and elements commonly used in all protocols, as derived from guidelines such as ICH E3 and ICH E6, and if desired can include predetermined values for certain protocol elements. The document template 120 is created during a pre-design configuration step and becomes an initial iCD instance 130. The mapping specification 118 in the iCD model 116, among other things, defines the element chooser from which the user chooses elements to view or include in the document being created by the protocol design tool 110. In one embodiment, the element chooser includes at least those elements defined by ICH E6, section 6 (contents of a protocol, according to good clinical practice). The mapping specification 118 also defines which of these elements a sponsor design group requires in each particular type of document, and the order and groupings in which they are to appear in the element chooser pane for that document type. The mapping specification 118 also includes fixed value elements configured for the sponsor design group (such as the name of the sponsor), which the user can instantiate in a document instance but cannot edit. All of this information is provided to the protocol design tool 110.

The protocol design tool 110 allows the user to enter information using a number of different methods. In one method, the protocol design tool 110 provides design guides which allow the user to enter certain basic information about the protocol being designed. In another method, the user is presented with a list of iCP elements in a chooser pane, organized in topic groups, and from which the user can select elements to browse or insert into the protocol document. As mentioned, the lists of which protocol elements are available for choosing in a particular document, and which are required in a particular document, are provided by the mapping specification 118. Certain choices made by the designer can be assisted by reference to a historical database 920, described hereinafter. In yet another method, the user is presented with a dynamically updated view of the document being created, and can indicate, by pointing and clicking in the document view, the field or document sections that the user would like to work on next, just as is done in a typical word processor program. In addition, the user can navigate around the document by clicking on a desired heading in a hierarchical document table of contents. For all of the entry methods, whenever the user changes document text or other document features that do not implicate iCP elements, the protocol design tool 110 updates the iCD instance 130 with the revisions. Whenever the user updates iCP elements (by adding elements, deleting elements or changing element values), the protocol design tool 110 updates an iCP instance 122 with all the revisions. As mentioned, the iCP instance 122 can at the same time be used to update and ensure consistency across references to protocol elements within an evolving document or document collection, and in certain embodiments it can also be used to drive a tool which governs the execution of a clinical trial 124, and to drive other downstream problem solvers 126 as well.

The iCP instance database 122 is also used by a document creator tool 128 to generate and update the iCD instance 130 that is shown to the user in the dynamic document creation window of the protocol design tool 110. The document creator tool 128 promptly refreshes the dynamic document creation window whenever the user commits to a change in any iCP elements that are referenced in the iCD instance. The iCD instance is essentially a Microsoft Word document that includes visible indicators and invisible codes. Visible indicators are used for such things as identifying to the user fields in the document that refer to data in the iCP, fields in the document that have yet to be filled in, and whether certain fields are required (as specified in the mapping specification 118). Invisible codes are used for such things as identifying to the system the location in the document that corresponds to the location of user behavior in the dynamic document window. The protocol design tool 110 includes menu choices by which the user can save the current iCD instance as a Microsoft Word document on disk, or print the current iCD instance.

The system of FIG. 1 also includes a protocol advisory service 134. At any time during or after protocol design, the user can request that a protocol advisory analysis be executed on the document being created. The protocol advisory service 134 uses a set of predefined rules to identify ambiguities and omissions of required elements in the iCD instance being created, and to identify missing links between related information. In order to accomplish this, the protocol advisory service 134 receives information from the iCP instance 122 and the iCD instance 130 as they currently exist, and the required elements list from the mapping specification 118. The list of advisory rule sets to execute for a particular document type can in some embodiments be provided by the mapping specification 118. The protocol advisory service 134 produces a list of advisories indicating for the user further work or data entry that is required or desirable. The user has the option of correcting the issue that resulted in each advisory or, for certain advisories, entering a justification for why no correction is required.

Overall System Flow

Figure 9:
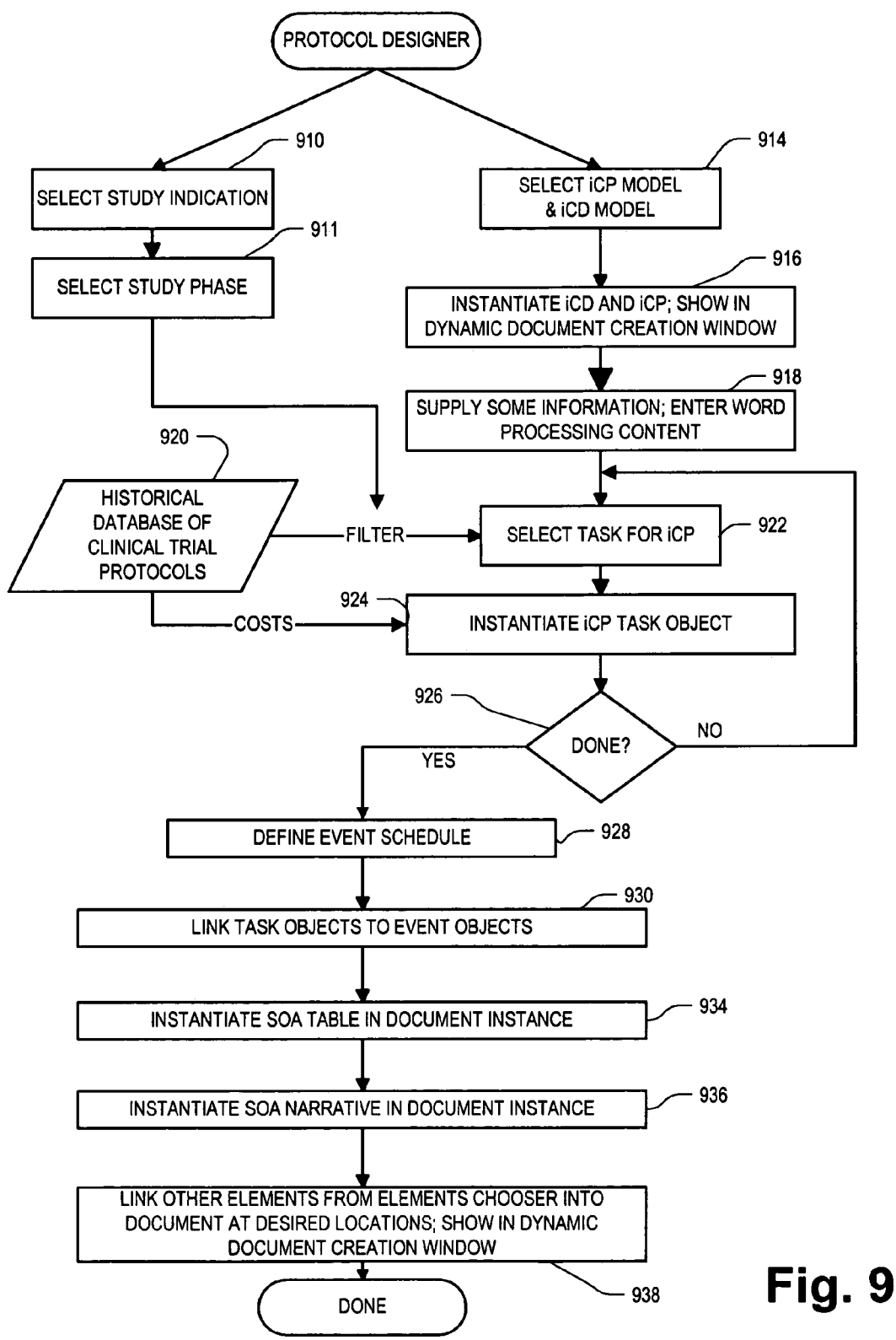
FIG. 9 is a flowchart illustrating certain major tasks that might be performed by a user operating the protocol design tool of FIG. 1.

FIG. 9 is a flowchart illustrating certain major tasks that might be performed by a user operating the protocol design tool 110 (FIG. 1). It will be appreciated that many of the steps illustrated in this flowchart (as well as in the other flow charts herein) can be performed in parallel or in a different sequence without affecting the functions achieved.

Referring to FIG. 9, the protocol designer user first selects an appropriate iCP model 114 from which to design an iCP protocol instance. There may be one or more different available document types that can be prepared using the selected iCP model, but in step 914 it is assumed that the user chooses the iCP model corresponding to a protocol document for submission to the U.S. Food and Drug Administration. Other types of models that might be made available at this stage include protocol models for other regulatory authorities in other countries, synopsis documents, informed consent forms (ICFs), trial study reports, institutional review board (IRB) letters and investigator study manuals. In step 916 the system instantiates both the iCP instance 122 and the iCD instance 130 (FIG. 1). The document is instantiated using standard texts, images and pre-specified company values provided by the document template 120. In step 918, the user then begins entering enters certain basic contextual information such as the title of the protocol, the version date and time, and the sponsor name and address, to the extent not already provided by the template 120.

At this point the user can approach the protocol design task in almost any desired sequence. The protocol design tool 110 allows both structured and unstructured entry and does not enforce any specific sequence of work. As mentioned, the user can enter information using one or more design guide workpanes or workpane shortcut buttons, or can insert an iCP element from an element chooser presented to the user through the GUI, or can navigate to another area of the document to work on via the table of contents pane, or can click within the dynamic document creation window to work directly within the document. The flowchart of FIG. 9 illustrates only one possible sequence. For example, step 918 also includes a substep of entering word processing content. While this step is shown in FIG. 9 once near the beginning of the authoring process, typically the entering of word processing content is the great bulk of the designer's work and will occur throughout the process before, after and between many of the steps shown in the figure.

The user can also instantiate an iCP element reference at a desired position in the document in a number of different ways depending on the element type. For simple elements, such as the protocol title or the phase of the study, the user can perform various intuitive behaviors in various embodiments, such as double-clicking on the element in the chooser pane to insert it into a desired position in the document in the document window. The user can assign or change the value of a simple element through the use of a workpane associated with that element type, invoked through the design guide or shortcut buttons, or by appropriate behavior relative to either the place where the element appears in the chooser pane or a place where a reference to it has been instantiated in the document. In all such methods, the protocol design tool 110 makes the desired change to the element in the iCP instance 122 when the user signals a commit, and the document creator 128 then refreshes all references in the document to the same iCP element. In some embodiments the user can assign or change the value of an iCP element by entering the modification directly in the document window where the element reference appears. Even here, however, the system makes the desired change first to the element in the iCP instance 122, and then in the document at all references to the iCP element.

In some embodiments the chooser pane can include library elements that the user can instantiate at desired positions in the document instance by appropriate behavior. Library elements typically are standard text excerpts that have been pre-drafted for the user, and instantiation of such an element in the document involves copying the text into the document rather than inserting an element reference. If the text of a library element were to change, the change would not appear in the document instance unless the user re-instantiates the element therein.

In some embodiments the chooser pane can include elements that invoke a dynamic template when selected by the user for instantiation in the document instance. A dynamic template is a pre-programmed procedure that automatically generates complex content from iCP elements, such as a list of all tasks to be performed at any time during the study, and instantiates the content into the document instance. One dynamic template can provide generated content with complex formatting, such as a table format. One dynamic template can generate what appears to be text, by placing element references into the document instance in a desired sequence and inserting text between and around the element references. One dynamic template, when it includes an iCP element in the generated content, does so by instantiating a reference to the element; in which case the element as it appears in the document instance will be updated whenever document creator 128 refreshes the dynamic document creation window. One dynamic template, when it includes an iCP element in the generated content, does so by converting the element's value to text. In this case the element as it appears in the document instance will not be updated when document creator 128 refreshes the dynamic document creation window. One dynamic template, when it inserts the generated content into the document instance, marks it (or parts of it) in the document instance as "protected" so that the user is unable to edit it directly in the document window. In this case the dynamic template might insert a code into the document instance, associated with the protected regions of the generated content, such that user selection of a protected region automatically invokes one or more workpanes appropriate for editing the iCP elements referenced in the protected region.

In one embodiment, generated content inserted into the document by a dynamic template can be marked with a reference to the dynamic template such that a document refresh operation not only updates the simple element references in the document to reflect value changes made to the element in the iCP, but also re-executes all dynamic templates referenced in the document (or at least all those affected by the changes made in the iCP). As an example, suppose the user desires to insert into the document instance a list of all tasks to be performed at any time during the study. Such a procedure would collect all tasks currently instantiated in the iCP and insert them in the document instance as a list. In an embodiment supporting dynamic templates that are executable only from the chooser pane, the dynamic template might instantiate a reference in the document instance to each task element that exists in the iCP instance 122 at that point in the authoring process. This can be cumbersome, however, if for example the user subsequently deletes a task or instantiates a new task in the iCP instance. In this case the user would also have to manually re-execute the dynamic template to take account of the deleted or newly instantiated tasks. In an embodiment that supports dynamic template references in the document instance, however, the template procedure can be designed to automatically re-execute on every document refresh, or at least on document refreshes that resulted from a change that affected task objects in the iCP.

Continuing with FIG. 9, in step 922, the user begins selecting tasks that will be performed within the protocol. Task selection may be informed by historical database 920 as described in more detail below, and this may be enhanced by establishing the indication (step 910) and the study phase (step 911) for the protocol before or during step 922. In step 924, each task chosen in step 922 is instantiated in the iCP instance 122 as an iCP task object. If the user is not finished entering new tasks yet (step 926), then he or she returns to step 922 in order to choose another task for inclusion in the protocol. At any point, more tasks can be added. After all tasks, or at least some number of tasks, have been instantiated into the protocol database, then in step 928, the user uses the protocol design tool 110 to define an event schedule to be included in the protocol. An event can be a study period, a study subperiod, or a visit. Containment may be defined between periods, subperiods, and visits. The events defined in step 928 are instantiated into the iCP instance 122 and, if the iCD instance 130 already contains a reference to an appropriate re-executable dynamic template, then the document creator 128 automatically updates the iCD instance 130 to show the new information. After events have been defined, then in step 930, the user uses the protocol design tool 110 in order to link individual tasks chosen in the step 922, to individual events defined in step 928. A given task may be linked to any number of the events. In response, the protocol design tool 110 instantiates TaskVisit objects in the iCP instance 122 linking the desired task objects and desired event objects at which the tasks are to be performed.

In step 934, the user instantiates a Schedule of Activities (SOA) table into the document instance 130 by placing the insertion point at a desired position in the document window and invoking an "SOA Table" dynamic template from the chooser. As described in more detail below, the protocol design tool 110 then collects all the iCP elements required for such a table, including visits, tasks and task-visit associations, formats the information as a table and inserts it with appropriate text as needed at the insertion point. In the present embodiment the SOA Table dynamic template converts all iCP element values that it uses into text so that they will not update automatically on document refresh, protects the entire generated content, and inserts an invisible code that will invoke an appropriate workpane should the user click in the table.

In step 936, the user instantiates an SOA narrative into the document instance 130 by placing the insertion point at a desired position in the document window and invoking an "SOA Narrative" dynamic template from the chooser. Again as described in more detail below, the protocol design tool 110 then collects all the iCP elements required for such a narrative, sequences them and inserts appropriate text before, after and between them, and inserts the resulting content into the document instance at the insertion point. Importantly, the set of iCP elements included in the content generated by the SOA Narrative dynamic template overlaps with the set of iCP elements included in the content generated by the SOA Table dynamic template. As between any two dynamic templates, the sets of iCP elements included can overlap partially or fully; as used herein, a "full overlap" means the two sets are the same. In the present embodiment the SOA. Narrative dynamic template instantiates in the document instance all iCP element values that it uses as iCP element references, so that unlike the content generated by the SOA Table dynamic template, these element references will update automatically on document refresh.

In step 938, the user then proceeds to link other elements from the element chooser into the document at desired locations, and for many such user behaviors, the protocol design tool 110 updates the iCP instance 122 to reflect the user's action. The document creator 128 then accordingly updates the iCD instance 130.

In order to better understand user navigation through the document and the protocol design task, it will be helpful to illustrate certain graphical user interface (GUI) features that assist the user. As mentioned, use of these features is only one way that the user might proceed. The protocol design tool 110 also provides a guided information entry mechanism that can be used for part or all of the design.

Figure 10:
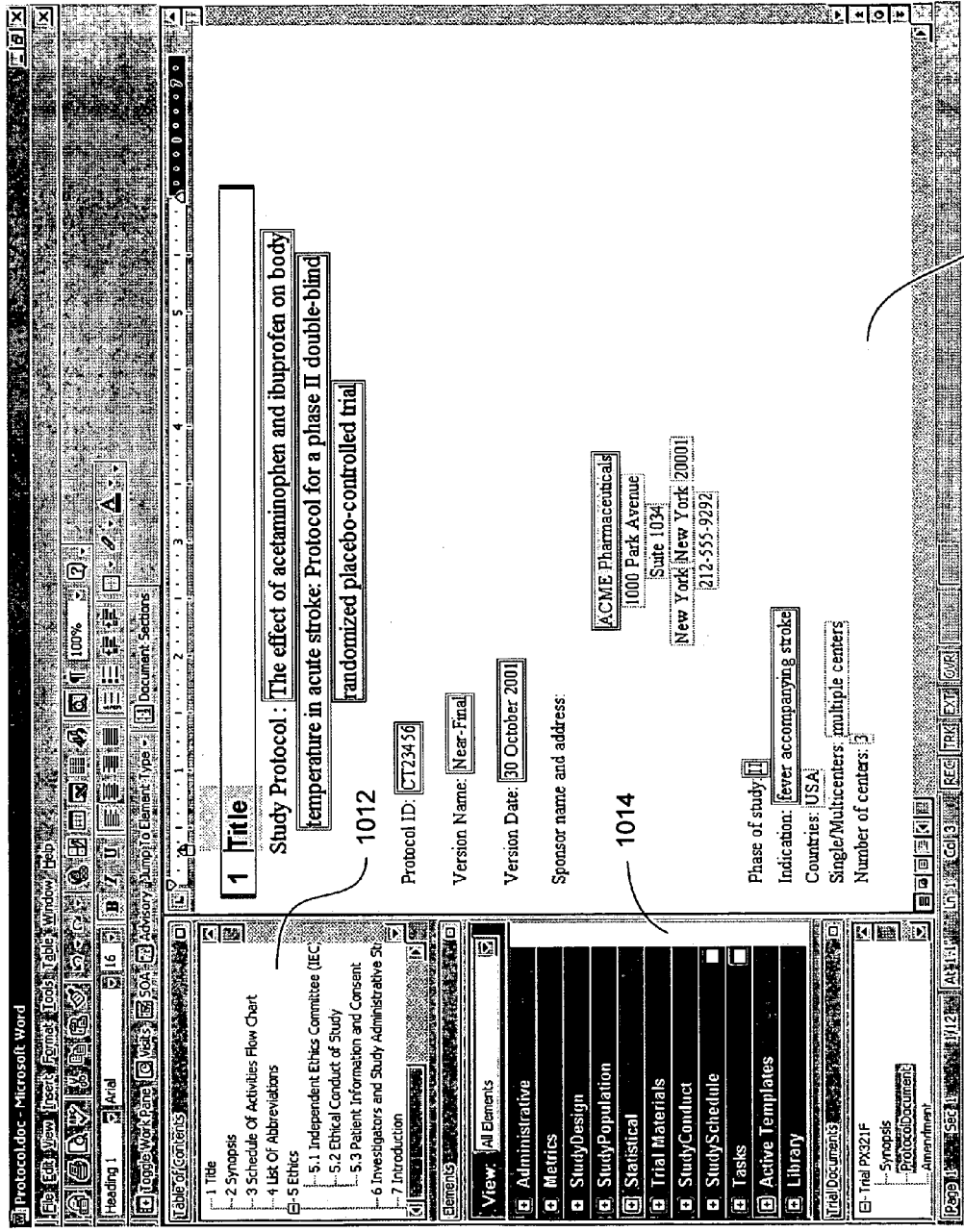
FIGS. 10, 13, 14, 15, 16, 26, 27, 28 and 44 are mockups of GUI screens produced by the protocol design tool of FIG. 1.

FIG. 10 is a mockup of a GUI screen produced by the protocol design tool 110 for the creation of a sample protocol. It contains a number of panes described as follows. Pane 1012 is a navigation pane which shows the document sections. These document sections are provided by the iCD template 120 of the iCD model 116 that was selected in step 914. By clicking on a section name, the user can navigate to a corresponding section in the dynamic document creation window. Only document sections and subsections currently in use in the document are available in pane 1012. The user can delete sections or add new sections through the use of a dialog described below with respect to FIG. 13, although removing a section that according to the mapping specification 118 is required, may generate a warning.

Pane 1014 is an element chooser pane, which is a unified list of all trial elements that the sponsor design group has chosen to expose to the user. The organization of elements in the chooser pane 1014 is completely configurable by the sponsor design group by appropriate definition in the mapping specification 118, but typically they are aggregated into logical topic groups and sub-groups. If so configured in the mapping specification 118, elements listed in the element chooser pane 1014 are available to the designer for insertion anywhere in the document being created; multiple instantiations of element references in the document are linked back to the iCP element itself, thereby promoting consistency of terminology throughout the document.

The chooser elements in pane 1014 can in certain embodiments include a number of status markings. One such marking might indicate that an element is in use in the iCP instance 122 but not in the iCD instance 130. Another such marking might indicate that the element is required for this document type by the mapping specification 118, but is missing from the iCD instance. Yet another such marking might indicate that the element is referenced in the document, but has not been assigned a value.

Pane 1016 is the document pane, and is the window within which the iCD instance 130 is shown. The document pane 1016 is essentially a Microsoft Word editor having certain additional features. Conventional MS Word behaviors can be used to edit any of the pre-specified fixed text in the document unless specified by the iCD model 116 as being not editable. In addition, special visual markings appear in the document pane 1016 to indicate iCP element references. Such markings visually highlight elements that are required according to the iCD model 116 but have no value, elements that are not required but have no value, elements that are required and have a value, and elements that are required and have a fixed and not editable value.

Figure 13:
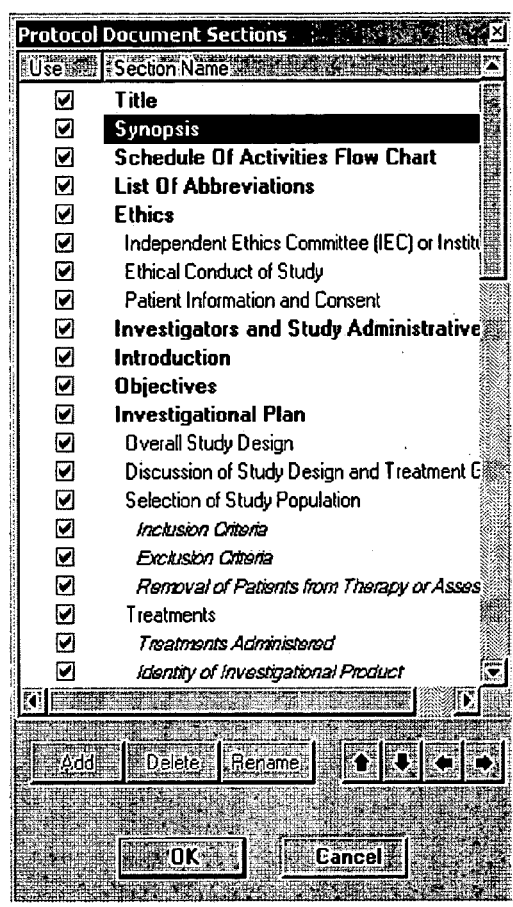

Manipulation of document sections can be accomplished in the protocol design tool 110 through the use of a "list of document sections" dialogue. A mockup for an embodiment of this dialogue is shown in FIG. 13. The dialogue shows a list of available document sections, including hierarchical subsections, and an indication of which sections are currently in use in the document. In one embodiment, the sponsor design group can specify in the iCD model 116 that certain sections are required, and in that case the dialog of FIG. 13 can also indicate which sections are required. The user is permitted to use this dialogue to add new user-defined sections anywhere in hierarchy, to delete sections unless they are required by the iCD model 116, to rename sections unless they are required by the iCD model 116, and to move sections around to the extent permitted by the iCD model 116. If the user checks a checkbox of a previously unused section, the protocol design tool 110 automatically adds the section to the document. If the user unchecks a section in this dialogue, in the protocol design tool 110 removes that section from the document. Removal occurs only after a warning if the document section contained element references that are required by the iCD model 116. Unchecking a section in this dialogue does not remove it from the list of available sections in this dialogue; the user can re-add the section by re-checking the in-use checkbox. The user can also add a new user-defined document section (not defined in the iCD model 116) at any place in hierarchy using this dialogue, and can also delete a document section from the list in this dialogue. Again, if there are required elements in a section being deleted, then the user is warned before deletion.

Figure 14:
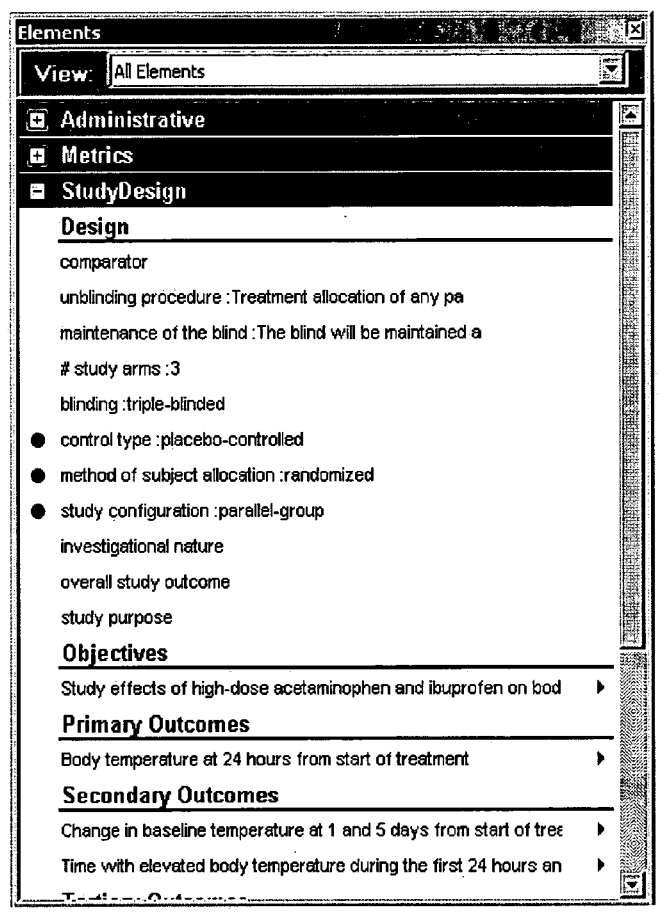

In the element chooser pane 1014, it can be seen that 11 top level topic groupings (sometimes called element tabs) are shown. FIG. 14 shows the chooser pane 1014 with the "StudyDesign" tab expanded. Other kinds of elements can be included in the chooser in other embodiments, and/or grouped differently, since as mentioned, the chooser pane is completely configurable in the mapping specification 118. Each section can be defined in the mapping specification to exhibit its own behaviors for entering new information into the iCP and for linking elements into the document. In addition, elements of the iCP instance 122 may appear in more than one group or sub-group in the chooser, and they may be organized differently in the chooser than their organization in the iCP instance 122.

Figure 16:
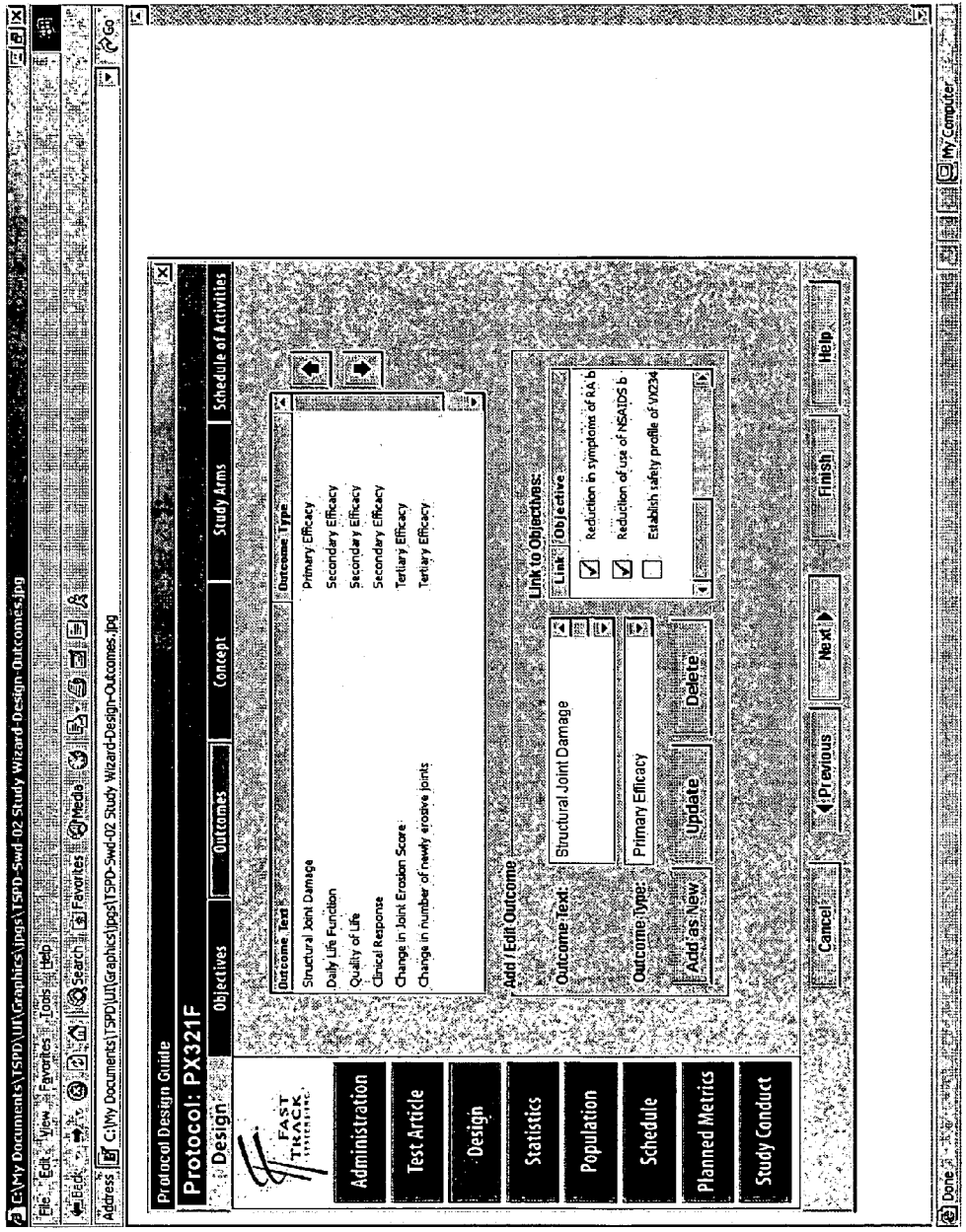

In the embodiment of FIG. 10, the StudyDesign tab of chooser pane 1014 includes sub-topics (not shown) for various kinds of patient outcomes (also sometimes referred to herein as endpoints) that might be referred to in the protocol. The mapping specification 118 specifies that the contents of these sections (i.e. the elements they represent in the iCP instance 122) can be edited by the user only through a specified workpane. FIG. 16 is a mockup of such a workpane. In this workpane, the user can define the different patient outcomes, using names to meet standard terminology within the company if desired. Each outcome is specified as being of one of several available types enumerated in the mapping specification 118; outcomes of types Primary, Secondary and Tertiary Efficacy are in use as shown in FIG. 16. The dialog also provides list of currently defined study objectives, and allows the user to link each outcome to one or more of such objectives by clicking in an associated check-box. Outcomes entered in the dialog of FIG. 16 will appear in the appropriate subsections in chooser pane 1014 after the user exits the dialog, and they are then available to be selected and inserted wherever they need to be referenced in the document being developed. Since all references in the document to a given outcome refer back to the same iCP element, consistency of term usage throughout the document is promoted since the outcome will always appear by the same name.

The tasks section of the chooser pane 1014 provides one method for accomplishing step 922 (FIG. 9) of selecting tasks for the iCP 122. In an aspect of the invention; step 922 takes advantage of a historical database 920 of clinical trial protocols, providing at least two advantages. First, reference to such a database helps the user/designer double-check that the procedures that the designer wants to use are common for the particular type of study that is being designed. Second, it helps the designer double-check that all relevant tasks have been included. Neither of these criteria are absolutes in the present embodiment the designer is free to deviate from past history if appropriate for the particular protocol being designed. But having the database available can help the designer avoid unintentional under- and over-inclusion of tasks.

In addition, it can be appreciated that a major cost component of clinical trials is negotiated investigator costs. Using clinical knowledge, results from previous studies and regulatory requirements, a protocol designer currently has much latitude in selecting the type and frequency of study measurements. Often the designer does not, however, consider the impact on study complexity and cost implied by the inclusion of a particular task in the study's schedule of activities (SOA). Although cost should never preempt scientific necessity, designers sometimes call for a particular kind of test when a less expensive but equally satisfactory test might be available. Also, there is significant quantitative evidence of procedure inflation—the progressive accumulation of excessive data collection that ultimately provides no useful additional information in the final regulatory dossier. Accordingly, the database 920 also includes an approximate cost benchmark for the tasks it contains, or many of the tasks it contains, and the protocol design tool 110 allows the designer to take advantage of these cost benchmarks as well. These cost benchmarks might represent the historical median cost of the procedure, for example, and can be useful in prompting thoughts about the cost implication of choosing a particular procedure. The cost benchmarks in the database 920 do not necessarily indicate the actual cost that will be incurred per administration of the particular procedure, but they can nevertheless provide a relative guideline.

In an embodiment, therefore, the historical database 920 contains an industry standard procedure list, such as the International Classification of Diseases, v.9, Clinical Modification (ICD-9-CM), incorporated by reference herein. The list is organized hierarchically by major therapeutic area, then by an intermediate level grouping of clinical indications within a major therapeutic area, and then by individual clinical indications at the lowest level of the hierarchy. For each clinical indication, the database identifies all the clinical trial protocols for the indication and the dates on which they were authored (or other associated dates). The database also identifies most of the individual procedures that were included in each protocol. Finally, the database also includes a sub-database that identifies cost benchmarks for such procedure.

Opening the tasks section in element chooser pane 1014 causes the system to reference the historical database 920. Instead of offering the entire list of available procedures, the protocol design tool 110 allows the designer to filter the list according to a number of criteria. For example, the designer can limit the list to only those tasks that have been associated with clinical trial protocols dated within a specified time window, such as during the past 36 months. As another example, the designer can limit the list to only those tasks that have been associated with clinical trial protocols for one or more specified clinical indications and/or study phases (such as the study indication and phase selected in steps 910 and 911 (FIG. 9)). In an embodiment (not shown) the designer can select desired indications by checking or unchecking items at any level of a hierarchically organized list of clinical indications presented by the protocol design tool 110, thereby allowing the designer to select indications for filtering purposes individually, by major therapeutic area, or by intermediate level grouping. Alternatively, or additionally, the designer can specify clinical indications using a text-based search in the database 920.

Figure 15:
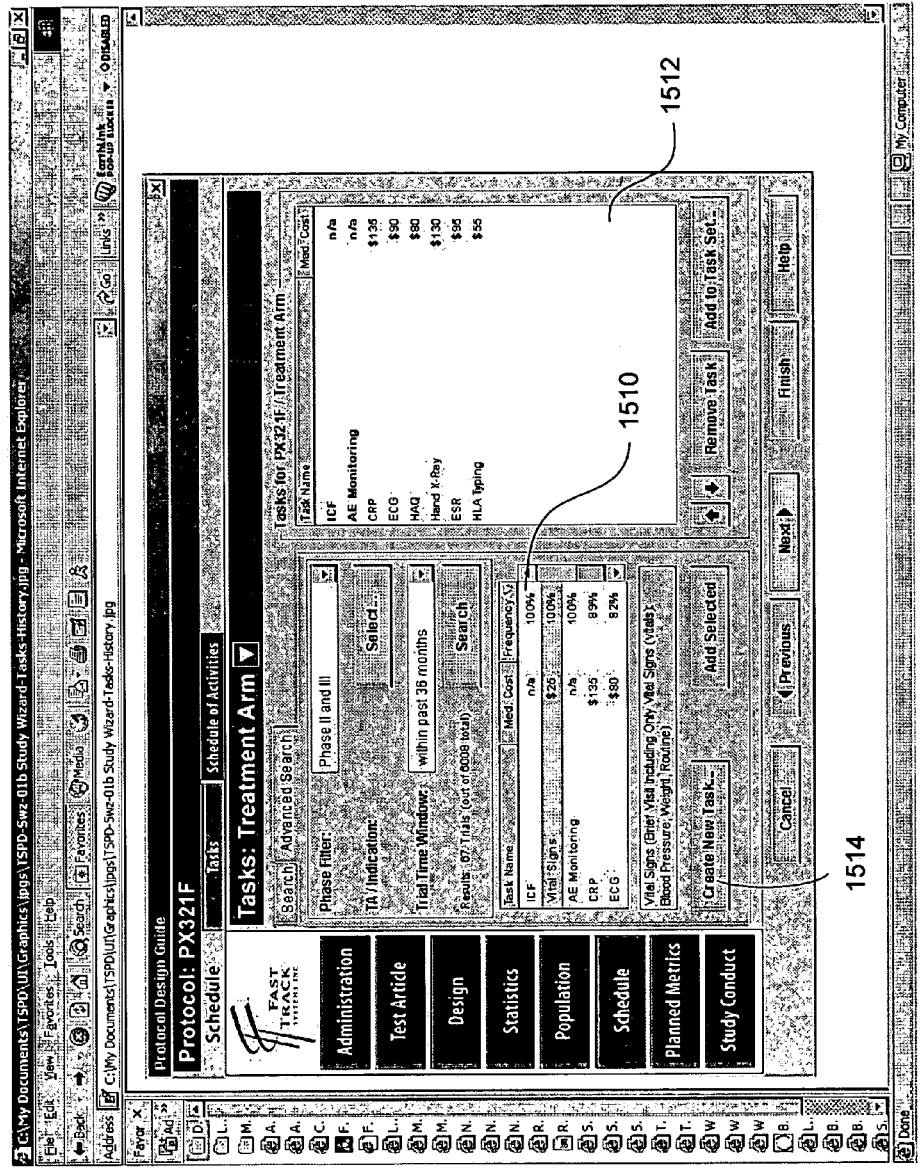

Once the designer has specified filtering criteria, the protocol design tool 110 suggests to the user the list of tasks from the database 920 that satisfy the filter criteria. FIG. 15 is a mockup of a dialog showing the suggested task list in pane 1510. From this list, the user can choose desired tasks for inclusion in the new protocol. The list of tasks chosen so far is shown in pane 1512 in FIG. 15. As can be seen, the lists in panes 1510 and 1512 both include the cost benchmark from the database 920 for each task. In another embodiment, the cost benchmarks might be shown only in one or the other of such panes. The designer can also create new tasks via a control 1514 in the dialog of FIG. 15, which are not necessarily represented in database 920.

In an embodiment, tasks in database 920 are not offered to the designer in this dialogue if their association with previous clinical trial protocols does not meet certain association strength criteria. For example, in one embodiment, the association strength criteria might exclude all tasks that are indicated in the historical database 920 as having been associated with no more than some predetermined percentage of previous clinical trial protocols for the same indication and trial phase as the protocol being designed. In another embodiment, the association strength criteria might exclude all tasks that are indicated in database 920 as having been included in no more than a predetermined percentage of previous clinical trial protocols that satisfy the user-specified filtering criteria. In another embodiment, the association strength criteria might exclude all but the N most commonly occurring tasks (N>0) in previous clinical trial protocols represented in database 920 for the same indication and trial phase as the protocol being designed. In yet another embodiment, the association strength criteria might exclude all but the N tasks indicated in database 920 as having been most frequently included in previous clinical trial protocols that satisfy the user-specified filtering criteria. Many other association strength criteria, and combinations thereof, can be used in various embodiments. The protocol design tool 110 might also exclude tasks for other reasons, such as for protecting the proprietary information of companies or sponsors of individual protocols in the database 920.

The StudySchedule section of chooser pane 1014 provides associated shortcuts to two workpanes (not shown), EventSchedule and ScheduleOfActivities. The EventSchedule entry provides access to one method for accomplishing step 928, defining the event schedule. As mentioned, events identified in the iCP and iCD are not required to involve face-to-face patient visits, and the use of the term "visit" herein is merely a convenience. The term "visit", is used interchangeably herein with the term "event", and is intended to include any event that the designer wishes to identify in the protocol.

Figure 26:
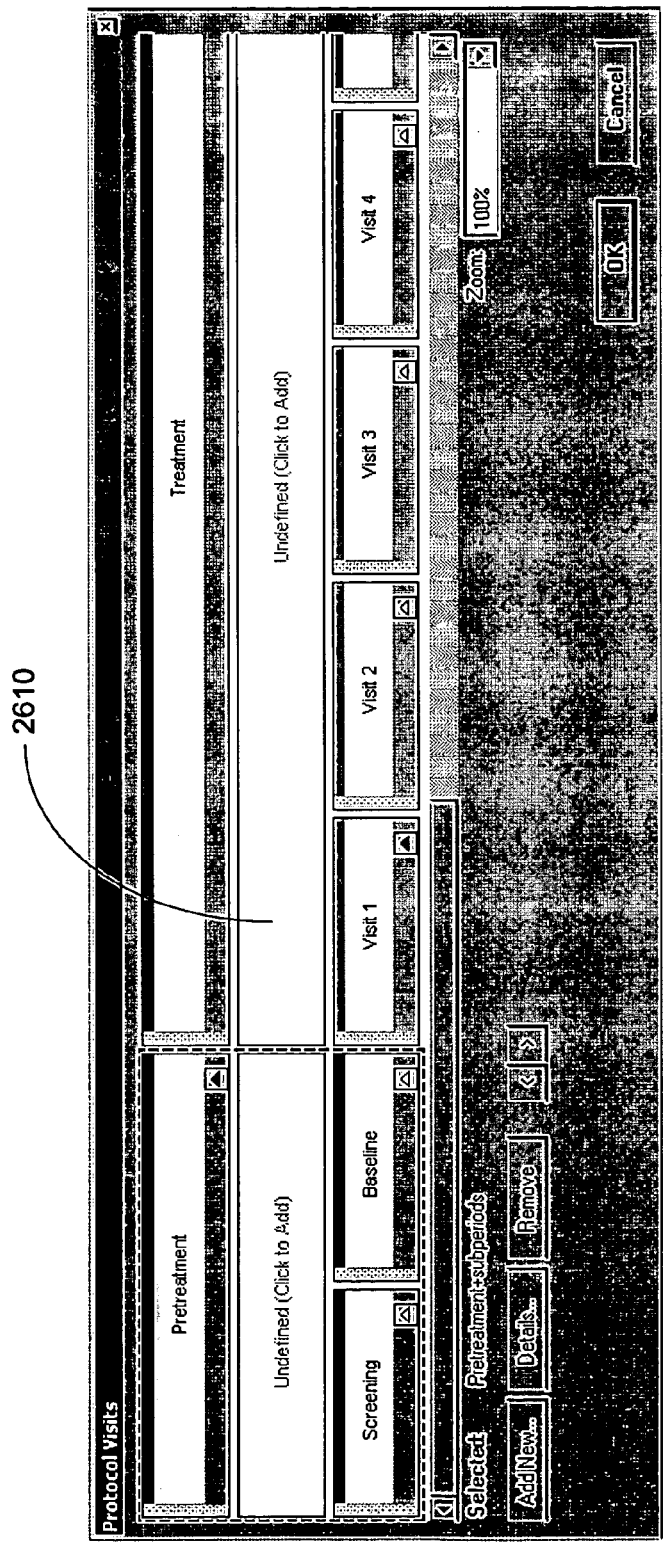

FIG. 26 is a mockup of a workpane presented by the protocol design tool 110 for defining or editing the event schedule. As can be seen, the event schedule workpane can be used to build a list of events, periods and optional sub-periods for the protocol workflow. No sub-periods are shown in FIG. 26, but a row 2610 is provided in which they would appear. The work pane functions like a grid, with each box representing an event. Unlike a grid, selection of a parent will also select its children, so in this way it functions like a tree control. Each event can be inspected, edited or deleted, and the state of whether it contains detail text is indicated by an icon. Also indicated is whether the event is locked, due to being specified by the iCD model as being fixed, required and uneditable. Additional icons can be used to indicate repeating events and error states. Each event has both a full name and an abbreviation. The full name is used in the work pane of FIG. 26, and the abbreviation is used in the SOA (schedule of activities) table.

Figure 27:
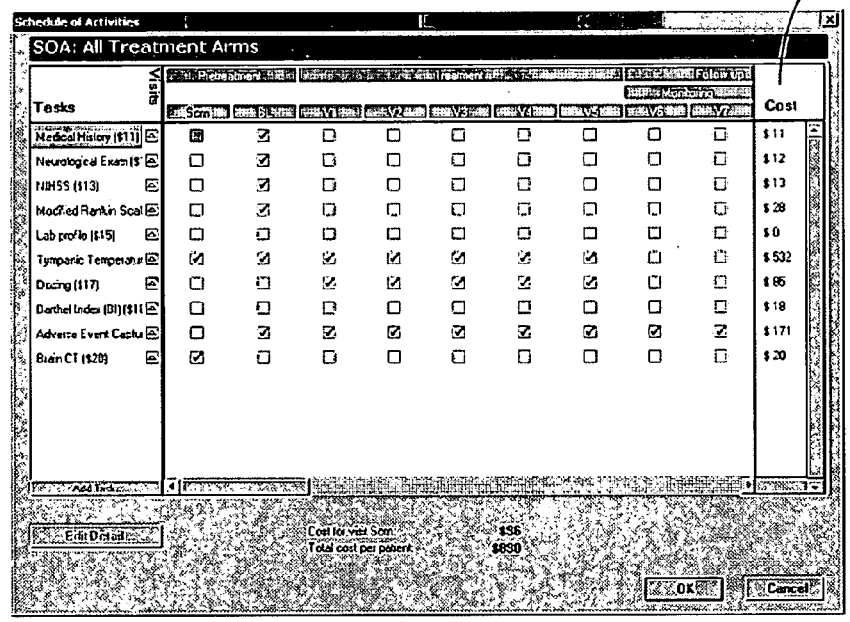

The ScheduleOfActivities entry in the StudySchedule section of the chooser pane 1014 provides access to one method for accomplishing step 930 (FIG. 9) of linking task objects to event objects. In particular, it provides access to an SOA workpane such as the mock-up shown in FIG. 27. As can be seen, the work pane is organized to show the SOA in tabular form. Along the horizontal dimension of the table, columns are identified by their abbreviations. The hierarchically related groupings of events are shown as well in the horizontal dimension. Along the vertical dimension each of the tasks chosen in step 922 are identified, together with their relative cost indications. By placing check marks at individual crossings in the table grid, the designer is able to associate individual ones of the tasks with individual ones of the events. If the user selects a particular visit (column), then the work pane shows the relative cost per patient for that visit. The work pane also shows in column 2710 the total cost per patient over all visits, resulting from the inclusion of each individual task in the study. Other user behaviors will also show the relative cost per patient resulting from inclusion of an individual task in a particular visit. The total relative cost per patient occasioned by the designer's task visit associations is shown as well. As with other data entry work panes in the present embodiment, changes are not made in the iCP instance 122 or in the iCD instance 130 until the user evidences a commit behavior, such as clicking on an OK button. The screen shot of FIG. 27 shows a single SOA for all treatment arms of a study. For a multi-arm study in which different arms require differing assessments, separate tables such as that of FIG. 27 are available to the designer.

Figure 28:
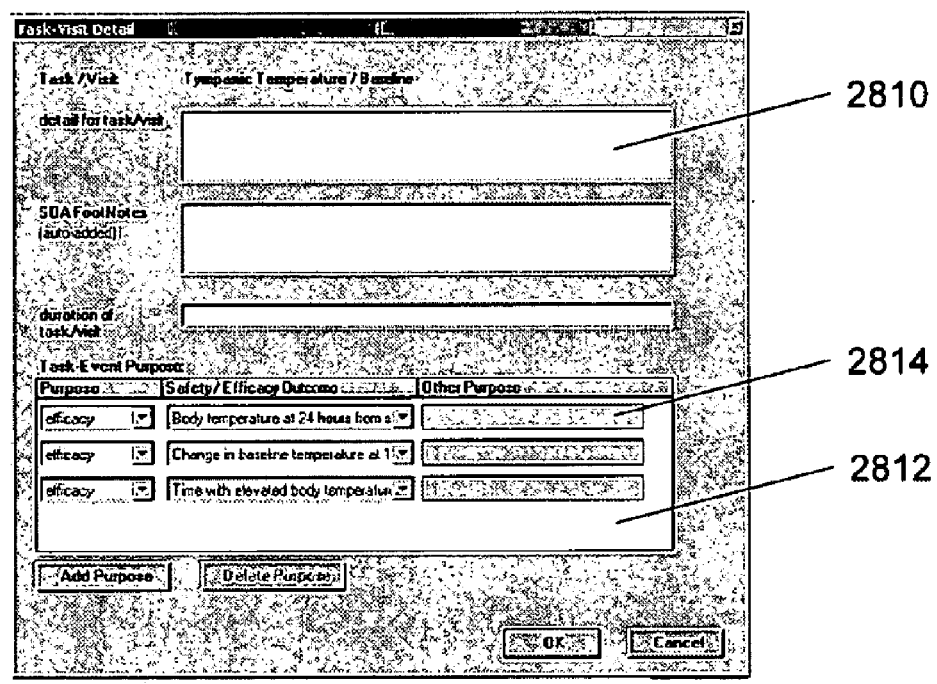

FIG. 28 is a screen shot mockup of an example SOA cell detail data entry dialog. As can be seen, it includes a field 2810 for entering detail text, and also includes a region 2812 for entering task-event purposes. The user may enter one or more purposes here, but in one embodiment the system requires (either immediately or by a subsequently applied advisory rule, described below) that at least one purpose be entered for each task-visit combination. In an embodiment, the list of available purposes includes safety, screening, efficacy, treatment and other. If the user selects other, then the system allows (or in one embodiment requires) the user to enter a text description of that purpose in field 2814. If the user selects efficacy as the purpose, then the system allows (or in one embodiment requires) the user to identify at least one outcome from the list of outcomes that have been defined in the iCP instance 122. The user can enter an outcome also if the selected purpose is safety. The data items illustrated in FIG. 28 are written into respective fields of a taskVisit object in the iCP 122 which links the task to the visit, or into a TaskVisit-Purpose object in the iCP0122 which links to the TaskVisit object.

Dynamic Templates

As mentioned, the protocol design tool 110 provides dynamic templates (also sometimes called macros or macro procedures) that can automate the insertion of complex content into the document instance 130. The generated content can contain multiple references to data elements in the ICP as well as mixed text and footnotes. These procedures exploit the relationships between protocol data elements to express important concepts in the trial's underlying design. For instance, a dynamic template could document the fact that a particular outcome was being determined by certain assessments on certain visits.

Two examples of such dynamic templates will now be described. These templates implement step 934 (FIG. 9) of instantiating an SOA table in the document instance 130, and step 936 of instantiating an SOA narrative into the document instance 130.

The following is a pseudocode description of the procedure executed by the SOA Table insertion dynamic template:

```
for every schedule object
  create a Dynamic Template element in the document
  insert two section breaks within the document
  create an empty table between the two section breaks
  create an empty column
    for every period in the schedule ordered by period.sequence
      create a column containing the text in period.displayname
      if (period.SOA footnote exists) create footnote reference for this
      period in this cell
      if (period.subperiods > 0)
        in a new row in the context of this column
          for each subperiod in period ordered by subperiod.sequence
            create child-column for each subperiod containing the
            text in subperiod.displayname.
            if (subperiod.SOAfootnote exists) create a footnote
            reference for this subperiod in the cell
            in the context of this column
              for each visit in subperiod ordered by visit.sequence
                create child-column containing the
                vist.displayname and visit.timewindow
                if (visit.SOAfootnote exists) created a footnote
                reference for this visit in the cell
              next visit
          next subperiod
      else
        in a new row
          in the context of this column
            for each visit in period ordered by visit.sequence
              create column containing the vist.displayname and
              visit.timewindow
              if (visit.SOAfootnote exists) created a footnote
              reference for this visit in the cell
            next visit
    next period
  starting at the last initialized row (containing Visits) create new row
  in column 1 put "Study Timepoint"
  for each visit
    put visit.studyTimepoint
  next visit
```

```
create a new row
init taskcounter to 1
for each task
  create new row
  put task[taskcounter].displayName in first column
  if (task[taskcounter].SOAfootnote exists) put a footnote reference
  to this task in the cell
    for each visit column
      if (exists taskvisit for task[taskcounter] and
      visit[column])
        put an "x" in the visit column
        if (taskvisit.SOAfootnote exists)
          add footnote reference to this taskvisit in
          this cell
    next visit column
    taskcounter++
  next
next schedule
Insert footnotes below grid in order of creation
```

FIG. 45 is an image of a sample SOA table produced in the document in accordance with the above dynamic template.

The following is a pseudocode description of the procedure executed by the SOA Narrative insertion dynamic template.

```
Insert Dynamic Template element in the document..
Insert the following into the Dynamic Template element's region...
For each Period in the Schedule
  Print "Period " + putElementRef(Period.displayName) + " (Duration is "
  +
  putElementRef(Period.SOADetail.duration) + ")\n"
  Print putElementRef(Period.SOADetail.miscDetail) + "\n"
  For each ScheduleItem in Period
    if (ScheduleItem isA SubPeriod)
      indent
      Print "<bullet> Subperiod " +
      putElementRef(ScheduleItem.displayName) +" (Duration is " +
      putElementRef(SubPeriod.SOADetail.duration) + ")\n"
      For each Visit in (SubPeriod)ScheduleItem
        indent
        Print "<bullet>Visit " +
        putElementRef(Visit.displayName) + " ( " +
        putElementRef(Visit.studyDayOrTime) + "} (" +
        putElementRef(Visit.permittedTimeWindow) + ") " +
        putElementRef(Visit.SOADetail.miscDetail) + "\n"
        indent
        For each TaskVisit.where TaskVisit.visitID = Visit.ID
          Get Task where Task.ID = TaskVisit.taskID
          Print <bullet> putElementRef(Task.displayName) +
          "Personnel: this task should be performed by " +
          putElementRef(TaskVisit.whoPerfoms) + "\n"
        Next TaskVisit
      Next Visit
    else // ScheduleItem is Visit
      Print "<bullet>Visit " + putElementRef(Visit.displayName) + "
      ( " + putElementRef(Visit.studyDayOrTime) + "} (" +
      putElementRef(Visit.permittedTimeWindow) + ") " +
      putElementRef(Visit.SOADetail.miscDetail) + "\n"
      indent
      For each TaskVisit where TaskVisit.visitID = Visit.ID
        Get Task where Task.ID = TaskVisit.taskIK
        Print <bullet> putElementRef(Task.displayName) +
        "Personnel: this task should be performed by " +
        putElementRef(TaskVisit.whoPerfoms) + "\n"
      Next TaskVisit
    endif
  Next ScheduleItem
Next Period
```

FIG. 46 is an image of a sample SOA narrative produced in the document in accordance with the above dynamic template.

A number of other dynamic templates can also be defined for insertion of generated content into the document. One additional example is for the insertion of an Efficacy Assessment Listing, which after some header text, inserts a bulleted list of all tasks and their detail (if available) and task durations (if specified) used during the study that are used for efficacy for at least one visit. Order is preserved as specified in the schedule of activities. The text generated by this dynamic template is protected from uncontrolled user edits. The following sets forth rough logic that can be used to implement an Efficacy Assessment Listing dynamic template. In this description, data elements shown between angle brackets (< >) are instantiated in the document as element references rather than text.

- Go through all the instances of <taskVisit>s in the iCPInstance. For each one, if it has a TaskVisitPurpose element whose purposeType has a type of "efficacy" then add the taskId and value of the instanceLabel of the Task object pointed to by the taskId element of that TaskVisit to the result-list. If it is already in the result list, do not add it again. By the end, this will create a list of unique taskIds and their descriptions in result-list.
- Order result-list so that it mirrors the order that the tasks are in the SOA table. Then insert into the document the header text for the generated content and then a bulleted list of tasks in the established order, where each is task name is followed by its task detail (if present), and then by its duration (if present).

Another example dynamic template generates a Safety Assessment Listing, which inserts into the document some header text followed by a bulleted list of all tacks and their detail (if available) and task durations (if specified) used during the study that are used for safety during at least one visit. The order as specified in the schedule of activities is used. The following sets forth rough logic that can be used to implement an Efficacy Assessment Listing dynamic template. In this description, data elements shown between angle brackets (< >) are instantiated in the document as element references rather than text.

- Go through all the instances of <taskVisit>s in the iCPInstance. For each one, if it has a TaskVisitPurpose element whose purposeType has a type of "Safety" then add the taskId and value of the instanceLabel of the Task object pointed to by the taskId element of that TaskVisit to the result-list. If it is already in the result-list, do not add it again. This will create a list of unique taskIds and their descriptions in result-list.
- Order the result list so that it mirrors the order that the tasks are in the SOA table. Then insert into the document out header text for the generated content and then a bulleted list of tasks in the established order, where each is task name is followed by its task detail (if present), and then by its duration (if present).

Another example dynamic template generates an Experimental section which inserts into the document a list of study objectives and certain details relating to the objectives. The text generated by this dynamic template is protected from uncontrolled user edits. Rough logic to generate an Experimental section for the document is as follows, in which again, data elements displayed in angle brackets (< >) are instantiated in the document as element references rather than text. In addition, any element reference that does not have a value it and its associated text is not displayed.

For each Objective in Design.Objectives that has type of Primary do:
    Print "The primary objective stated as: "<Objective.statement>", will be established by the following outcome measures: "
        For each Outcome in Objective.associatedOutcomes, print
            <Outcome.statement> "as measured by"

-continued

For each Outcome.asMeasuredBy (a TaskPurpose) print
            TaskPurpose.taskId.displayName "performed on Visits "
            Get all the visits for which there is a TaskPurpose with this same TaskId and the same purposeType and print bulleted list of their displayNames. The visits are displayed in a sorted order based upon the comparative order of the visit's grandparent period sequence, visit's parent subperiod sequence, and visit's sequence; if there is no subperiod in the ancestral hierarchy, then its comparative value is –1.
For each Objective in Design.Objectives that has type of secondary do: <same as above>
For each Objective in Design.Objectives that has type of tertiary do: <same as above>
The text "performed on visits:" and "as established by the following outcome measures:" is adjusted for plurality of items in its associated list.

Another example dynamic template generates a Study Design section which inserts into the document certain basic information about the study design. The text generated by this Dynamic Template is protected from uncontrolled user edits. Roughly, the following is inserted into the document by this dynamic template (angle bracketed elements are instantiated as element references rather than text, and all element references are displayed regardless of whether there is associated data or not):

Study <ProtocolSkeleton.protocolId> is a <ProtocolSkeleton.is Multicentered>, <Design.methodOfAllocation>, <Design.masking>, <Design.studyConfiguration> <Design.controlType> trial of approximately <Metrics.plannedEvaluableSubjCount> subjects with <ProtocolSkeleton.indication>, with a treatment duration of <Metrics. plannedTreatmentDuration>.

Example content inserted into a document by this dynamic template might be:

"Study B1234 is a multicenter, randomized, double-blind, parallel-group, placebo-controlled, trial of approximately 900 subjects with hypertension, with a treatment duration of 40 weeks."

Once protocol content has been generated and inserted into a document it is desirable that it be kept synchronized with the content of the iCP when changes are made to the study design. While some changes are automatically reflected through the embedded protocol references, there are some types of changes, such as when new object instances or relationships are created, that could require additional element references to be generated in the text. The protocol design tool 110 has a mechanism to ensure that this form of synchronization can be accomplished automatically. This feature is called Auto Execution of the Dynamic Templates.

According to this feature, wherever a Dynamic Template is executed in a document instance, an XML container element (A Macro Element) is created that remembers the location of the generated content. There can be multiple such areas in the document generated by one or more Dynamic Templates. As text is inserted or removed from the area above a generated region, the XML plugin and Microsoft Word ensure that the apparent location of the element region in the document always surrounds the correct content.

Figure 44:
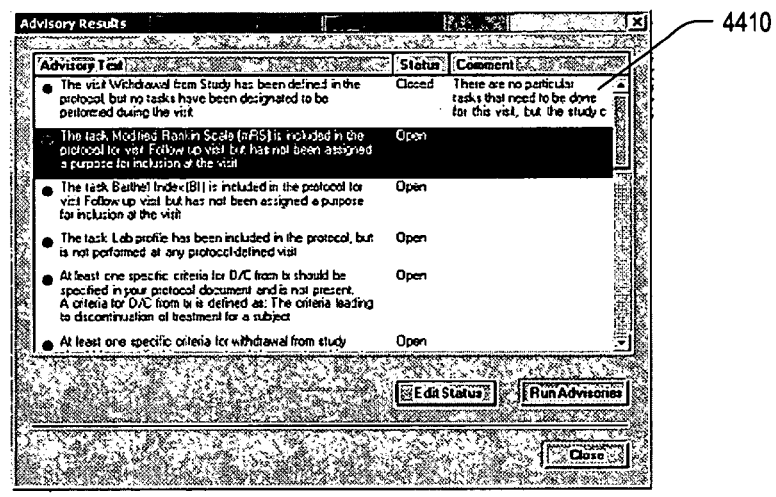

The iCP infrastructure is aware of changes made to it by any application components and is capable of automatically re-executing all of the dynamic templates used in the document. The protocol design tool 110 launches this process whenever the lowest level work pane has been closed with an affirmative signifying a commit action. At this point, a number of changes to the iCP instance 122 may have been accumulated as selections were made and accepted in the stack of possible work panes. As the last work pane in the stack is closed, the changes are now propagated into the official or base-level iCP instance and will become part of the persistent record. After this request has been fulfilled, the Dynamic Template executor regenerates all the content regions using the following algorithm:

Refresh Element Cache from Document
Foreach Dynamic Template Element In Cache
    Get function type from Element
    Get function name from Element
    Get region offsets In Document from Element
    Collapse region to zero length
    If functionType is VBA
    Run functionName, params, at offset.start
    Else if functionType is CSHARP
    Load dll where functionName exists
    Run functionName, params, at offset.start
Next Region
Stop document redraw
For each ElementReference
    Find elementPath in element
    Lookup value at elementPath in iCP
    If (not value equals currentValue in document)
    Copy icpValue into currentValue in document
    End If
Next Reference
Redraw document Protocol Advisory Service At any time during the development of the protocol, the designer can invoke the protocol advisory service 134 (FIG. 1) in order to identify elements that have not yet been created, or elements that have been created but not yet inserted into the document, or elements that have been created but not yet completed, or to look for patterns among data elements that do not adhere to guidelines or otherwise can cause problems. In one embodiment, the protocol advisory service evaluates a number of different rule sets, either sequentially or in parallel, to identify advisories. These include rules to identify a visit object with no tasks assigned, a task with no purpose assigned, a task that has not yet been assigned to any visit, a study outcome that is not been assigned to any task (every outcome should include an asMeasuredBy attribute that points to at least one TaskVisit object or (in another embodiment) at least one TaskVisitPurpose object), and elements that are missing or unreferenced in the current document instance. In many cases, a single advisory rule can produce many advisory instances when evaluated; this will occur when a rule is general and targets a class of elements, and more than one element instance is found that satisfies the condition being tested. The protocol advisory service 134 produces a list of advisory instances identified, in some embodiments organized by advisory type. An example of a list of advisory instances is illustrated in the screen shot mock-up of FIG. 44. The designer can refer to this list and correct the instances identified using any of the data entry methods described previously. Once corrected, an advisory instance will no longer appear in this list after the designer reruns the protocol advisory service 134. The designer can close (choose to ignore) an advisory instance, but only if a justification is entered in a text field corresponding to the advisory instance. The advisory result list of FIG. 44, for example, includes one advisory 4410 that is listed as "closed", with a justification set forth in the Comment column.

The "visit with no tasks" advisory identifies all visit objects in the iCP instance 122 with which no task objects have yet been associated. A separate protocol advisory object is created for each visit in the iCP instance 122 which satisfies this rule.

The "tasks unassigned to visit" advisory identifies the opposite: task objects that the user has created in the iCP instance 122, but which have not yet been linked to any visit object. There is no requirement that every task object in the iCP instance 122 be linked to at least one visit object, because for example the designer may have created the task object only for use in other document types related to the iCP instance 122. But an advisory of this sort nevertheless might help the designer correct an issue that was created unintentionally. In one embodiment, this rule can operate by searching the iCP instance 122 for task objects that have no associated taskVisit objects.

The "task without a purpose" advisory identifies all task objects in the iCP instance 122 that have been assigned to a visit, but for which the user has not identified a reason why that task should be performed in that visit (FIG. 28). In one embodiment, this rule can operate by searching the iCP instance 122 for all taskVisit objects in which the "purpose" field is null. Again, a separate protocol advisory object is created for each taskVisit instance identified by the rule.

The "outcome without assessment task" advisory identifies outcomes that the user has defined in the iCP instance 122, but which have not yet been specified as a reason for performing a particular task in a particular visit. Again, there is no requirement that every defined outcome be used anywhere, because for example some outcomes defined by the user and instantiated in the iCP instance 122 might be intended for inclusion only in other document types drawing from the same iCP instance 122. But an advisory of this sort might help the designer correct an issue that was created unintentionally. In one embodiment, this rule can operate by searching the iCP instance 122 for outcome objects that do not point to any TaskVisit or (in another embodiment) TaskVisitPurpose objects in the "asMeasuredBy" attribute.

Whereas the above four advisory types identify certain kinds of incompleteness by examining only the iCP instance 122, the "missing or unreferenced protocol elements" advisory examines both the iCP instance 122 and the iCD instance 130. This protocol advisory addresses issues with element handling in a document surrounding the breaking of rules for "requiredness" (the requirement that a document instance include at least one reference to an iCP element of a particular type), references in the iCD without values, and iCP values that are unused in the iCD.

The term "incompleteness" here refers to incompleteness of the document being created rather than incompleteness of the iCP database 122. As mentioned, mapping specification 118 defines, for a given document type, which sections must be included in the final document, and which kinds of data must appear in the document. The iCP instance 122 may well contain data objects (or attributes of objects) that never need to appear in a particular kind of output document. Thus this protocol advisory can often report completeness (find no problem) even when certain data objects or object attributes (such as those not needed for the document) in the iCP have not been assigned values. Conversely, the system of FIG. 1 does not necessarily instantiate objects in the iCP database 122 until the user instructs the system to do so in the course of authoring. Thus it is also possible for this protocol advisory to report incompleteness because the user has not yet made reference in the document to certain objects that the mapping specification 118 requires for completion of that document type, even though all data objects that have been instantiated in the iCP have been assigned values. Examples of elements that might be required by a mapping specification for a clinical trials protocol document type are as follows: an indication and phase, at least one objective, a sponsor, and a definition of evaluable patients.

The "missing or unreferenced protocol elements" advisory identifies four cases as follows:

Case 1: Missing required element reference; no existing values

Case 2: Missing required element reference; existing values

Case 3: Defined but unreferenced element value, element not required

Case 4: Referenced without value

Figure 29:
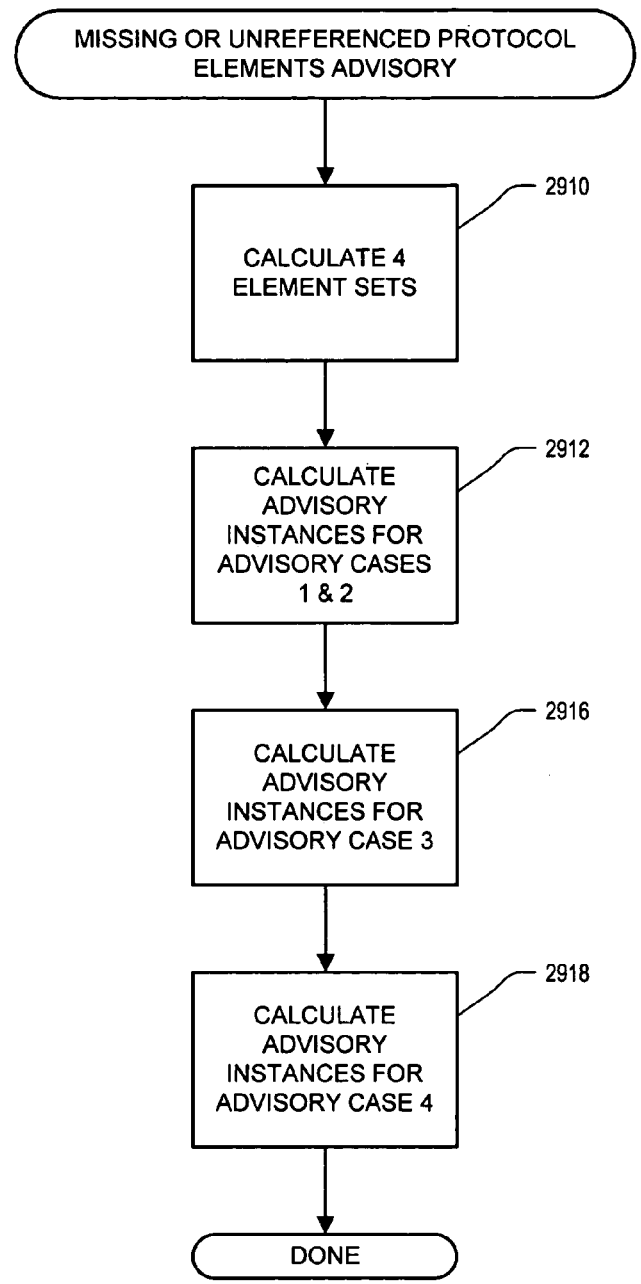
FIGS. 29, 30, 31 and 32 are flowchart illustrating methods for implementing certain advisories according to the invention.

In one embodiment, the search for advisories in the four cases can occur entirely separately and in sequence. In another embodiment, the search can be partially or completely combined. FIG. 29 is a flowchart illustrating a partially combined method. Very simply, as shown in FIG. 29, the method involves first calculating four element sets (step 2910), and then using these element sets to calculate the instances satisfying the four advisory cases. Cases 1 and 2 are calculated together in step 2912, and cases 3 and 4 are calculated thereafter in sequence in steps 2916 and 2918, respectively. The four sets calculated in step 2910 are as follows:

(A) iCP Val: Valued iCP elements. Instances of elements in iCP instance 122 that have values in the iCP instance. The elements of this set are identified by searching iCP instance 122 for all elements of all types, and excluding those with which no value has been associated (or which have a null value assigned).

(B) Required: Elements identified in mapping specification 118 as being "required" in documents of the kind currently being authored. Only simple elements are included in this set; elements of type "template" (complex elements that are made up with other elements) are excluded. The elements of this set are identified by selecting all chooser elements identified in the mapping specification 118 for which an ElementType attribute is not set to "template", for which a "doctype" attribute is set to "protocol", and for which a "required" attribute is set to true.

(C) Referenced: all element references in iCD instance 122.

(D) Referenced with value: all entries in set C which are bound to an iCP element that has a value assigned.

Figure 30:
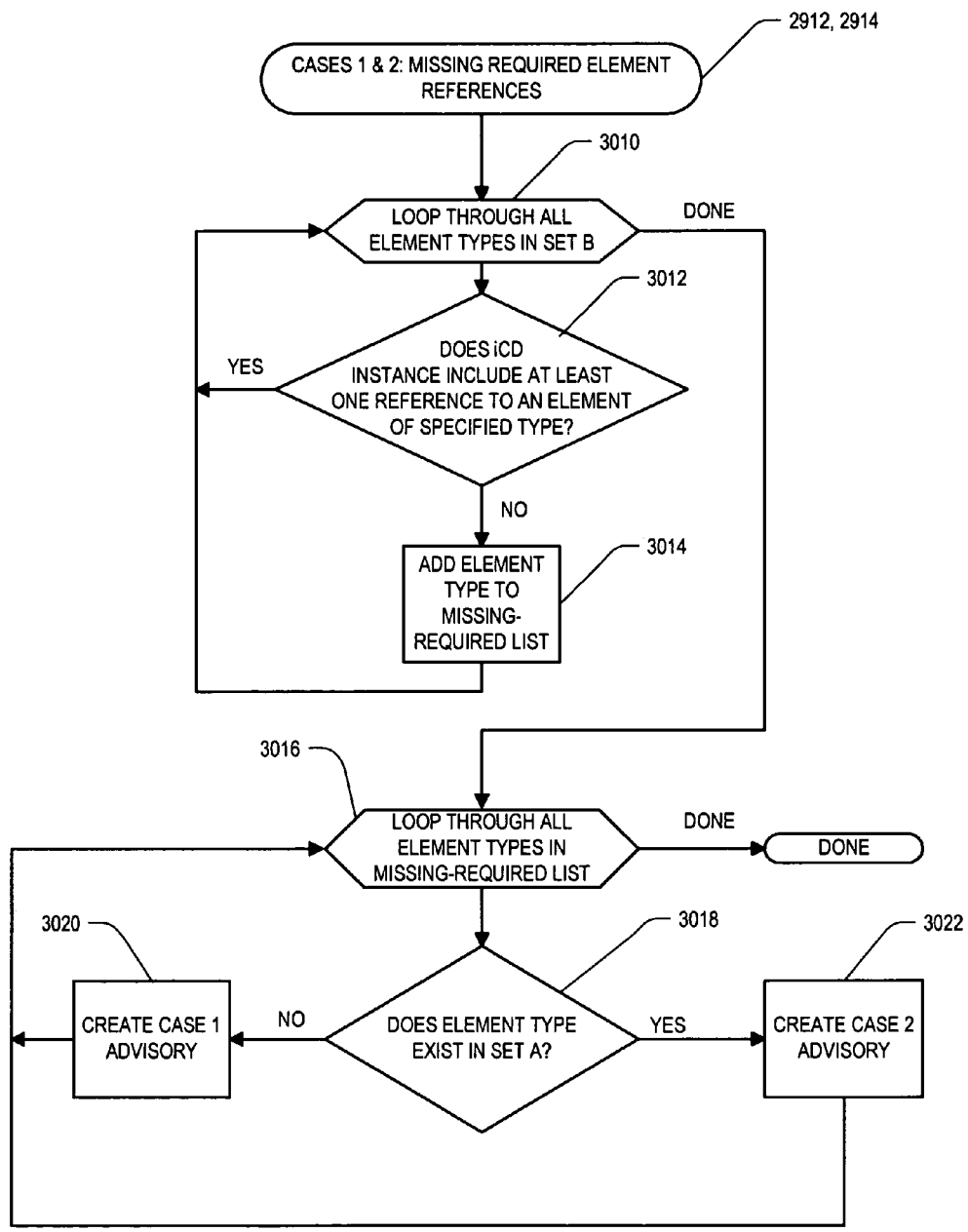

Once the above sets have been calculated, the advisory instances for cases 1 and 2 (step 2912) can be calculated as set forth in the flow chart of FIG. 30. First, in step 3010, the service 134 loops through all entries in set B (required elements as defined by mapping specification 118). Each such entry identifies an element type. In step 3012, the system checks for an element of the specified type in iCD instance 122. If one is found, then the required element exists and the routine loops to the next entry (step 3012). If not found, then in step 3014 the routine adds the missing element type to a missing-required list and returns to looping step 3010. When this loop completes, the missing-required list contains a list of all the element types that are indicated by mapping specification 118 as required in the document, but which have not yet been included.

In step 3016, the routine then begins a loop through all element types on the missing-required list for the purpose of determining which of two kinds of advisories should be used to report each missing element to the user. Thus in step 3018 the routine determines whether the element missing from the document instance has been assigned a value in the iCP instance 122. This determination is accomplished by determining whether the element exists in set A (iCP Val). If not, then in step 3020, the routine creates a case 1 advisory to inform the user of the element type that is required but not yet present in the iCD instance 122. A descriptive user tip is provided as well. If the element does exist at least once in set A (iCP Val), then some additional assistance can be offered the user. In particular, in step 3022, the routine creates a case 2 advisory to inform the user of the element type that is required but not yet present in the iCD instance 122, together with the user tip. The case 2 advisory then also lists the current values from set A of all elements of the same type that have values in iCP 122. After the advisory of case 1 or case 2 has been created, the routine then returns to looping step 3016 to consider the next element type in the missing-required list. Of course, while the loop 3016 to create case 1 and case 2 advisories is combined in the flowchart of FIG. 30, another embodiment can identify the case 1 and case 2 advisories in separate loops through the missing-required element list.

Figure 31:
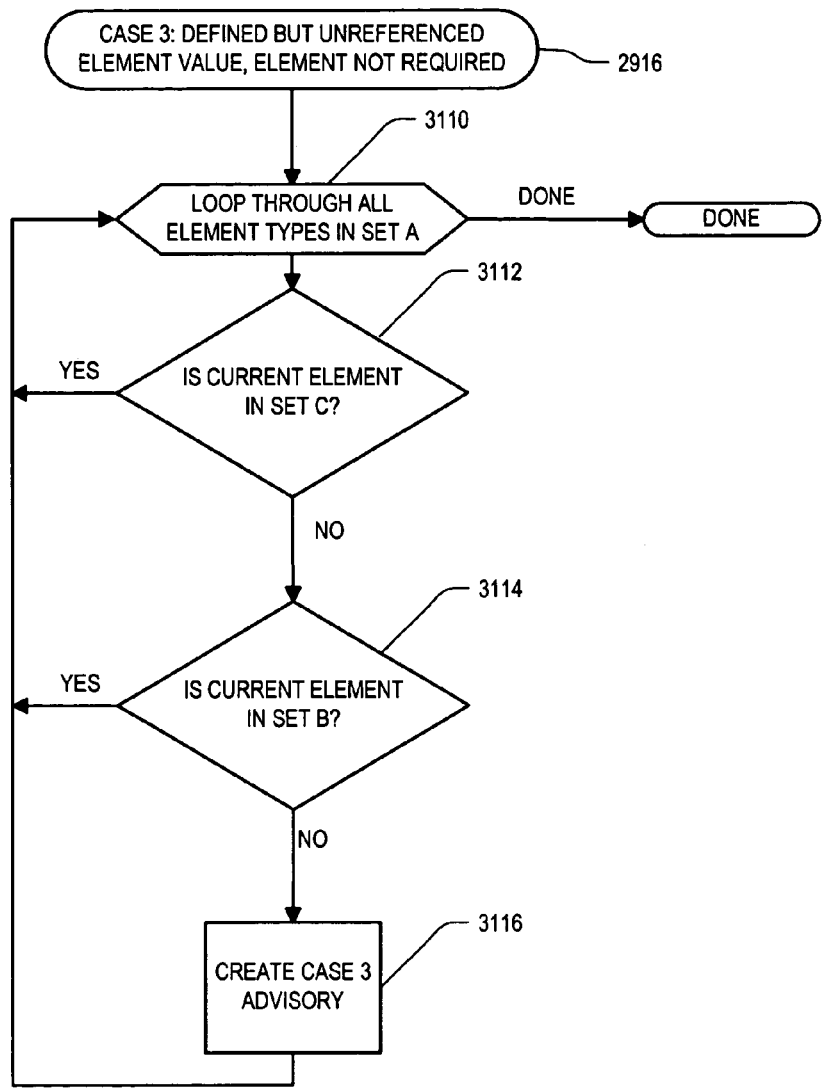

FIG. 31 is a flow chart illustrating how case 3 advisories can be identified using sets A-D above. Case 3 advisories identify elements that have been instantiated in the iCP instance 122 and for which a value has been assigned, but which have not yet been referenced in the document being created. Only elements that are not required by the mapping specification 118 are mentioned here. Referring to FIG. 31, in step 3110, the routine loops through all entries in set A (elements in iCP with values). In step 3112, if the current element is present in set C (referenced in the iCP instance 122), then the routine returns to looping step 3110 and no case 3 advisory is created. If not, then in step 3114, if the current element is present in set B (elements required to be in the document), then again the routine returns to looping step 3110 and no case 3 advisory is created. If the element is present in neither of sets C or B, then in step 3116 the routine creates a case 3 advisory and returns to looping step 3110. A case 3 advisory merely identifies the iCP element and mentions to the user that this element was established during protocol design but not referenced in the document being created. Note that in another embodiment, an advisory might be implemented which looks for iCP elements unreferenced in the iCD, whether or not they have assigned values.

Figure 32:
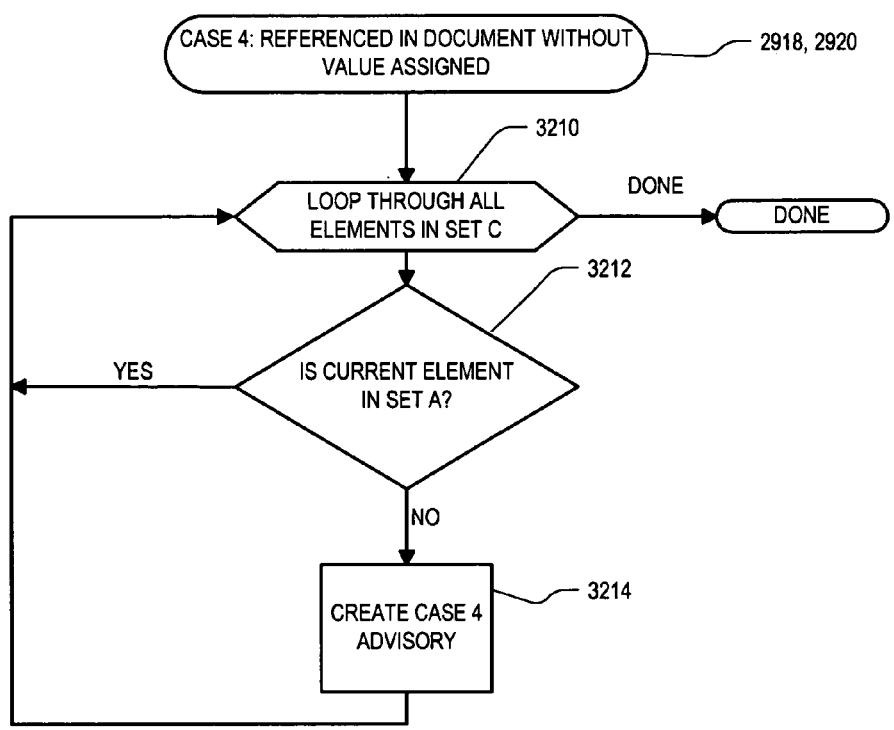

FIG. 32 is a flow chart illustrating how advisories for case 4 can be calculated. This advisory identifies elements that are referenced in the document, but which are linked to iCP elements that no longer exist (having been deleted by the author in a previous step), or which have been linked to an iCP element which has no value assigned. Essentially these iCD elements are merely placeholders either that identify a null-valued iCP element, or that point to an iCP element that is not currently present in the iCP instance. Placeholders such as these might arise, for instance, if the document template 120 contained the reference and the configurer intentionally removed the iCP element it pointed to—thus requiring the author to give it a value in the iCP.

Referring to FIG. 32, in step 3210, the routine loops through all entries in set C (iCP element references in the iCD 130). In step 3212, the routine tests whether the current element exists in set A (iCP elements that have assigned values). If so, then the routine returns to looping step 3210 and no case 4 advisory is created. If not, then a case 4 advisory is created in step 3214 and the routine returns to looping step 3210. In one embodiment, the case 4 advisory might simply identify to the user the type of the element contained in the document 130 and state that it is referenced in the document but has no value. In another embodiment, the case 4 advisory might also assist the user with a list of the various values that so far have been assigned to elements of the same type in the iCP 122.

In one embodiment, advisory rules can be implemented by running rules against the various items in the system of FIG. 1. Each advisory rule set is implemented as one or more logical assertions about specific data elements described in three XML documents: the iCP instance 122, the mapping specification 118, and the iCD instance 130, as converted to XML by WorX for Word. WorX for Word is a plug-in to Microsoft Word, available from HyperVision, Ltd., Chicago, Ill., that extends Word to support XML and structured authoring bi-directionally.

Assertions take the form of tests that can resolve to a Boolean result. If such a test fails, then this fact is communicated back into the protocol design tool 110 along with sufficient contextual information to produce a message which is of help to the user.

Normally, XSL transformation technology is used to produce an output document that is a modification or concatenation of information from its input sources. In the present embodiment, however, no document is generated. Instead, the system is interested only in the callbacks.

One of the primary advantages of the XSL syntax in this particular module of the system is the economy with which one can express relatively complex concepts in a declarative way. In addition, having this logic external to the application itself means that it can be modified according to the needs of each study sponsor design group without the need to re-create the release core protocol design tool 110. The economy of expression can be illustrated by the following example from the core of Advisory 1 (visit with no tasks):

<!—Assert that there is at least 1 TaskVisit associated with the current Visit—>
    <xsl:when
      test="count($ICP_DOC_ELEM/StudySchedule/Schedule/TaskVisits/TaskVisit[visitID/@ID=current( )/@ObjID])> 0">
    </xsl:when>

This test returns the count of TaskVisit associations for the current visit. If that count is greater than zero, then the rule has passed. If this were to be expressed in a procedural way, then its pseudocode might look like this:

Count=0
  Foreach TaskVisit in All TaskVisits
  If (thisTaskVisit.VisitID=CurrentVisit.ID)
    Count=1
    Break
  End If
  End For
  If (count>0)
  CallError(CurrentVisit)

It can be seen that the XSL syntax simplifies advisory rule set authoring, maintenance and customization considerably. A number of advisories using the XSL syntax are set forth in the file POCCorexslt.txt in the CD-ROM appendix.

Many other advisory rules can be implemented in various embodiments, and called for by the iCD model 116 for execution with respect to a particular document type. In one further example, an advisory rule detects elements that are missing in order for a protocol document to be able to create a valid export according to an external data specification, such as the data specification for clinicaltrials.gov or the data specification for the Protocol Patient Viewer (PPC). In yet another example, an advisory rule determines what elements are missing in order for protocol document to satisfy ICH E6, section 6. In still another further example, an advisory rule checks for the presence in a document instance of a required complex object, such as an SOA table or narrative. Such an advisory rule could, for example, check in the document for an identification code that the protocol design tool 110 inserts into the document in association with the complex object when the complex object is generated. In still another further example, an advisory rule checks for the presence in a document instance of certain document sections required for the particular document type.

Yet another advisory rule, referred to herein either as "Outcomes involving measurable change" or "Baseline Measures", advises the protocol writer when the current protocol has one of the following problematic conditions:

(a) includes an outcome which involves measuring a change, the protocol indicates a baseline measure for that outcome at a particular task-visit, but the protocol does not indicate another later task-visit which is used to measure for that outcome;

(b) a task-visit is noted as a baseline measure, but no subsequent measure is done (regardless of a linked outcome);

(c) an outcome is noted as one that involves measure of change, a task-visit exists in the protocol to measure for that outcome, but no corresponding baseline measure is noted at an earlier task-visit.

To implement this advisory, the model embodiments described above are extended to capture when a measure is a "baseline" measure as well as when an outcome is of the type in which a "change" is being measured. Together these two modeling extensions can be used implement the "Outcomes involving measurable change" or "Baseline Measures" advisory rule.

Advisory rules can be defined also for document templates such as 116. Since a document template in the embodiment of FIG. 1 is merely an iCD instance 130 that an author has not yet begun working on, advisory rules applicable to document templates can be executed by the protocol advisory service 134 in much the same way that it executes advisory rules on iCD instances. This general approach and the machinery described can also be used to implement non-regulatory authoring policies and conventions of the sponsor design group. By incorporating these self-documenting checks directly into the document configuration, the user is relieved of the need to execute an unlinked series of sponsor-required processes by hand. Typically, this can reduce effort and increase throughput of a sponsor design group as a document is passed from stakeholder to stakeholder.

Mapping Specification

The mapping specification 118 (FIG. 1) is contained in a set of XML documents. The purpose of the Mapping Specification document, is to provide the system with configuration information relevant to each of the iCP element types that can be collected during document creation. This configuration data is one of the ways that an individual organization can impress its specific requirements or processes upon the finished product. For instance, variations in terminology can be resolved wherein the Mapping Specification determines how an entity is to be known in the context of a specific sponsor design group when the system's uniform protocol schema is using another name for that entity. Another potentially organization-specific configuration detail specifies the "requiredness" or "defaultedness" of each element type in a given document type. The Mapping Specification also contains information which does not specifically relate to configuration but is used by the system: for instance, to guide the instantiation of business objects and domain entity linkage. While the Mapping Specification defines each element type available in the iCP Schema, some element types can and likely will be instantiated multiply in an iCP instance, while other element types defined in the Mapping Specification will only exist in a one to one relationship with an iCP instance. Mapping specifications for Domain Objects (as described below) which can be instantiated multiply in the iCP are known as Template specifications.

Before the designer or author begins designing a clinical trial protocol using the flowchart of FIG. 9, typically the controlling organization will prepare the document template 120 by configuring various aspects based on the mapping specification 118. This document template can serve as the starting point for the documents of many trial document instances, provided that the elements, rules and dynamic templates which formed the configuration satisfied the requirements of that document type. For instance, a Mapping Specification could describe the elements and document templates that served as a starting point for all Phase III Trial documents in Oncology, while in another embodiment, a Mapping Specification could serve for all Phase IV Pain Trial documents. As mentioned, any number of document templates can be created by configuration based on a single mapping specification such as 118. The mapping specification itself can be one of several created in accordance with a common metadata file (XML schema) that defines the element building blocks that can be used in a mapping specification. With particular relevance to the present discussion, a metadata file called eChooser.xsd defines the elements that can be included in the section of a mapping specification that defines the elements for element chooser pane 1014 (FIG. 10).

Figure 33:
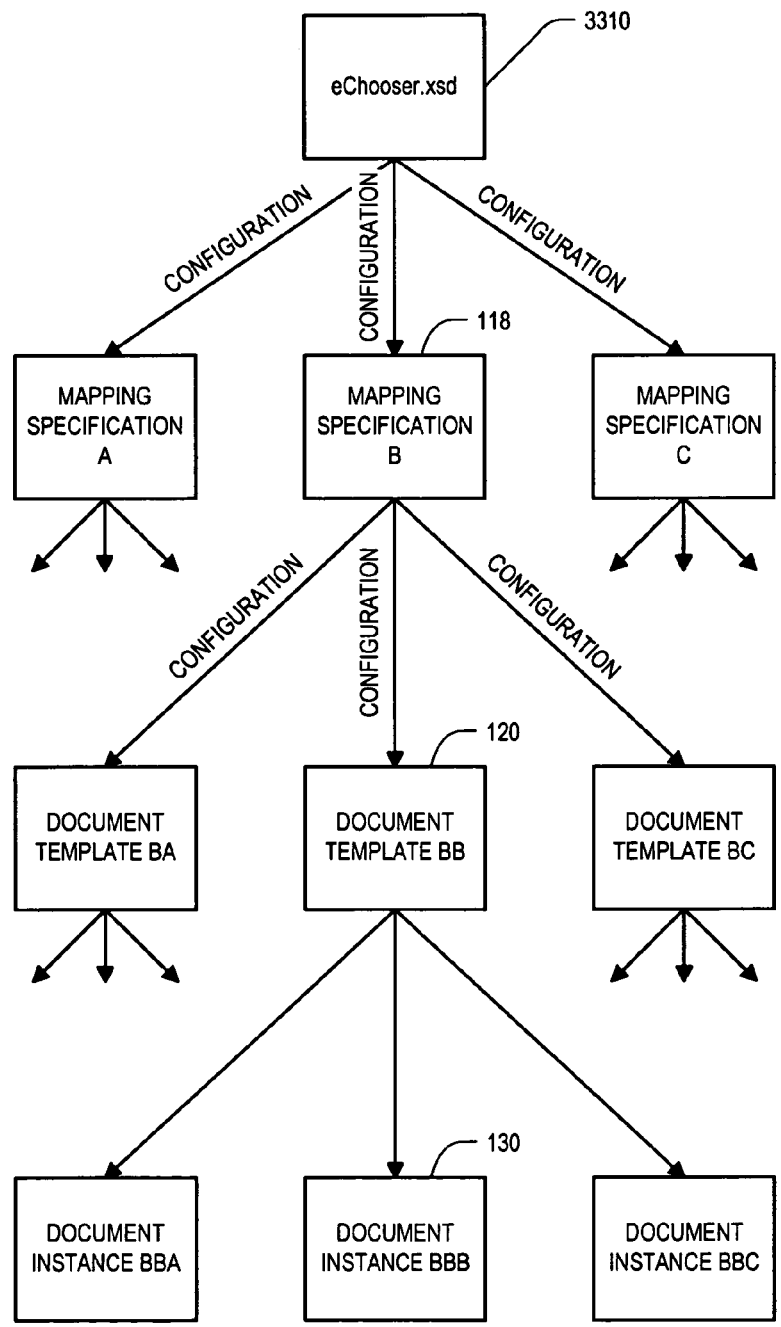
FIG. 33 is a diagram illustrating a hierarchy of specifications and templates.

FIG. 33 is a diagram illustrating this hierarchy of specifications and templates. As can be seen, the eChooser.xsd metadata file 3310 defines building block elements for the element chooser section of several (three shown) mapping specifications, including mapping specification 118 (FIG. 1). Each of the mapping specifications can be used to create more than one (three shown) document template, including document template 120, based on mapping specification 118. Finally, as noted above, each of the document templates can be used to create more than one document instance, including document instance 130.

Figure 34:
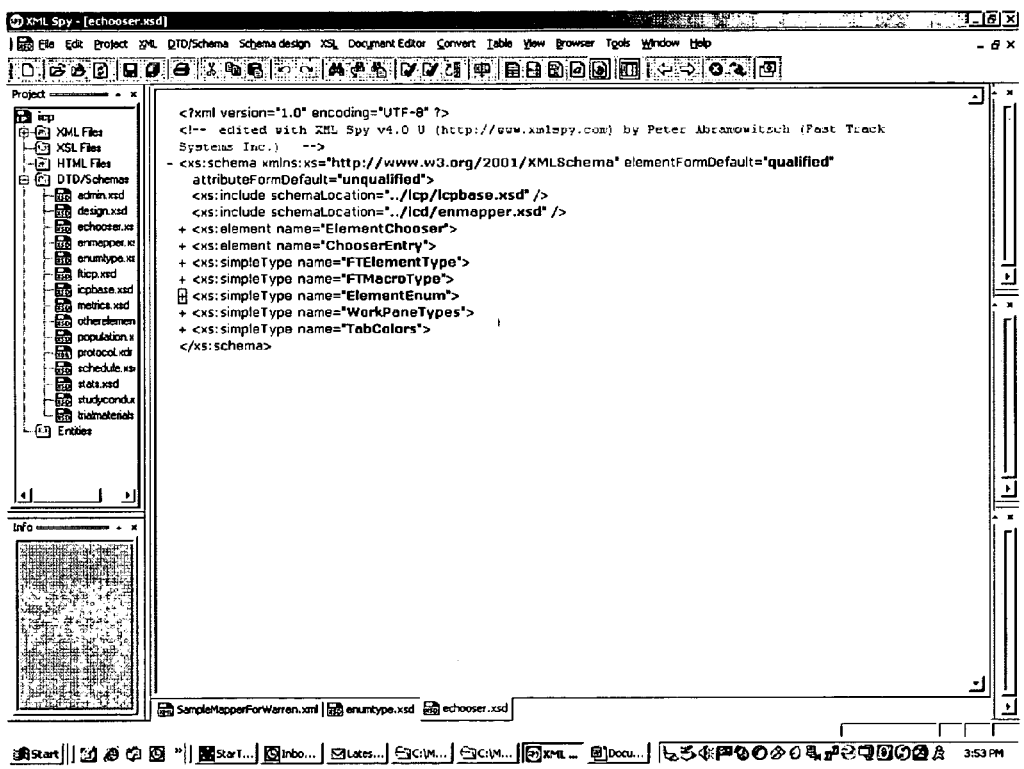
FIG. 34 is a screenshot showing top level sections of eChooser.xsd.

Accordingly, in order to understand the element chooser section of the mapping specification 118, it will be helpful to review the governing entries in the XML schema file. FIG. 34 is a screenshot showing top level sections of eChooser.xsd. It can be seen that among other things, eChooser defines items in the following categories:

ElementChooser. The root node of the mapping specification. It serves as the container for the set of concepts represented in the chooser ElementTab A categorization element which produces a collapsible major tree node in the user interface of the ElementChooser 1014, which is intended to represent a logical grouping of protocol elements under a name that is well known to the user.

Element Bucket defines a subcategory within an ElementTab, and is used by the configurer to provide a graphical division between groups of related elements in a Tab. This graphical division can be hidden if desired. It is useful if there are no conceptual subgroups within the protocol elements contained in an Element Tab.

ChooserEnry. Defines the visible and functional attributes of an entry in the Element Chooser 1014. (As noted above, in single instance elements—each ChooserEntry corresponds to one entry in the element chooser workpane 1014. But in the case of multiple instanced objects, Tasks for example, the ChooserEntry for Task is a template for all Instances of Task). The Element Chooser displays both domain objects such as an "Outcome" as well as atomic protocol elements—simple strings and numbers, which are the attributes of such objects. Consequently, ChooserEntries are capable of representing hierarchical or complex objects as well as the atomic concepts within these. The hierarchical nature of a ChooserEntry object is expressed in the eChooser schema representation of the Mapping Specification.

FTElementType. Defines the types of elements includable in documents ("template" (complex) elements and "simple" elements) and hence the types that will populate the ElementChooser 1014.

FTMacroType. Defines the types of Dynamic Templates which the system can execute.

ElementEnum. Defines the set of names corresponding to functions that are used to retrieve classes of elements to be used inside ElementBuckets WorkPaneTypes. Defines the workpanes that can be referred to by the chooser TabColors. Defines tab colors seen in element chooser workpane 1014.

Figure 35:
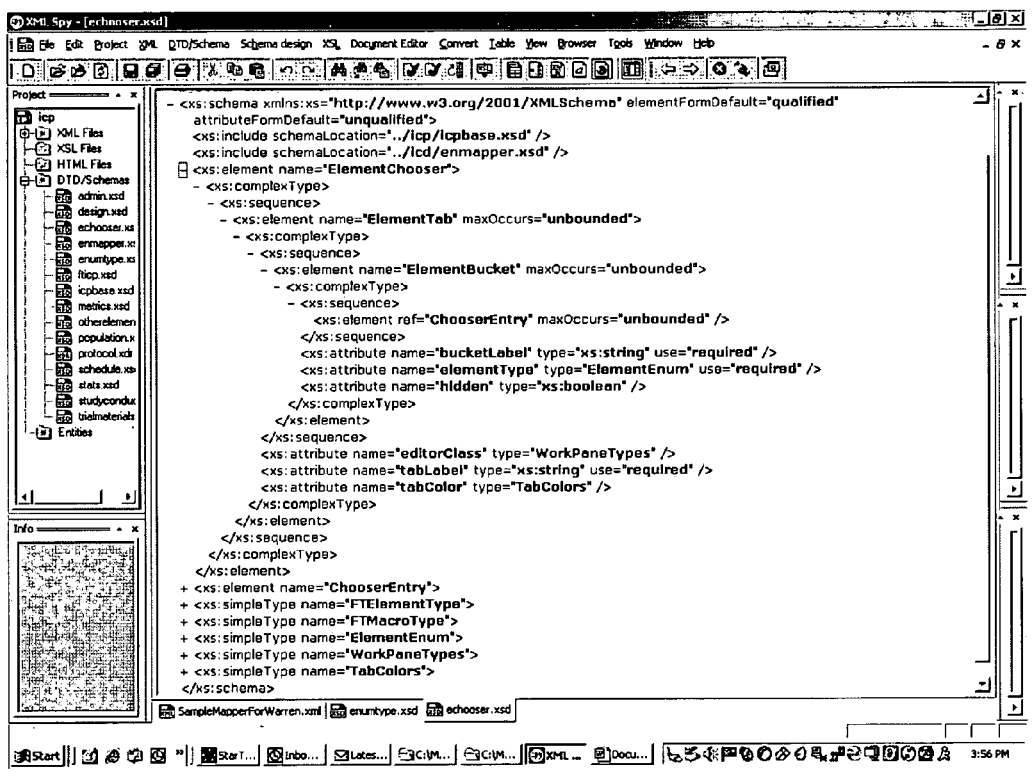
FIG. 35 is a screenshot showing the definitions in the ElementChooser section of eChooser.xsd.

FIG. 35 is a screenshot showing the definitions in the ElementChooser section of eChooser.xsd. According to this section, a single instance of an element chooser can be configured to contain zero or more sequenced ElementTabs. Each ElementTab can contain zero or more sequenced ElementBuckets, an editor Class (workpane to bring up if desired when user clicks on it), a tabLabel (display name) to show for that tab, and a tabColor. Each ElementBucket can contain zero or more ChooserEntrys. Each ChooserEntry contains a bucketLabel, an elementType, and a flag that indicates if the ElementBucket can be hidden if desired.

Figure 36:
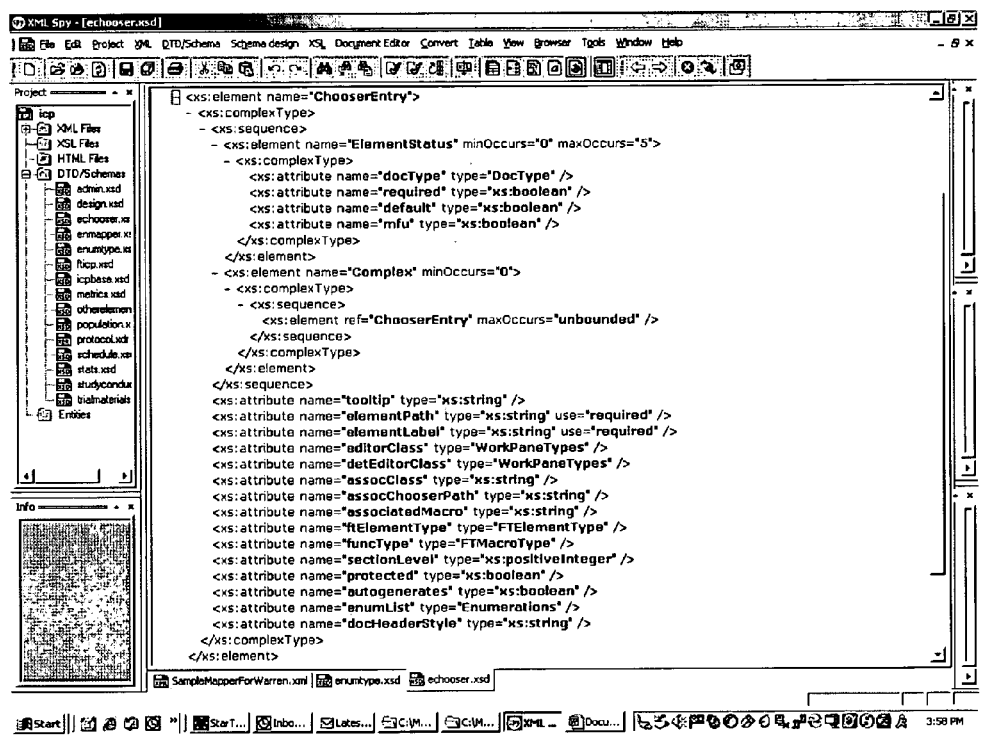
FIG. 36 is a screenshot showing the structure of each Chooser Entry in the mapping specification.

FIG. 36 is a screenshot showing the structure of each Chooser Entry in the mapping specification. It contains the following subsections, among other things:

ElementStatus: For each specified document type, "required" indicates whether the element is required to appear at least once with a value in any document of that type, "default" indicates whether this element has a fixed read-only value within a document of that type.

"Complex" if the current ChooserEntry includes a sequence of other ChooserEntry's (sub-entries) then a "Complex" element is used as the container of its sub-entries. The sub-entries will appear in element chooser pane 1014 as a submenu. While it is permitted to nest ChooserEntries to an arbitrary level of depth, the user interface enforces practical limits.

"tooltip" is a documentation string to be presented on a mouse-over (or potentially to be used for other purposes)

elementPath gives a path identifying the element in the iCP instance 122. Depending on the whether the Chooser entry defines a single instance or template element, this path is either complete(absolute) or a fragment of a path that is composed at runtime into an absolute canonical path.

elementLabel is the display name of the current chooser element, configurable by the study sponsor design group. For example, this allows an organization to use the term "endpoint" instead of "outcome", if desired. This name is used throughout the system wherever that element is displayed or input.

Editor Class if specified, this field identifies a workpane to invoke when the user clicks on this entry in the element chooser pane 1014.

detEditorClass if specified, this field identifies a work pane that is used to edit a single instance of this class of ChooserEntry when clicked: If both editor Class and detEditoraass have been defined for a ChooserEntry, then the detEditor Class value will take precedence associatedMacro: if specified, this field identifies a macro (Dynamic Template) that defines how an element of the current element type should be rendered in the document. The Mapping Specification contains entries for each of the available macros (Dynamic Templates) where they are listed in the order required by the sponsor design group. Typically, they will be displayed as entries in one or more Tabs (perhaps even in their own Tab). However, the associatedMacro field is used in the definition of a Complex element type as an optional way of associating that element with a specific Dynamic Template. For instance, if there were a Dynamic Template that emitted a single Visit with its Tasks, then the "associatedMacro" field of a Visit could be set to point to that DynamicTemplate. As a general rule, but not enforced in the system, DynamicTemplates that operate upon a group of complex protocol objects would be configured to appear as named procedures on their own, rather than as being silently associated with each of the displayed instances of a complex protocol object enumList: if possible values for this ChooserEntry are defined in an enumerated set, the set's name is declared in this field. The set itself is described in another document, not shown.

associatedClass:, associatedChooserPath: attributes which are used in certain ChooserEntries that describe elements which link to other protocol elements. For example, to describe an "outcome's" associated "objectives" these attributes help the system locate the objective being pointed to by any given instance of an outcome.

sectionLevel:, docHeaderStyle: are attributes used in a ChooserEntry that describes a Document Section ChooserEntry. These entries are not surfaced in the ElementChooser pane (1014) but in their own work pane: the DocumentSections work pane autogenerates: is a boolean attribute that applies to ChooserEntries that represent DynamicTemplates. If set, it indicates that the Template is eligible to be re-run each time the iCP dataset changes.

protected: is a boolean attribute. When set, it indicates that when its associated element reference or dynamic template content is embedded in a document it cannot be edited in the document itself and must be changed through a work pane.

Figure 37:
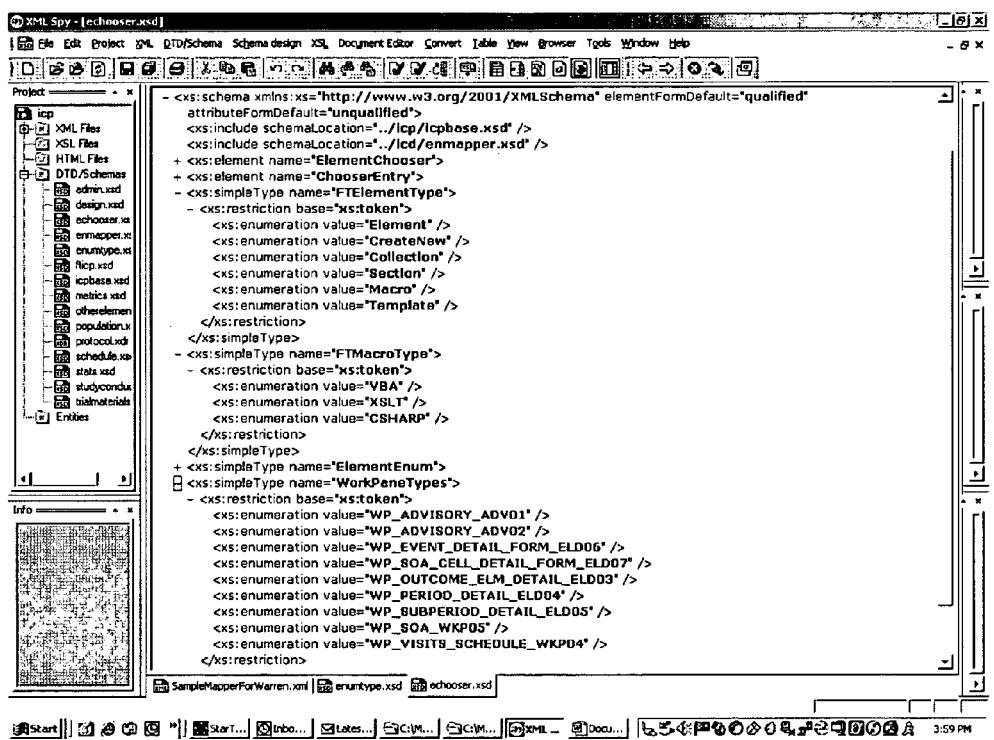
FIG. 37 is a screenshot showing the enumeration values available as FTElementTypes.

FIG. 37 is a screenshot showing the enumeration values available as FTElementTypes. These values are defined as follows. Note that a ChooserEntry's element type is singular.

Element: A ChooserEntry which models a discrete data element such as "study population" or a complex protocol object that can be instantiated only once Collection: A ChooserEntry which models a collection of like objects. Typically used as an attribute within a complex object to designate a collection of pointers to other objects (e.g., an Outcome's AssociatedObjectives). In this case, the Collection ChooserEntry is a single element which the system will display in a submenu as a collection of aliases to the associated objectives. The concept of alias is discussed below.

Template: indicates that the ChooserEntry defines an protocol object that can be instantiated multiply. This signals the system that the elementPaths defined for this ChooserEntry and its sub components are fragments for composition rather than complete paths Section: indicates that the ChooserEntry is of type DocumentSection rather than a protocol element Macro: indicates that the ChooserEntry is a handle to a DynamicTemplate procedure CreateNew: is a null ElementType which is used to display a navigational entry in the ElementChooser (1014) rather than representing an actual protocol object.

FTMacroTypes: VBA, XSLT and CSHARP represent the three platforms on which DynamicTemplates can be created. The values of this enumeration help the system locate the procedure to execute.

FIG. 37 also shows the enumeration values available as WorkPaneTypes. Some of the work pane types enumerated here are illustrated in screenshots of their own in other figures herein.

Figure 38:
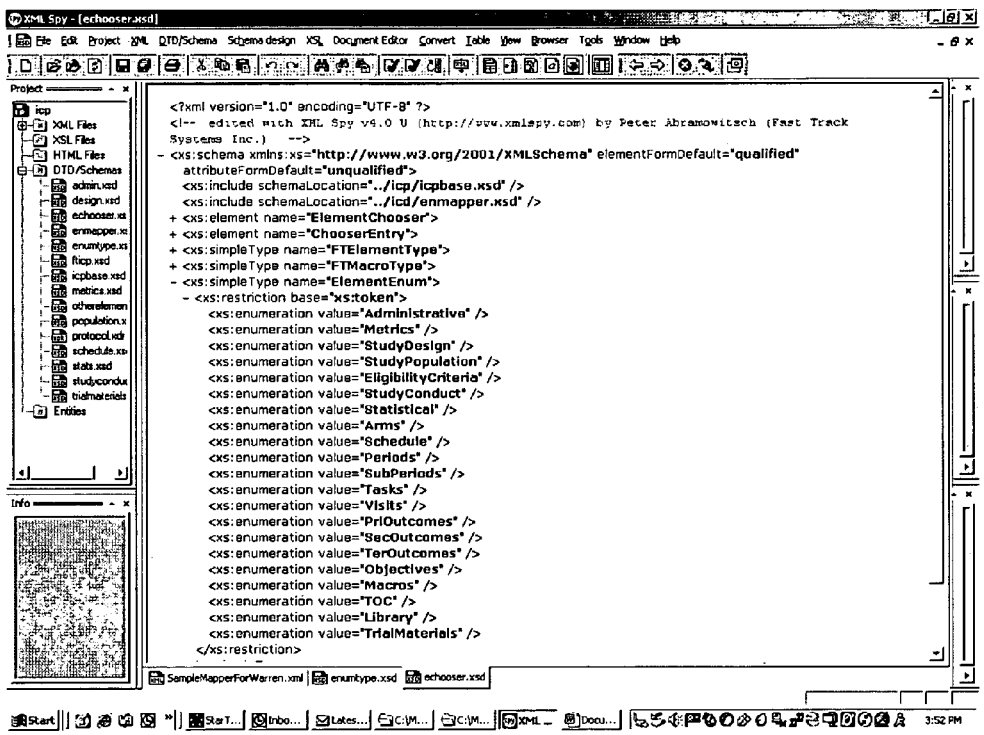
FIG. 38 is a screenshot showing the enumeration values available as an ElementEnum.
Figure 39:
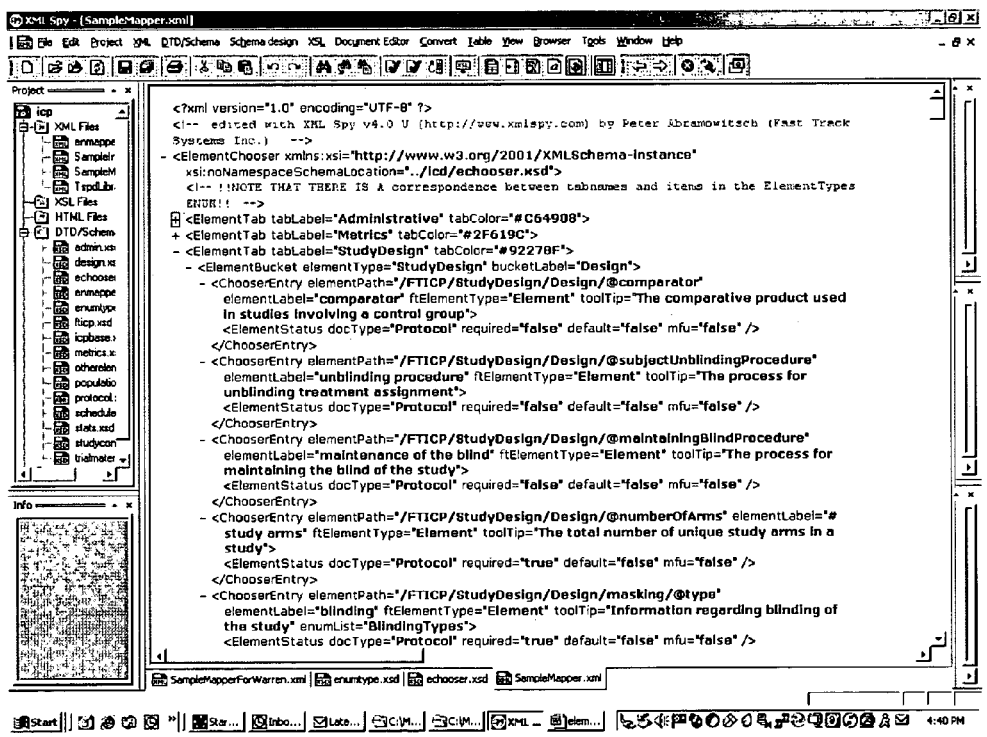
FIGS. 39, 40, 41 and 42 are screenshots which together show a section of an example XML mapping specification conforming to an eChooser.xsd schema.
Figure 40:
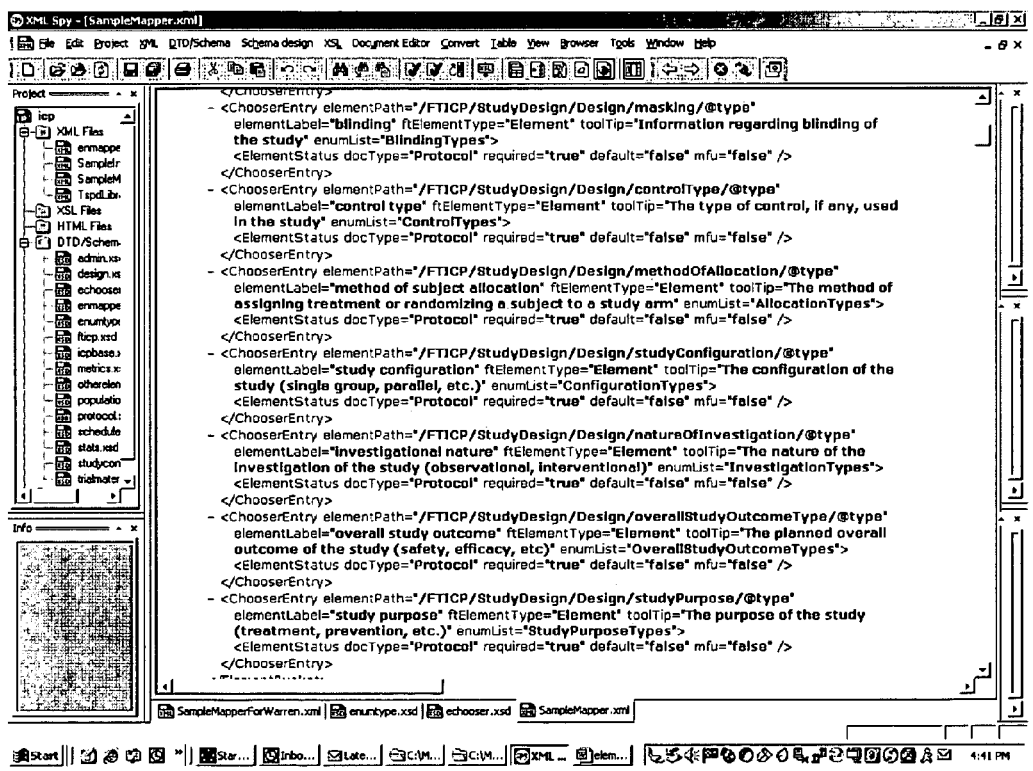
Figure 41:
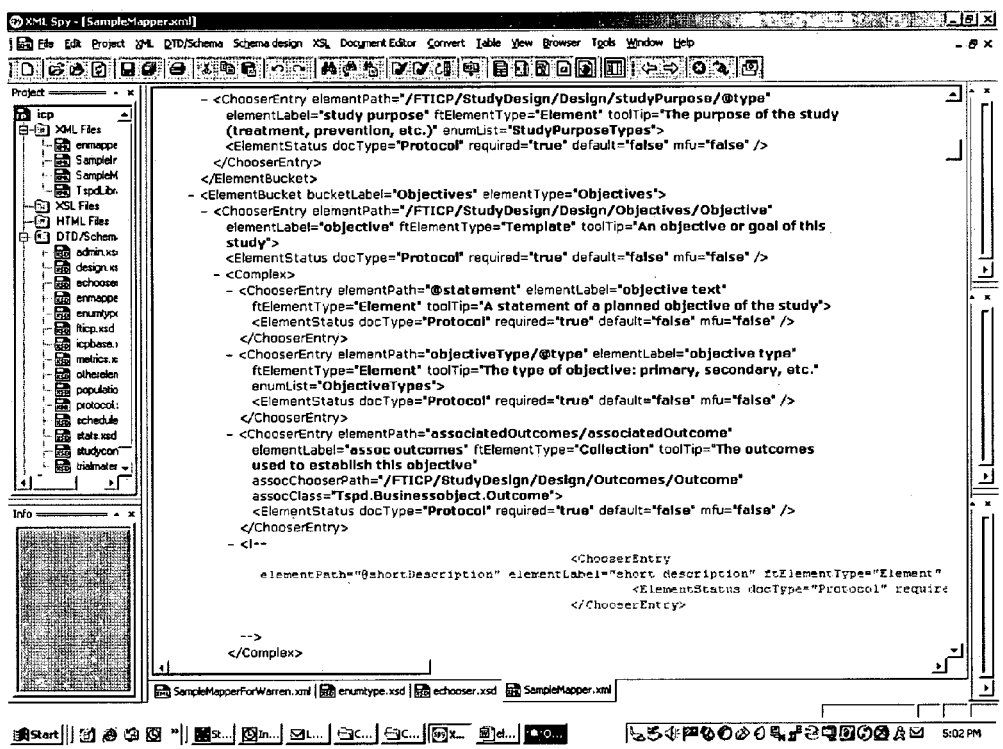
Figure 42:
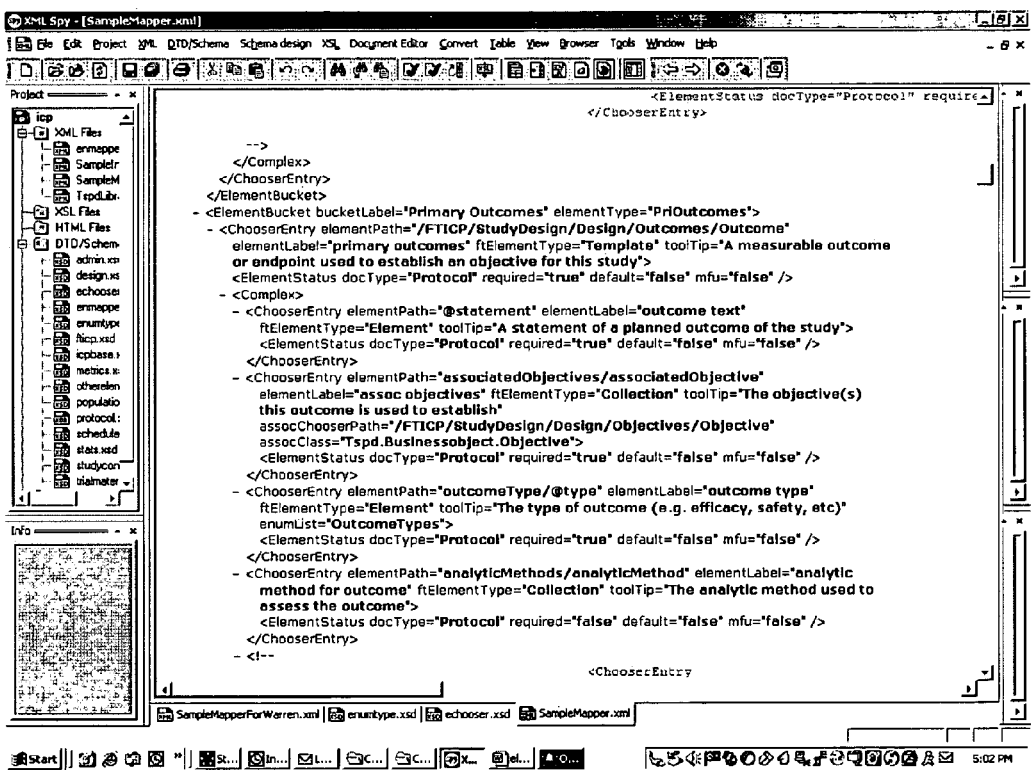

FIG. 38 is a screenshot showing the enumeration values available as an ElementEnum. ElementEnum provides a mapping between element types and functions dedicated to retrieving all instances of a class of elements from the iCP for display in the Element Chooser 1014. Thus if the Mapping Specification describes an Outcome (a single Templated element for the class type: Outcome) the ElementChooserPane will be asked to display all instantiated Outcomes. Thus, the value of ElementEnum is used by the protocol design tool 110 to determine which function is needed to display the list of Outcomes at this position in the Element Chooser Pane 1014.

FIGS. 39, 40, 41 and 42 are screenshots which together show a section of an example XML mapping specification 118 conforming to the eChooser.xsd schema 3310. The section shown in these figures includes Administrative, Metrics, StudyDesign element tabs. The StudyDesign tab is expanded to show three of the included element buckets, called StudyDesign, Objectives, and PrimaryOutcomes. Each of these element buckets is further expanded to show a number of chooser entries to be made available as sub-menus under these element buckets. It can be seen that several of the ChooserEntry's shown in these figures include a "required=true" attribute, meaning the document is required to include at least one element of the type of each of such ChooserEntry. Failure to include at least one of each such element will result in a case 1 or case 2 missing required element reference advisory. In the "StudyDesign" element bucket, the required elements in this example include (among others):

study arms (total number of unique study arms in a study);

blinding (information regarding blinding of the study);

method of subject allocation (the method of assigning treatment or randomizing a subject to a study arm);

study configuration (the configuration of the study (single group, parallel, etc.));

investigational nature (the nature of the investigation of the study (observational, interventional));

overall study outcome (the planned overall outcome of the study (safety, efficacy, etc));

study purpose (the purpose of the study (treatment, prevention, etc.)).

The Objectives bucket also includes an "objective" element with attribute "required=true". The effect of this requires some background discussion. As noted elsewhere, a complex element such as Objective can only be completely rendered by a Dynamic Template. Otherwise, when referring to an "Objective" in the context of the system of FIG. 1, one is normally referring to its alias. The alias for an element type is defined in the iCP schema and is defaulted into the element's instance on creation. For example, the alias for an Objective is defined by the current configuration as its "statement" attribute. The alias attribute is known as its InstanceLabel and its value in an Objective is set to "statement". So simply inserting an Objective in the current document is equivalent to inserting its "statement" attribute. Thus, omission of an Objective's "statement" from the document will cause an advisory to be raised because the "requiredness" setting of a complex element is inherited by the alias by which that object is known in the system.

Figure 43:
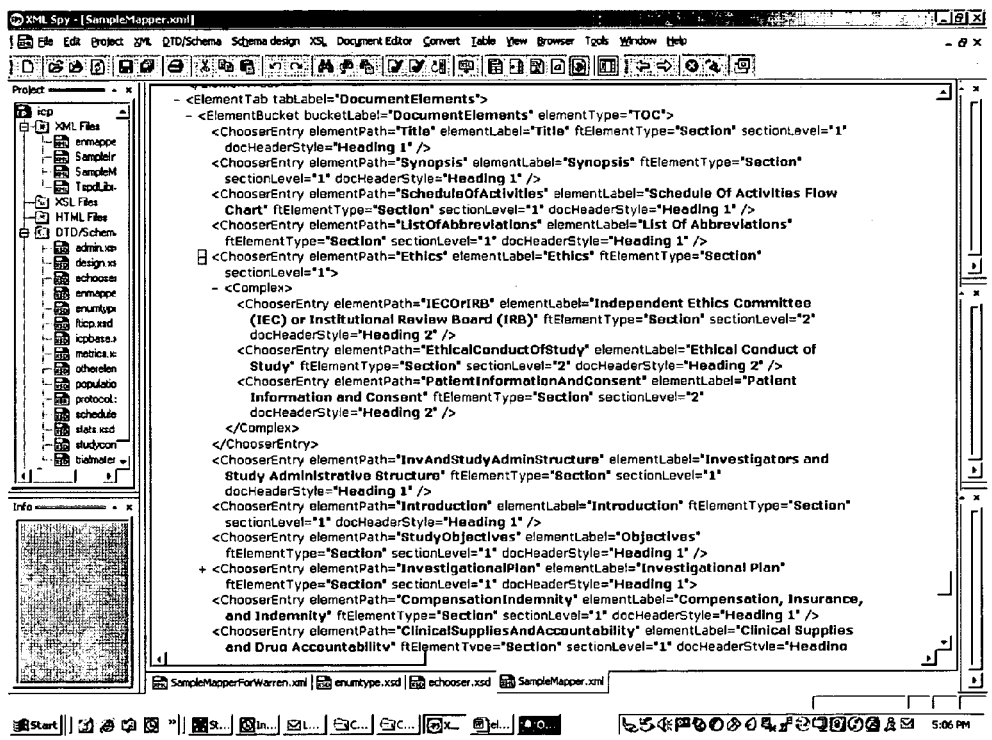
FIG. 43 is a screenshot illustrating a DocumentElements elementTab section of a mapping specification.

FIG. 43 is a screenshot illustrating a DocumentElements elementTab section of the mapping specification 118. This elementTab describes the document elements—the sections that can be used in the document—along with their heading style, label that should appear, and level of indentation. In the embodiment of FIG. 43, chooserEntry's do not include the "required" attribute. In another embodiment, such entries could include the "required" attribute, and the case 1 or case 2 missing required element reference advisory (or another protocol advisory) might be generated in response to the absence in the document of a document section indicated in the mapping specification 118 as "required=true".

The XML mapping specification 118 also includes a special tab for dynamic templates defined for use with the document. These template procedures, when invoked, will insert text and element references automatically into the document, typically at a user-specified position. After placing the document selection cursor at a desired position in the document creation window 1016, the user can invoke a Dynamic Template by double-clicking the Dynamic Template name in the element chooser pane 1014. Dynamic Template elements also can be pre-placed in the document template by the configurer and will expand dynamically when suitable iCP content is inserted. In one implementation, these Dynamic Templates will render information from the iCP instance 122 into the document. Different Dynamic Templates can be defined to render the same information into the document, each at a respective location specified by the user, and each in a different format. For example, one Dynamic Template might be defined to render the SOA as a table in the document, whereas another Dynamic Template, also available to the user through the element chooser pane 1014, might be defined to render the SOA in a narrative format. Each chooser entry in the Dynamic Templates section defines how to label the dynamic template in the element chooser pane 1014 (display name for the user), what editor should be invoked if the user clicks on the rendered object in the document, the type of macro implementation (VBA, XSLT or CSHARP), where to find the macro procedure, and whether the resulting text that is rendered in the document should be protected (read-only).

Another embodiment of an XML mapping specification 118 is submitted herewith in the CD-ROM appendix in file SampleMapper.xml.txt. This specification includes an ElementTab for "Tasks", having an ElementBucket of the same name. In this bucket has only one ChooserEntry, a template-type chooser entry, also called "Tasks". This chooser entry refers to an editor workpane like that of FIG. 15, and includes chooser sub-elements for identifying (among other things) the name of a task, the person responsible for carrying out this task, some detail about the task, and its duration. The example mapping specification in SampleMapper.xml.txt also includes an ElementTab for "StudySchedule", with one ElementBucket called "Schedule". This element bucket includes template-type ChooserEntry's for "period", "subperiod", "visit", "taskVisit" and "purpose of task at visit". Each of these sub-elements has an associated editor workpane. The "period" template-type chooser entry includes sub-elements for the name or identifier of a period within the study, additional textual information pertaining to this period, and the duration of this period in the study, among other things. The "subperiod" template-type chooser entry includes sub-elements for similar information. The "visit" template-type chooser entry refers to an editor workpane like that of FIG. 26, and includes the following sub-elements, among others: the name or identifier of a visit within the study, the time window in which a visit can take place, the study day or time relative to day 0 for this visit, additional textual information pertaining to this visit, and the duration of this visit in the study. The "taskVisit" template-type chooser entry refers to an editor workpane like that of FIG. 28, and includes the following sub-elements, among others: the purpose for this task at this visit, an associated outcome object, textual detail pertaining to the performance of this task at this visit, and duration of this task during this visit. The "purpose of task at visit" template-type chooser entry includes the following sub-elements, among others: a pointer to an enumerated purpose type, and a user supplied purpose for this task at this visit.

Two Stage Schema Design

As can be seen, the document architecture model of the system of FIG. 1 relies heavily on the concept of references in order to decouple the representation of embedded protocol elements from their instances. Isolation of presentation from data is common in the development of user interfaces, especially in what is conventionally known as "structured documents". But in conventional structured document systems, the data is made persistent in a backing store (such as in an XML document) and the formatting is maintained in a stylesheet that defines how the various elements are to be rendered.

The system of FIG. 1, however, has additional requirements that make the task significantly different than conventional structured documents. First, the document under development is not structured as in a form. While a series of Document Sections may be configured to appear or even be required, the internal structure of these sections is not predetermined and cannot be forced into a constricting schema. Second, structured protocol elements do not "belong" to an instance of a document, but to the iCP. They are "used" by one or more trial related documents in the written flow of free text or within structured expressions that are automatically generated into a document. The typographic formatting of these elements is not a characteristic of the element but of the context in which the element is found.

Third, it is desirable that a user of the system of FIG. 1 be able to alter the position of or even remove the structured element from the document without affecting its instance in the backing store.

Fourth, a single element might appear in multiple contexts within the same document and if there is an underlying change to the element value, it is required that all representations should change text value with minimal change to the extant formatting.

Fifth, it is desired that the user be able to call into existence in the backing store a previously uninstantiated element and then generate one or more references to it in the document.

Sixth, it is desired that the user be able to embed a reference to an uninstantiated element into the document and instantiate it in the iCP later.

In the system of FIG. 1, these requirements are achieved by providing two levels of backing store for a given editing session: a structured repository of elements known as the iCP Instance 122 that is shared between all instantiated documents for a given trial, and a repository of the evolving document structure known as the iCD instance 130, which includes all the free text that adorns the raw iCP data. The iCP instance 122 contains elements and associations between elements, together constituting the collected domain information about the trial. This is the information which is validated and exported to downstream applications. The iCD instance 130 refers to the iCP instance 122 through object references managed by dedicated XML "Protocol Reference" nodes in the document. The life cycle of these Protocol Reference nodes is partially decoupled from that of the elements to which they point in the sense that a value can exist in the iCP without being used in a given document. Similarly, the document can be made to refer to an iCP element that does not yet have a value.

Several benefits arise from the two level schema design. In particular, wherever an element is used multiple times in a single document or across multiple document types, the text values will always be kept synchronized with each other. Additionally, multiple document types can share the same data elements. Furthermore, a group of trials can share a similar core data schema and thus be mined for embedded data relative to trial design while having radically different visual and organizational characteristics as physical documents, and a single set of advisories can be used to test the integrity of multiple protocols authored by users with differing writing styles.

The document schema, or iCD model 116 declares four basic element types: Protocol Reference, Library Reference, Dynamic Template, and Document Section. In general, the schema declares that a well formed document can have mixed free text and any number of each of these elements in any order. It further stipulates that Protocol References and Library References cannot contain other elements or mixed text. Since protocol references are used to implement the two stage schema, the present discussion will be limited to these.

The ProtocolReference element is embedded into the subject document whenever the document must include text from a corresponding iCP element. It serves as a link between a physical range in the user document 130 and a node somewhere in the iCP instance 122. During an editing session, this Link is exercised to refresh the document image when the iCP is changed through the system's workpanes or to refresh the document image from the iCP when an iCP element is edited from within a region in the document pane 1016. Thus a bi-directional update path is realized by the Reference element in the context of the system. While a subject document is not being edited and is being viewed in a conventional document viewer or printed, the protocol references are represented by the text value of their corresponding iCP elements at the time of last save.

The constituent attributes of a Reference Element are:
elementPath: Calculated by the system at the time the reference is created to reflect the canonical path of the iCP element to which this reference refers.
detPanesClass: Copied from the Mapping Specification's detEditorClass
deleted: Boolean flag set if the iCP element pointed to had a value a value at one time, but is currently null
unlinked: Boolean flag set if the iCP element has never had a value.
elementLabel: Copied from the Mapping Specification. Indicates the user's friendly name for this element.
default: Boolean, copied from the Mapping Specification to indicate that the value in this references was supplied at configuration time.
required: Boolean, copied from the Mapping Specification to indicate that if removed from the document. It may signal a warning if it is the last instance of this ElementType
wkPaneClass: Copied from the Mapping Specification to indicate which work pane class should be brought up from a context menu selection on this object
enumList: Copied from the Mapping Specification. If set, the name of the constrained set of values that the pointed-to iCP element can have Most of these attributes are copied from the Mapping Specification at the time the Protocol reference is instantiated in the document. This is an optimization which makes it possible for the system to react quickly to changes in the document without having to look up the Mapping Specification each time an Element Reference is accessed in the document. In another embodiment, the attributes might not be copied from the Mapping Specification, but rather simply referred to there when needed.

While the iCD instance (document) maintains linkage with the iCP instance, the system uses another mechanism to maintain the dependency between documents that rely on a single iCP instance. So for example if the name of the sponsor and collaborators were initialized into the iCP during the writing of a protocol, it is highly likely that the StudyGuide document for the same trial will somewhere use these same data elements.

In order to centralize the tracking of element usage for each protocol element, the iCPDocRef element type has been declared in the iCP schema. It allows each protocol element in the iCP instance to contain an associated set of records indicating which attribute of which protocol element has been used in which document. In this way, warnings can be flagged when an element is no longer used in any document, or when one is changing the value of an element in the context of one document that will affect the contents of another document.

An iCPDocRef element has the following attributes:
DocType: The name of the Document Type or iCDModel name (e.g. protocol)
Refcount: The number of times the associated iCP element/attribute has been used in the named document type
ElementPart: The name of the attribute (null if the element itself) whose reference count is being stored The following is an example excerpt from an iCP instance in which three of the element's attributes are each used once in a document type entitled "Protocol":
<sampleSizeCalculation SystemName="Sample Size Calculation" InstanceLabel="SystemName" sampleSize="75" sampleSizeCalcMethod=" " power="0.80" anticipatedEffectSize="0.5° C." primaryStudyOutcomeID="1">
 <ICPDocRef DocType="Protocol" RefCount="1" ElementPart="anticipatedEffectSize"/>
 <ICPDocRef DocType="Protocol" RefCount="1" ElementPart="sampleSize"/>
 <ICPDocRef DocType="Protocol" RefCount="1" ElementPart="power"/>
</sampleSizeCalculation>

Figure 47:
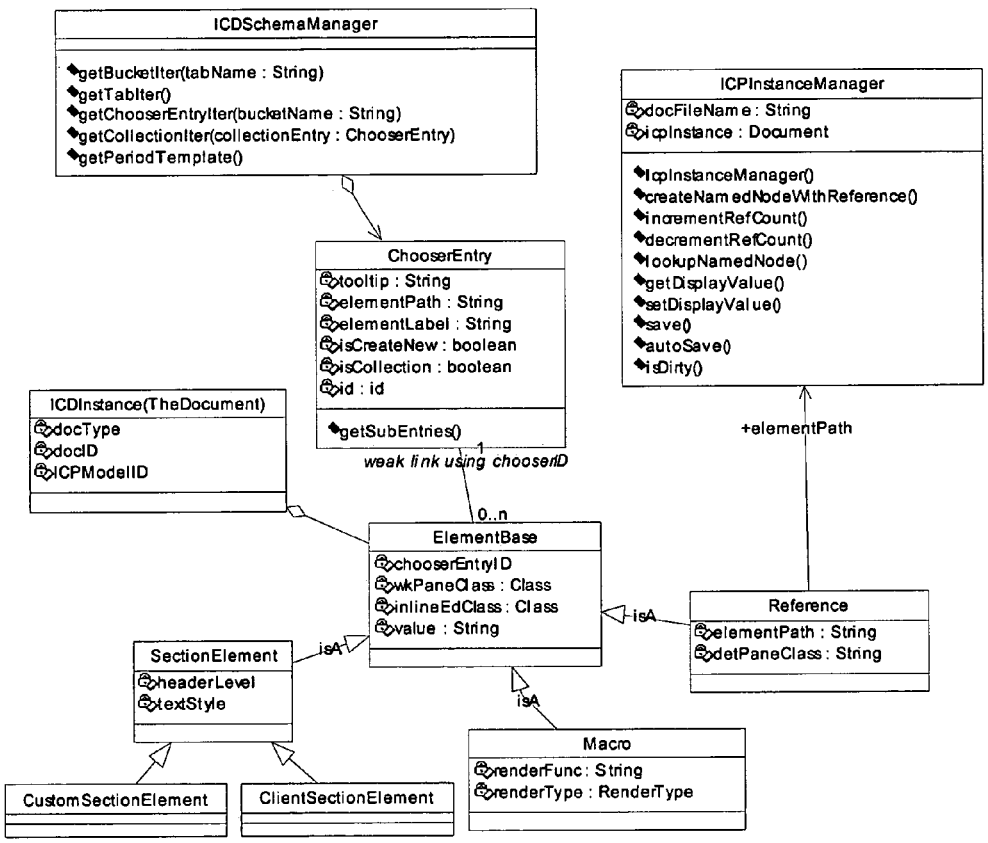
FIG. 47 is a Rose model illustrating a Class view of participants in the two-level schema.
Figure 48:
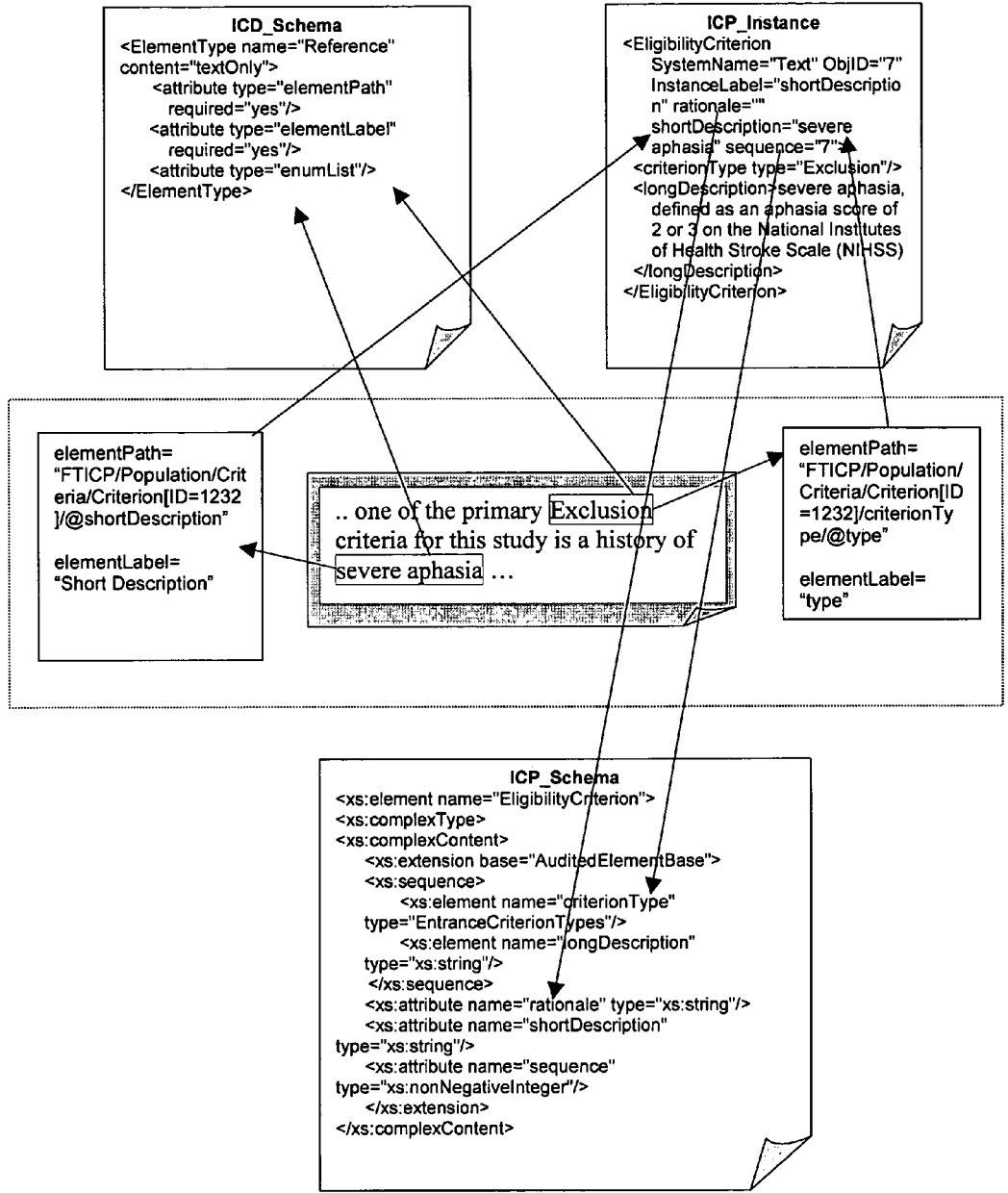
FIG. 48 is a schematic view of the two level schema in action in one embodiment.

FIG. 47 is a Rose model illustrating the Class view of participants in the two-level schema in one embodiment. FIG. 48 is a schematic view of the two level schema in action in one embodiment.

SUMMARY AND INDUSTRIAL UTILITY

The relative sizes of budgets would suggest that creating and writing a clinical protocol and associated study documents are trivial costs in the clinical development process when compared to trial execution expenses. Yet, growing evidence shows that errors or unnecessary complexity in protocol design are often the root cause of poor data quality and large time and cost impacts in the later steps of drug development. Thus, any investment in improving protocol design and quality can be an extremely high-leverage opportunity to avoid substantial downstream problems—both in the immediate clinical trial and in the much later clinical program's regulatory submission.

Although the content of each protocol differs, the operational features of a well-specified protocol are surprisingly similar. A robust operational protocol model can be created without requiring detailed pharmacologic or specific clinical knowledge. Thus, powerful applications that apply across all clinical domains can be created to analyze a protocol's operational features. In addition, by encoding protocols according to an operational protocol model, institutional memory can be captured in a structured, reusable manner. Substantial personnel turnover and project reassignments within the clinical operations team make it unlikely that a single individual has complete knowledge of the entire development plan for a specific agent. The operational protocol model provides a framework for capturing the design features and documenting the justifications for making design decisions. Currently, these justifications are either in people's heads or are part of unwritten company lore. When pressed by regulatory agencies 8-10 years later why a study was conducted or modified in a specific manner, either an individual involved in that study must be located or insight into the decision simply is no longer available. Because the operational data model in certain embodiments stores justifications for modifications along with the protocol design, this historical information becomes part of the institutional knowledge base and is accessible to current and later users.

Operational protocol models and their use with intelligent clinical documents as described herein ensure that quality goals are simply embedded in the protocol authoring process. Because paper documents remain the sine qua non for regulatory agencies, generating a complete protocol document from the operational protocol model is extremely useful. And because study designers are used to working with protocol design information in the environment and structure of a familiar study document rather than in a database, the development of an operational protocol model from information entered by a designer relative to the document itself is also extremely useful. The protocol authoring system described herein combines the structured methodology of operational protocol models with the familiar environment of standard word processing, thereby enabling familiar but informed protocol design to replace unstructured protocol writing, while automatically improving protocol quality from the very beginning of the protocol life cycle.

As used herein, a given event or value is "responsive" to a predecessor event or value if the predecessor event or value influenced the given event or value. If there is an intervening step or time period, the given event or value can still be "responsive" to the predecessor event or value. If the intervening step combines more than one event or value, the output of the step is considered "responsive" to each of the event or value inputs. If the given event or value is the same as the predecessor event or value, this is merely a degenerate case in which the given event or value is still considered to be "responsive" to the predecessor event or value. "Dependency" of a given event or value upon another event or value is defined similarly.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. As an example, whereas some of the embodiments described herein are implemented using an object-oriented model, other embodiments can be implemented using a relational database model. In addition, and without limitation, any and all variations described, suggested or incorporated by reference in the Background section of this patent application are specifically incorporated by reference into the description herein of embodiments of the invention. The embodiments described herein were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

The invention claimed is:

1. A method of developing a clinical trial protocol, the method comprising:
    receiving, by a computing device, a request to query a historical database, said request including user-specified filtering criteria having a clinical indication, trial phase and past time window, said historical database storing a plurality of individual tasks from multiple clinical trial protocols associated with past protocol dates, each individual task of said plurality of individual tasks being categorized for a particular clinical indication and particular trial phase;
    retrieving, by the computing device, a subset of individual tasks from said plurality of individual tasks based on said filtering criteria, said subset including at least a first individual task from a first clinical trial protocol and a second individual task from a second clinical trial protocol, said past protocol dates of said first clinical trial protocol and said second clinical trial protocol being within said past time window, each of the individual tasks included in said subset being associated with a numerical association strength criterion that indicates at least a predetermined strength of association of each of the individual tasks in said subset to other clinical trial protocols for the clinical indication and trial phase;
    receiving, by the computing device, a selection of at least one individual task from said subset; and
    creating, by the computing device, a structured protocol modeling database for instantiating at least one object of said clinical trial protocol based on said selection of the at least one individual task.

2. A method according to claim 1, wherein said user-specified filtering criteria further has text-search criteria.

3. A method according to claim 1, further comprising excluding, by the computing device, from said subset individual tasks whose association with previous clinical trial protocols fail a particular association strength criterion.

4. A method according to claim 3, wherein said particular association strength criterion excludes individual tasks from said subset that are indicated in said historical database as having been included in no more than a predetermined percentage of previous clinical trial protocols that satisfy user-specified filtering criteria.

5. A method according to claim 3, wherein said particular association strength criterion excludes individual tasks but an N number of individual tasks indicated in said historical database as having been most frequently included in previous clinical trial protocols that satisfy user-specified filtering criteria, said N number being a positive number.

6. A method according to claim 1, further comprising scheduling, by the computing device, one of said at least one individual task for performance in at least one event of said clinical trial protocol.

7. A method according to claim 1, further comprising instantiating, by the computing device, at least one task object corresponding to said at least one individual task in the structured protocol modeling database of said clinical trial protocol.

8. A method according to claim 7, further comprising:
instantiating, by the computing device, at least one event object in said protocol modeling database; and
linking, by the computing device, said at least one task object to said at least one event object.

9. A method according to claim 8, wherein linking comprises instantiating, by the computing device, at least one task-event object in said protocol modeling database, said at least one task-event object associating said at least one task object with said at least one event object.

10. A method according to claim 1, further comprising:
scheduling, by the computing device, one of said at least one individual task for performance in at least one event of said clinical trial protocol; and
entering, by the computing device, a purpose for performing said one of said at least one individual task scheduled for performance in said at least one event.

11. A method according to claim 10, wherein entering a purpose comprises selecting, by the computing device, a purpose from a list of offered purposes.

12. A method according to claim 11, further comprising requiring, by the computing device, entry of said purpose from said offered purposes.

13. A method according to claim 11, further comprising entering, by the computing device, an outcome for association with at least one of said offered purposes.

14. A method according to claim 13, wherein entering an outcome comprises selecting, by the computing device, an outcome from a list of offered outcomes.

15. A method according to claim 13, wherein entering an outcome, for association with a particular one of said purposes, comprises linking, by the computing device, an outcome object with a task-event object that links said at least one individual task said at least one event.

16. A method according to claim 10, wherein the purpose is efficacy testing.

17. A method according to claim 1, further comprising requiring, by the computing device, entry of an outcome for said at least one individual task.

18. A method according to claim 1, wherein retrieving said subset of individual tasks includes retrieving, by the computing device, a cost estimate for at least one of the individual tasks in said subset.

19. A method according to claim 18, wherein said cost estimate is retrieved in dependence upon a historical database that includes task costs.

20. A method of developing a clinical trial protocol, the method comprising:
receiving, by a computing device, a request to query a historical database, said request including user-specified filtering criteria having a clinical indication, trial phase and past time window, said historical database storing a plurality of individual tasks from multiple clinical trial protocols associated with past protocol dates, each individual task of said plurality of individual tasks categorized for a particular clinical indication and particular trial phase;
retrieving, by the computing device, a subset of individual tasks from said plurality of individual tasks based on said filtering criteria, at least a first individual task in said subset from a first clinical trial protocol and a second individual task in said subset from a second clinical trial protocol, said past protocol dates of said first clinical trial protocol and said second clinical trial protocol being within said past time window, each of the individual tasks included in said subset being associated with a numerical association strength criterion that indicates at least a predetermined strength of association of each of the individual tasks in said subset to other clinical trial protocols for the clinical indication and trial phase;
receiving, by the computing device, a selection of at least one individual task from said subset;
creating, by the computing device, a structured protocol modeling database for instantiating at least one object of said clinical trial protocol based on said selection of the at least one individual task;
receiving, by the computing device, at least one event for the clinical trial protocol; and
linking, by the computing device, said at least one individual task to said at least one event.

21. A method according to claim 20, further comprising:
generating, by the computing device, a table having said at least one event along a first dimension of said table and said at least one individual task along a second dimension of said table;
wherein linking comprises marking, by the computing device, with a user-perceptible distinguishing feature, at least one task-event linkage in said table at which said at least one individual task is assigned to said at least one event.

22. A method according to claim 21, further comprising providing, by the computing device, in dependence upon said at least one task-event linkage of said at least one individual task and said at least one event made, a total per-patient cost estimate for a member of the group consisting of: (1) a trial conducted according to said clinical trial protocol; and (2) an event from said at least one event.

23. A method according to claim 21, further comprising auto-generating, by the computing device, in a clinical trial protocol document, a schedule of activities table in dependence upon said at least one task-event-linkage.

24. A method according to claim 20, further comprising in said structured protocol modeling database, the computing device instantiating at least one task object corresponding to said at least one individual task.

25. A method according to claim 24, further comprising:
instantiating, by the computing device, at least one event object in said protocol modeling database corresponding said at least one event; and
linking, by the computing device, user-selected ones of said at least one task object to user-selected ones of said at least one event object.

26. A system to develop a clinical trial protocol, the system comprising:
a memory device comprising a historical database, the historical database storing a plurality of individual tasks from multiple clinical trial protocols associated with past protocol dates, each individual task of said plurality of individual tasks being categorized for a particular clinical indication and particular trial phase; and
a protocol design tool operatively connected to said historical database, said protocol design tool configured to:
receive a request to query said historical database, said request including user-specified filtering criteria having a clinical indication, trial phase and past time window;
retrieve a subset of individual tasks from said plurality of individual tasks based on said filtering criteria, at least a first individual task in said subset from a first clinical trial protocol and a second individual task in said subset from a second clinical trial protocol, said past protocol dates of said first clinical trial protocol and said second clinical trial protocol being within said past time window, each of the individual tasks included in said subset being associated with a numerical association strength criterion that indicates at least a predetermined strength of association of each of the individual tasks in said subset to other clinical trial protocols for the clinical indication and trial phase;

receive a selection of at least one individual task from said subset; and instantiate, in a structured protocol modeling database, at least one object identifying said at least one individual task.

27. A system according to claim 26, wherein the protocol design tool is further configured to exclude from said subset individual tasks whose association with the previous clinical trial protocols fail a particular association strength criterion.

28. A system according to claim 26, wherein the protocol design tool is further configured to instantiate at least one task object corresponding to said at least one individual task in the structured protocol modeling database of the clinical trial protocol.

29. A system according to claim 28, wherein the protocol design tool is further configured to:

instantiate at least one event object in the protocol modeling database; and link the at least one task object to the at least one event object.

30. A system according to claim 26, wherein the protocol design tool is further configured to:

schedule said at least one individual task for performance in at least one event of the clinical trial protocol; and insert into the protocol modeling database a purpose for performing said at least one individual task in the at least one event.

31. A system according to claim 30, wherein the protocol design tool is further configured to enter into the structured protocol modeling database, in response to user input, an outcome for association with said purpose.

32. A system according to claim 31, wherein the protocol design tool is configured to instantiate an outcome object for the outcome, and to link the outcome object with a task-event object that links said at least one individual task with said at least one event.

33. A system according to claim 26, wherein the protocol design tool is configured to retrieve said subset together with a cost estimate for at least one of the individual tasks in said subset, derived in dependence upon said historical database, each individual task of the plurality of individual tasks in said historical database including task costs.

34. A system according to claim 26, wherein the protocol design tool is further configured to:

receive at least one event for the clinical trial protocol; and link said at least one individual task to said at least one event.

35. A system according to claim 34, wherein the protocol design tool is further configured to auto-generate, in a clinical trial protocol document, a schedule of activities table in dependence upon link of said at least one individual task to said at least one event.

36. A system according to claim 34, wherein the protocol design tool is further configured to retrieve, in dependence upon the link of said at least one individual task to said at least one event, a total per-patient cost estimate for a member of the group consisting of: (1) a trial conducted according to the clinical trial protocol; and (2) an event from said at least one event.

37. A system to develop a clinical trial protocol, the system comprising:

a memory device comprising a historical database, the historical database storing a plurality of individual tasks from multiple clinical trial protocols associated with past protocol dates, each individual task of said plurality of individual tasks being categorized for a particular clinical indication and particular trial phase; and a protocol design tool operatively coupled to said historical database, said protocol design tool configured to:

receive a request to query said historical database, said request including user-specified filtering criteria having a clinical indication, trial phase and past time window;

retrieve a subset of individual tasks from said plurality of individual tasks based on said filtering criteria, at least a first individual task of said subset from a first clinical trial protocol and a second individual task of said subset from a second clinical trial protocol, said past protocol dates of said first clinical trial protocol and said second clinical trial protocol being within said past time window, each of the individual tasks included in said subset being associated with a numerical association strength criterion that indicates at least a predetermined strength of association of each of the individual tasks in said subset to other clinical trial protocols for the clinical indication and trial phase;

receive at least one event for the clinical trial protocol;

receive a selection of at least one individual task from said subset; and link said at least one individual task to said at least one event.

* * * * *